(12) United States Patent
Dietrich

(10) Patent No.: US 11,834,702 B2
(45) Date of Patent: Dec. 5, 2023

(54) METHOD FOR DETERMINING A MUTATION IN GENOMIC DNA, USE OF THE METHOD AND KIT FOR CARRYING OUT SAID METHOD

(71) Applicant: Dimo Dietrich, Berlin (DE)

(72) Inventor: Dimo Dietrich, Berlin (DE)

(*) Notice: Subject to any disclaimer, the term of this patent is extended or adjusted under 35 U.S.C. 154(b) by 537 days.

(21) Appl. No.: 15/743,951

(22) PCT Filed: Jul. 20, 2016

(86) PCT No.: PCT/EP2016/001237
§ 371 (c)(1),
(2) Date: Jan. 11, 2018

(87) PCT Pub. No.: WO2017/008912
PCT Pub. Date: Jan. 19, 2017

(65) Prior Publication Data
US 2021/0108255 A1  Apr. 15, 2021

(30) Foreign Application Priority Data
Jul. 16, 2015 (DE) ...................... 10 2015 009 187.5

(51) Int. Cl.
| | |
|---|---|
| C12Q 1/68 | (2018.01) |
| C12Q 1/6827 | (2018.01) |
| C12Q 1/6806 | (2018.01) |
| C12Q 1/6886 | (2018.01) |

(52) U.S. Cl.
CPC ......... *C12Q 1/6827* (2013.01); *C12Q 1/6806* (2013.01); *C12Q 1/6886* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2005/0064401 A1 | 3/2005 | Olek et al. | |
| 2006/0019278 A1* | 1/2006 | Lo .................. | C12Q 1/6883 435/6.11 |
| 2008/0050738 A1 | 2/2008 | Millar et al. | |
| 2008/0286787 A1* | 11/2008 | Campan ............ | C12Q 1/6858 435/6.12 |

(Continued)

FOREIGN PATENT DOCUMENTS

| | | |
|---|---|---|
| DE | 19951189 A1 | 5/2001 |
| WO | 2009/036922 A2 | 3/2009 |

(Continued)

OTHER PUBLICATIONS

Frayling et al, PCR-Based Methods for Mutation Detection, Molecular Diagnostics pp. 65-74, Ch. 7, 2010.*

(Continued)

*Primary Examiner* — Aaron A Priest
(74) *Attorney, Agent, or Firm* — Alan J. Morrison

(57) ABSTRACT

A method for determining a mutation in genomic DNA is described. The method is characterized in that the mutation analysis is performed with genomic DNA, in which at least a part of the cytosines contained therein has previously been converted into uracil or another base with a base pairing behavior or molecular weight distinguishable from that of cytosine.

1 Claim, 6 Drawing Sheets

Specification includes a Sequence Listing.

(56) References Cited

U.S. PATENT DOCUMENTS

| | | | |
|---|---|---|---|
| 2012/0101023 A1 | 4/2012 | Zwarthoff et al. | |
| 2013/0338032 A1 | 12/2013 | Godler | |
| 2014/0303001 A1 | 10/2014 | Steve et al. | |
| 2014/0322714 A1* | 10/2014 | Van Criekinge | C12Q 1/6881 435/6.11 |
| 2016/0208341 A1* | 7/2016 | Renard | A61P 35/00 |
| 2017/0137871 A1* | 5/2017 | Lai | C12N 15/1017 |

FOREIGN PATENT DOCUMENTS

| | | |
|---|---|---|
| WO | 2013/082043 A1 | 6/2013 |
| WO | 2013/084075 A2 | 6/2013 |

OTHER PUBLICATIONS

Redshaw et al, Quantification of epigenetic biomarkers: an evaluation of established and emerging methods for DNA methylation analysis, BMC Genomics. Dec. 23, 2014;15(1):1174. doi: 10.1186/1471-2164-15-1174.*

Deng et al, Simultaneous detection of CpG methylation and single nucleotide polymorphism by denaturing high performance liquid chromatography, Nucleic Acids Res. Feb. 1, 2002; 30(3): e13.*

Wang, J et al., Epigenetic changes of EGFR have an important role in BRAF inhibitorresistant cutaneous melanomas, J Invest Dermatol. Feb. 2015; 135(2):532-541.

Hartmann, O et al., DNA methylation markers predict outcome in node-positive, estrogen receptor-positive breast cancer with adjuvant anthracycline-based chemotherapy, Clin Cancer Res. Jan. 1, 2009; 15(1):315-23.

Liu, Y et al., Bis-SNP: combined DNA methylation and SNP calling for Bisulfite-seq data, Genome Biol. Jul. 11, 2012; 13(7):R61.

Laskar, RS et al., Association of HPV with genetic and epigenetic alterations in colorectal adenocarcinoma from Indian population, Tumour Biol. Jun. 2015; 36(6):4661-70.

Li, LC et al., Methprimer: Designing Primers for Methylation PCRs, Bioinformatics 2002, 18(11):1427-31.

Tusnády, GE et al., BiSearch: primer-design and search tool for PCR on bisulfite-treated genomes, Nucleic Acids Res. Jan. 13, 2005;33(1):e9.

Pattyn, F. et al, methBLAST and methPrimerDB: web-tools for PCR based methylation analysis, BMC Bioinformatics. Nov. 9, 2006; 7:496.

Den Dunnen, JT et al., Mutation nomenclature extensions and suggestions to describe complex mutations: a discussion, Hum Mutat. 2000;15(1):7-12.

Benson, DA et al., GenBank, Nucleic Acids Res. Jan. 2013;41(Database issue):D36-42.

Thompson, JD et al., Clustal W: improving the sensitivity of progressive multiple sequence alignment through sequence weighting, position-specific gap penalties and weight matrix choice, Nucleic Acids Res. Nov. 11, 1994;22 (22):4673-80.

Frommer, M. et al., A genomic sequencing protocol that yields a positive display of 5-methylcytosine residues in individual DNA strands, Proc Natl Acad Sci U S A. Mar. 1, 1992;89(5):1827-31.

Johnson, MD et al., Single nucleotide analysis of cytosine methylation by whole-genome shotgun bisulfite sequencing, Curr Protoc Mol Biol. Jul. 2012; Chapter 21:Unit21.23.

Lister, R. et al., Human DNA methylomes at base resolution show widespread epigenomic differences, Nature. Nov. 19, 2009; 462(7271):315-22.

Berman, BP et al., Regions of focal DNA hypermethylation and long-range hypomethylation in colorectal cancer coincide with nuclear lamina-associated domains, Nat Genet. Nov. 27, 2011; 44(1):40-6.

Van Oers, et al., "A Simple and FastMethod for the Simultaneous Detection of Nine Fibroblast Growth Factor Receptor 3 Mutations in Bladder Cancer and Voided Urine", www.aacrjournals.org, Clin Cancer Res 2005; 11(21) Nov. 1, 2005, 6 pages.

* cited by examiner

```
                           SEQUENCE LISTING

<160> NUMBER OF SEQ ID NOS: 94

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer to amplify unconverted
      (SEQ ID NO:3) and bisulfite-converted (SEQ ID NO:4) BRAF V600E
      locus

<400> SEQUENCE: 1
tcaattctta ccatccacaa aat                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer to amplify unconverted
      (SEQ ID NO:3) and bisulfite-converted (SEQ ID NO:4) BRAF V600E
      locus

<400> SEQUENCE: 2
agtaaaaata ggtgattttg gt                                               22

<210> SEQ ID NO 3
<211> LENGTH: 105
<212> TYPE: DNA
<213> ORGANISM: Homo sapiens
<220> FEATURE:
<223> OTHER INFORMATION: BRAF gene locus comprising the V600E mutation
      site

<400> SEQUENCE: 3
tcaattctta ccatccacaa aatggatcca gacaactgtt caaactgatg ggacccactc        60
catcgagatt tcactgtagc tagaccaaaa tcacctattt ttact                       105

<210> SEQ ID NO 4
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Bisulfite-converted (bisulfite strand II) BRAF
      gene locus comprising the V600E mutation site
```

<400> SEQUENCE: 4
tcaattctta ccatccacaa aataaatcca aacaactatt caaactaata aaacccactc    60
catcgaaatt tcactataac taaaccaaaa tcacctattt ttact                  105

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: qPCR detection probe targeting the bisulfite
      converted BRAF gene locus (SEQ ID NO:4) comprising the V600E
      mutation site

<400> SEQUENCE: 5
attcaaacta ataaaaccca ctcca                                         25

<210> SEQ ID NO 6
<211> LENGTH: 112
<212> TYPE: DNA
<213> ORGANISM: Homo sapiens
<220> FEATURE:
<223> OTHER INFORMATION: SHOX2 gene locus targeted in the course of
      methylation analyses

<400> SEQUENCE: 6
gtcccctgga cagccaggta atctccgtcc cgcctgcccg accggggtcg cacgagcaca    60
ggcgcccacg ccatgttggc tgcccaaagg gctcgccgcc aagccgggc ca           112

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer used to amplify the bisulfite-
      converted (SEQ ID NO:10) SHOX2 gene locus

<400> SEQUENCE: 7 gtttttttgga tagttaggta at                                           22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer used to amplify the bisulfite-
      converted (SEQ ID NO:10) methylated SHOX2 gene locus

<400> SEQUENCE: 8
taacccgact taaacgacga                                               20

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Blocker oligonucleotide preventing forward
      primer (SEQ ID NO:7) from binding to the bisulfite-converted
      unmethylated SHOX2 gene locus

<400> SEQUENCE: 9
taatttttgt tttgtttgtt tgattggggt tgtatga                    37

<210> SEQ ID NO 10
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Bisulfite-converted (bisulfite strand I) SHOX2
      gene locus derived from the genomic sequence SEQ ID NO:6

<400> SEQUENCE: 10
gtttttggga tagttaggta attttcgttt cgtttgttcg atcggggtcg tacgagtata    60
ggcgtttacg ttatgttggt tgtttaaagg gttcgtcgtt taagtcgggt ta          112

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: qPCR detection probe targeting the bisulfite
      converted methylated SHOX2 gene locus (SEQ ID NO:10)

<400> SEQUENCE: 11
ctcgtacgac cccgatcg                                         18

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sequencing primer used for Sanger sequencing
      of the bisulfite-converted BRAF gene locus SEQ ID NO:4

<400> SEQUENCE: 12
cttaccatcc acaaaataaa tcca                                  24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer used to amplify the unconverted
      EGFR exon 21 gene locus SEQ ID NO:15 comprising the L858R
      mutation site

<400> SEQUENCE: 13
gtttcagggc atgaactact tgg                                   23

<210> SEQ ID NO 14
<211> LENGTH: 22

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer used to amplify the unconverted
      EGFR exon 21 gene locus SEQ ID NO:15 comprising the L858R
      mutation site

<400> SEQUENCE: 14
cctggtgtca ggaaaatgct gg                                               22

<210> SEQ ID NO 15
<211> LENGTH: 208
<212> TYPE: DNA
<213> ORGANISM: Homo sapiens
<220> FEATURE:
<223> OTHER INFORMATION: Unconverted EGFR exon 21 gene locus comprising
      the L858R mutation site

<400> SEQUENCE: 15
gtttcagggc atgaactact tggaggaccg tcgcttggtg caccgcgacc tggcagccag      60
gaacgtactg gtgaaaacac cgcagcatgt caagatcaca gattttgggc tggccaaact    120
gctgggtgcg gaagagaaag aataccatgc agaaggaggc aaagtaagga ggtggcttta    180
ggtcagccag cattttcctg acaccagg                                        208

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer to amplify bisulfite-converted
      EGFR exon 21 gene locus SEQ ID NO:18 comprising the L858R
      mutation site

<400> SEQUENCE: 16
gttttagggt atgaattatt tgga                                             24

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer to amplify bisulfite-converted
      EGFR exon 21 gene locus SEQ ID NO:18 comprising the L858R
      mutation site

<400> SEQUENCE: 17
ccctaatatc aaaaaaatac taacta                                           26

<210> SEQ ID NO 18
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Bisulfite-converted EGFR exon 21 gene locus
      (bisulfite strand I) derived from SEQ ID NO:15 comprising the
      L858R mutation site
```

<400> SEQUENCE: 18

```
gttttagggt atgaattatt tggaggatcg tcgtttggtg tatcgcgatt tggtagttag    60
gaacgtattg gtgaaaatat cgtagtatgt taagattata gattttgggt tggttaaatt   120
gttgggtgcg gaagagaaag aatattatgt agaaggaggt aaagtaagga ggtggtttta   180
ggttagttag tatttttttg atattaggg                                     209
```

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Forward primer used to amplify the unconverted EGFR exon 19 gene locus SEQ ID NO:21

<400> SEQUENCE: 19

```
tctctgtcat agggactctg gatc                                           24
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Reverse primer used to amplify the unconverted EGFR exon 19 gene locus SEQ ID NO:21

<400> SEQUENCE: 20

```
cctgaggttc agagccatgg a                                              21
```

<210> SEQ ID NO 21
<211> LENGTH: 159
<212> TYPE: DNA
<213> ORGANISM: Homo sapiens
<220> FEATURE:
<223> OTHER INFORMATION: Unconverted EGFR exon 19 gene locus

<400> SEQUENCE: 21

```
tctctgtcat agggactctg gatcccagaa ggtgagaaag ttaaaattcc cgtcgctatc    60
aaggaattaa gagaagcaac atctccgaaa gccaacaagg aaatcctcga tgtgagtttc   120
tgctttgctg tgtgggggtc catggctctg aacctcagg                          159
```

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Forward primer used to amplify the bisulfite-converted EGFR exon 19 gene locus SEQ ID NO:24

<400> SEQUENCE: 22

```
tttttttgtta tagggatttt ggattt                                        26
```

<210> SEQ ID NO 23
<211> LENGTH: 27
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer used to amplify the bisulfite-
      converted EGFR exon 19 gene locus SEQ ID NO:24

<400> SEQUENCE: 23
taaacctaaa attcaaaacc ataaacc                                        27

<210> SEQ ID NO 24
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Bisulfite-converted EGFR exon 19 gene locus
      (bisulfite strand I) derived from SEQ ID NO:21

<400> SEQUENCE: 24 tttttgtta tagggatttt ggattttaga aggtgagaaa gttaaaattt tcgtcgttat      60
taaggaatta agagaagtaa tattttcgaa agttaataag gaaattttcg atgtgagttt    120
ttgttttgtt gtgtggggt ttatggtttt gaattttagg ttta                     164

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer used to amplify the unconverted
      KRAS exon 4 gene locus SEQ ID NO:27

<400> SEQUENCE: 25
gagagaaaaa ctgatatatt aaatgaca                                       28

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer used to amplify the unconverted
      KRAS exon 4 gene locus SEQ ID NO:27

<400> SEQUENCE: 26
tttgccttct agaacagtag acaca                                          25

<210> SEQ ID NO 27
<211> LENGTH: 178
<212> TYPE: DNA
<213> ORGANISM: Homo sapiens
<220> FEATURE:
<223> OTHER INFORMATION: Unconverted KRAS exon 4 gene locus

<400> SEQUENCE: 27
gagagaaaaa ctgatatatt aaatgacata acagttatga ttttgcagaa aacagatctg     60
tatttatttc agtgttactt acctgtcttg tctttgctga tgtttcaata aaaggaattc    120
cataacttct tgctaagtcc tgagcctgtt ttgtgtctac tgttctagaa ggcaaatc     178

<210> SEQ ID NO 28
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Bisulfite-converted KRAS exon 4 gene locus
      (bisulfite strand I) derived from SEQ ID NO:27

<400> SEQUENCE: 28
gagagaaaaa ttgatatatt aaatgatata atagttatga ttttgtagaa aatagatttg    60
tatttatttt agtgttattt atttgttttg ttttgttga tgttttaata aaggaattt    120 tataatttt tgttaagttt tgagtttgtt ttgtgtttat tgttttagaa ggtaaa        176

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer used to amplify the bisulfite-
      converted KRAS exon 4 gene locus SEQ ID NO:28

<400> SEQUENCE: 29
gagagaaaaa ttgatatatt aaatgata                                       28

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer used to amplify the bisulfite-
      converted KRAS exon 4 gene locus SEQ ID NO:28

<400> SEQUENCE: 30
tttaccttct aaaacaataa acaca                                          25

<210> SEQ ID NO 31
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Bisulfite-converted KRAS exon 4 gene locus
      (bisulfite strand II) derived from SEQ ID NO:27

<400> SEQUENCE: 31
gatttgtttt ttagaatagt agatataaaa taggtttagg atttagtaag aagttatgga    60
atttttttta ttgaaatatt agtaaagata agataggtaa gtaatattga aataaatata   120
gatttgtttt ttgtaaaatt ataattgtta tgttatttaa tatattag                168

<210> SEQ ID NO 32
<211> LENGTH: 26
<212> TYPE: DNA
<213> ORGANISM: Artificial Sequence
<220> FEATURE:

<223> OTHER INFORMATION: Description of Artificial Sequence: Synthetic
       oligonucleotide
<220> FEATURE:
<223> OTHER INFORMATION: Forward primer used to amplify the bisulfite-
       converted KRAS exon 4 gene locus SEQ ID NO:31

<400> SEQUENCE: 32
gatttgtttt ttagaatagt agatat                                          26

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Reverse primer used to amplify the bisulfite-
       converted KRAS exon 4 gene locus SEQ ID NO:31

<400> SEQUENCE: 33
ctaatatatt aaataacata acaattata                                       29

<210> SEQ ID NO 34
<211> LENGTH: 477
<212> TYPE: DNA
<213> ORGANISM: Homo sapiens
<220> FEATURE:
<223> OTHER INFORMATION: BRCA2 region of interest (ROI) 1

<400> SEQUENCE: 34
tatgccttaa caaaagtaat ccatagtcaa gatcttaagc attttttcc ttatgatctt        60 taactgttct gggtcacaaa tttgtctgtc actggttaaa actaaggtgg gatttttttt      120
ttaaatagat ttaggaccaa taagtcttaa ttggtttgaa gaactttctt cagaagctcc      180
accctataat tctgaacctg cagaagaatc tgaacataaa acaacaatt acgaaccaaa       240 cctatttaaa actccacaaa ggaaaccatc ttataatcag ctggcttcaa ctccaataat      300
attcaaagag caagggctga ctctgccgct gtaccaatct cctgtaaaag aattagataa      360
attcaaatta gacttaggta agtaatgcaa tatggtagac tggggagaac tacaaactag      420
gaatttaggc aaacctgtgt taaaatctta gctcattcat taattgtgtc atgctgg        477

<210> SEQ ID NO 35
<211> LENGTH: 555
<212> TYPE: DNA
<213> ORGANISM: Homo sapiens
<220> FEATURE:
<223> OTHER INFORMATION: BRCA2 region of interest (ROI) 2

<400> SEQUENCE: 35
tcttagaata ctagaaatgt aataaaaat aaaacttaac aatttccccc tttttttacc        60
cccagtggta tgtgggagtt tgtttcatac accaaagttt gtgaaggtaa atattctacc      120
tggtttattt ttatgactta gtaattgaga atttgacaat agcgttatac ctttgccctg      180
agatttacaa atctgtacct agcattctgc ctcatacagg caattcagta aacgttaagt      240
gaaataaaga gtgaatgaaa aataatatc cttaatgatc agggcatttc tataaaaaat       300
aaactatttt ctttcctccc agggtcgtca gacaccaaaa catatttctg aaagtctagg      360
agctgaggtg gatcctgata tgtcttggtc aagttcttta gctacaccac ccacccttag     420
ttctactgtg ctcataggta ataatagcaa atgtgtattt acaagaaaga gcagatgagg     480
ttgataattg tcatctctaa tacttctgtt aaaaggaaat atgaaaagaa aatattagat    540
aatgtctttg ataag                                                    555

<210> SEQ ID NO 36
<211> LENGTH: 212
<212> TYPE: DNA
<213> ORGANISM: Homo sapiens
<220> FEATURE:
<223> OTHER INFORMATION: BRCA2 region of interest (ROI) 3

<400> SEQUENCE: 36
tgtctgacaa aaataagtt tttgcattct agtgataata tacaatacac ataaatttt      60 atcttacagt cagaaatgaa gaagcatctg aaactgtatt tcctcatgat actactgctg   120
taagtaaata tgacattgat tagactgttg aaattgctaa caatttttgga atgccttgtt  180 aaattattta tcttacattt ttaatttcct aa                                 212

<210> SEQ ID NO 37
<211> LENGTH: 216
<212> TYPE: DNA
<213> ORGANISM: Homo sapiens
<220> FEATURE:
<223> OTHER INFORMATION: BRCA2 region of interest (ROI) 4

<400> SEQUENCE: 37
actataattt ttgcagaatg tgaaaagcta ttttttccaat catgatgaaa gtctgaagaa   60
aaatgataga tttatcgctt ctgtgacaga cagtgaaaac acaaatcaaa gagaagctgc   120
aagtcatggt aagtcctctg tttagttgaa ctacaggttt ttttgttgtt gttgttttga   180
tttttttttt ttgaggtgga gtcttgctct gtcacc                            216

<210> SEQ ID NO 38
<211> LENGTH: 1199
<212> TYPE: DNA
<213> ORGANISM: Homo sapiens
<220> FEATURE:
<223> OTHER INFORMATION: BRCA2 region of interest (ROI) 5

<400> SEQUENCE: 38
gttgtgagaa taatataaat tatatggctt ataaaatatt aatgtgcttc tgttttatac     60
tttaacagga tttggaaaaa catcagggaa ttcatttaaa gtaaatagct gcaaagacca   120
cattggaaag tcaatgccaa atgtcctaga agatgaagta tatgaaacag ttgtagatac   180
ctctgaagaa gatagttttt cattatgttt ttctaaatgt agaacaaaaa atctacaaaa   240
agtaagaact agcaagacta ggaaaaaaat tttccatgaa gcaaacgctg atgaatgtga   300
aaaatctaaa aaccaagtga agaaaaata ctcatttgta tctgaagtgg aaccaaatga    360
tactgatcca ttagattcaa atgtagcaaa tcagaagccc tttgagagtg aagtgacaa    420 aatctccaag gaagttgtac cgtctttggc ctgtgaatgg tctcaactaa cccttttcagg  480 tctaaatgga gcccagatgg agaaaatacc cctattgcat atttcttcat gtgaccaaaa   540
tatttcagaa aaagacctat tagacacaga gaacaaaaga aagaaagatt tcttacttc   600 agagaattct ttgccacgta tttctagcct accaaaaatca gagaagccat taaatgagga   660
aacagtggta aataagagag atgaagagca gcatcttgaa tctcatacag actgcattct  720
tgcagtaaag caggcaatat ctggaacttc tccagtggct tcttcatttc agggtatcaa  780
aaagtctata ttcagaataa gagaatcacc taaagagact ttcaatgcaa gttttttcagg  840 tcatatgact gatccaaact ttaaaaaaga aactgaagcc tctgaaagtg gactggaaat  900

```
acatactgtt tgctcacaga aggaggactc cttatgtcca aatttaattg ataatggaag    960
ctggccagcc accaccacac agaattctgt agctttgaag aatgcaggtt taatatccac   1020
tttgaaaaag aaaacaaata agtttattta tgctatacat gatgaaacat cttataaagg   1080
aaaaaaaata ccgaaagacc aaaaatcaga actaattaac tgttcagccc agtttgaagc   1140
aaatgctttt gaagcaccac ttacatttgc aaatgctgat tcaggtacct ctgtcttttt   1199
```

<210> SEQ ID NO 39
<211> LENGTH: 4944
<212> TYPE: DNA
<213> ORGANISM: Homo sapiens
<220> FEATURE:
<223> OTHER INFORMATION: BRCA2 region of interest (ROI) 6, preferred
      for methylation analyses

<400> SEQUENCE: 39

```
ttttatgttt aggtttattg cattcttctg tgaaagaag ctgttcacag aatgattctg      60
aagaaccaac tttgtcctta actagctctt ttgggacaat tctgaggaaa tgttctagaa    120
atgaaacatg ttctaataat acagtaatct ctcaggatct tgattataaa gaagcaaaat    180
gtaataagga aaaactacag ttatttatta ccccagaagc tgattctctg tcatgcctgc    240
aggaaggaca gtgtgaaaat gatccaaaaa gcaaaaaagt ttcagatata aagaagagg     300 tcttggctgc agcatgtcac ccagtacaac attcaaaagt ggaatacagt gatactgact    360
ttcaatccca gaaaagtctt ttatatgatc atgaaaatgc cagcactctt attttaactc    420
ctacttccaa ggatgttctg tcaaacctag tcatgatttc tagaggcaaa gaatcataca    480
aaatgtcaga caagctcaaa ggtaacaatt atgaatctga tgttgaatta accaaaaata    540
ttcccatgga aaagaatcaa gatgtatgtg ctttaaatga aaattataaa acgttgagc     600 tgttgccacc tgaaaaatac atgagagtag catcaccttc aagaaggta caattcaacc    660 aaaacacaaa tctaagagta atccaaaaaa atcaagaaga aactacttca atttcaaaaa    720
taactgtcaa tccagactct gaagaacttt tctcagacaa tgagaataat tttgtcttcc    780
aagtagctaa tgaaaggaat aatcttgctt taggaaatac taaggaactt catgaaacag    840
acttgacttg tgtaaacgaa cccatttttca agaactctac catggtttta tatggagaca    900
caggtgataa acaagcaacc caagtgtcaa ttaaaagaa tttggtttat gttcttgcag    960
aggagaacaa aaatagtgta aagcagcata taaaaatgac tctaggtcaa gatttaaaat   1020
cggacatctc cttgaatata gataaaatac cagaaaaaaa taatgattac atgaacaaat   1080
gggcaggact cttaggtcca atttcaaatc acagttttgg aggtagcttc agaacagctt   1140
caaataagga aatcaagctc tctgaacata cattaagaa gagcaaaatg ttcttcaaag   1200
atattgaaga acaatatcct actagtttag cttgtgttga aattgtaaat accttggcat   1260
tagataatca aaagaaactg agcaagcctc agtcaattaa tactgtatct gcacatttac   1320
agagtagtgt agttgtttct gattgtaaaa atagtcatat aaccccctcag atgttatttt   1380 ccaagcagga tttaattca aaccataatt taacacctag ccaaaaggca gaaattacag   1440
aactttctac tatattagaa gaatcaggaa gtcagtttga atttactcag tttagaaaac   1500
caagctacat attgcagaag agtacatttg aagtgcctga aaaccagatg actatcttaa   1560
agaccacttc tgaggaatgc agagatgctg atcttcatgt cataatgaat gccccatcga   1620
ttggtcaggt agacagcagc aagcaatttg aaggtacagt tgaaattaaa cggaagtttg   1680
ctggcctgtt gaaaaatgac tgtaacaaaa gtgcttctgg ttatttaaca gatgaaaatg   1740
```

```
aagtggggtt tagggcttt tattctgctc atggcacaaa actgaatgtt tctactgaag    1800
ctctgcaaaa agctgtgaaa ctgtttagtg atattgagaa tattagtgag gaaacttctg    1860
cagaggtaca tccaataagt ttatcttcaa gtaaatgtca tgattctgtt gtttcaatgt    1920
ttaagataga aaatcataat gataaaactg taagtgaaaa aataataaa tgccaactga    1980 tattacaaaa taatattgaa atgactactg gcacttttgt tgaagaaatt actgaaaatt    2040
acaagagaaa tactgaaaat gaagataaca aatatactgc tgccagtaga aattctcata    2100
acttagaatt tgatggcagt gattcaagta aaaatgatac tgtttgtatt cataaagatg    2160
aaacggactt gctatttact gatcagcaca acatatgtct taaattatct ggccagttta    2220
tgaaggaggg aaacactcag attaaagaag atttgtcaga tttaactttt ttggaagttg    2280
cgaaagctca agaagcatgt catggtaata cttcaaataa agaacagtta actgctacta    2340
aaacggagca aaatataaaa gattttgaga cttctgatac atttttcag actgcaagtg    2400 ggaaaaatat tagtgtcgcc aaagagtcat ttaataaaat tgtaaatttc tttgatcaga    2460
aaccagaaga attgcataac ttttccttaa attctgaatt acattctgac ataagaaaga    2520
acaaaatgga cattctaagt tatgaggaaa cagacatagt taaacacaaa atactgaaag    2580
aaagtgtccc agttggtact ggaaatcaac tagtgacctt ccaggacaa cccgaacgtg    2640 atgaaaagat caaagaacct actctattgg gttttcatac agctagcggg aaaaaagtta    2700
aaattgcaaa ggaatctttg gacaaagtga aaaacctttt tgatgaaaaa gagcaaggta    2760
ctagtgaaat caccagtttt agccatcaat gggcaaagac cctaaagtac agagaggcct    2820
gtaaagacct tgaattagca tgtgagacca ttgagatcac agctgcccca aagtgtaaag    2880
aaatgcagaa ttctctcaat aatgataaaa accttgtttc tattgagact gtggtgccac    2940
ctaagctctt aagtgataat ttatgtagac aaactgaaaa tctcaaaaca tcaaaaagta    3000 tcttttgaa agttaaagta catgaaaatg tagaaaaaga aacagcaaaa agtcctgcaa    3060
cttgttacac aaatcagtcc ccttattcag tcattgaaaa ttcagcctta gcttttaca    3120 caagttgtag tagaaaaact tctgtgagtc agacttcatt acttgaagca aaaaatggc    3180 ttagagaagg aatatttgat ggtcaaccag aaagaataaa tactgcagat tatgtaggaa    3240
attatttgta tgaaaataat tcaaacagta ctatagctga aaatgacaaa aatcatctct    3300
ccgaaaaaca agatacttat ttaagtaaca gtagcatgtc taacagctat tcctaccatt    3360
ctgatgaggt atataatgat tcaggatatc tctcaaaaaa taaacttgat tctggtattg    3420
agccagtatt gaagaatgtt gaagatcaaa aaaacactag tttttccaaa gtaatatcca    3480
atgtaaaaga tgcaaatgca tacccacaaa ctgtaaatga agatatttgc gttgaggaac    3540
ttgtgactag ctcttcaccc tgcaaaaata aaaatgcagc cattaaattg tccatatcta    3600
atagtaataa ttttgaggta gggccacctg catttaggat agccagtggt aaaatcgttt    3660
gtgtttcaca tgaaacaatt aaaaagtga agacatatt tacagacagt ttcagtaaag    3720
taattaagga aaacaacgag aataaatcaa aatttgcca acgaaaatt atggcaggtt    3780 gttacgaggc attggatgat tcagaggata ttcttcataa ctctctagat aatgatgaat    3840
gtagcacgca ttcacataag gttttttgctg acattcagg tgaagaaatt ttacaacata    3900
accaaaatat gtctggattg gagaaagttt ctaaatatc accttgtgat gttagtttgg    3960
aaacttcaga tatatgtaaa tgtagtatag ggaagcttca taagtcagtc tcatctgcaa    4020
atacttgtgg gattttagc acagcaagtg gaaaatctgt ccaggtatca gatgcttcat    4080
tacaaaacgc aagacaagtg ttttctgaaa tagaagatag taccaagcaa gtcttttcca    4140
```

```
aagtattgtt taaaagtaac gaacattcag accagctcac aagagaagaa aatactgcta    4200
tacgtactcc agaacattta atatcccaaa aaggcttttc atataatgtg gtaaattcat    4260
ctgctttctc tggatttagt acagcaagtg gaaagcaagt ttccatttta gaaagttcct    4320
tacacaaagt taagggagtg ttagaggaat ttgatttaat cagaactgag catagtcttc    4380
actattcacc tacgtctaga caaaatgtat caaaaatact tcctcgtgtt gataagagaa    4440
acccagagca ctgtgtaaac tcagaaatgg aaaaaacctg cagtaaagaa tttaaattat    4500
caaataactt aaatgttgaa ggtggttctt cagaaaataa tcactctatt aaagtttctc    4560
catatctctc tcaatttcaa caagacaaac aacagttggt attaggaacc aaagtgtcac    4620
ttgttgagaa cattcatgtt ttgggaaaag aacaggcttc acctaaaaac gtaaaaatgg    4680
aaattggtaa aactgaaact ttttctgatg ttcctgtgaa aacaaatata gaagtttgtt    4740
ctacttactc caaagattca gaaaactact ttgaaacaga agcagtagaa attgctaaag    4800
cttttatgga agatgatgaa ctgacagatt ctaaactgcc aagtcatgcc acacattctc    4860
tttttacatg tcccgaaaat gaggaaatgg ttttgtcaaa ttcaagaatt ggaaaaagaa    4920
gaggagagcc ccttatctta gtgg                                           4944

<210> SEQ ID NO 40
<211> LENGTH: 498
<212> TYPE: DNA
<213> ORGANISM: Homo sapiens
<220> FEATURE:
<223> OTHER INFORMATION: BRCA2 region of interest (ROI) 7

<400> SEQUENCE: 40
atttatatgt gtactagtca ataaacttat atattttctc cccattgcag cacaactaag      60
gaacgtcaag agatacagaa tccaaatttt accgcacctg gtcaagaatt tctgtctaaa     120
tctcatttgt atgaacatct gactttggaa aaatcttcaa gcaatttagc agtttcagga     180
catccatttt atcaagtttc tgctacaaga aatgaaaaaa tgagacactt gattactaca     240
ggcagaccaa ccaaagtctt tgttccacct tttaaaacta atcacatttt tcacagagtt     300
gaacagtgtg ttaggaatat taacttggag gaaaacagac aaaagcaaaa cattgatgga     360
catggctctg atgatagtaa aaataagatt aatgacaatg agattcatca gtttaacaaa     420
aacaactcca atcaagcagt agctgtaact ttcacaaagt gtgaagaaga acctttaggt     480
attgtatgac aatttgtg                                                  498

<210> SEQ ID NO 41
<211> LENGTH: 271
<212> TYPE: DNA
<213> ORGANISM: Homo sapiens
<220> FEATURE:
<223> OTHER INFORMATION: BRCA2 region of interest (ROI) 8

<400> SEQUENCE: 41
aaatatgcat ttttgttttc acttttagat atgatacgga aattgataga agcagaagat      60
cggctataaa aaagataatg gaagggatg acacagctgc aaaaacactt gttctctgtg      120
tttctgacat aatttcattg agcgcaaata tatctgaaac ttctagcaat aaaactagta     180
gtgcagatac ccaaaaagtg gccattattg aacttacaga tgggtggtat gctgttaagg     240
cccagttaga tcctccccctc ttagctgtct t                                   271

<210> SEQ ID NO 42
```

```
<211> LENGTH: 444
<212> TYPE: DNA
<213> ORGANISM: Homo sapiens
<220> FEATURE:
<223> OTHER INFORMATION: BRCA2 region of interest (ROI) 9

<400> SEQUENCE: 42
ccatggaatc tgctgaacaa aaggaacaag gtttatcaag ggatgtcaca accgtgtgga      60
agttgcgtat tgtaagctat tcaaaaaaag aaaaagattc aggtaagtat gtaaatgctt    120 tgttttatc agttttatta acttaaaaaa tgaccttact aacaaaatga ttataaatcc     180
agataaagta taaagttagt ttatatcaga gaagcaaaat ccactactaa tgcccacaaa    240
gagataatat aaaagaggat ctgtatttat tttgaaacaa acatttaaat gataatcact    300
tcttccattg catctttctc atctttctcc aaacagttat actgagtatt tggcgtccat    360
catcagattt atattctctg ttaacagaag gaaagagata cagaatttat catcttgcaa    420
cttcaaaatc taaagtaaa tctg                                            444

<210> SEQ ID NO 43
<211> LENGTH: 138
<212> TYPE: DNA
<213> ORGANISM: Homo sapiens
<220> FEATURE:
<223> OTHER INFORMATION: BRCA2 region of interest (ROI) 10

<400> SEQUENCE: 43
catctaacac atctataata acattctttt cttttttttc cattctagga cttgcccctt     60
tcgtctattt gtcagacgaa tgttacaatt tactggcaat aaagttttgg atagaccta    120 atgaggacat tattaagc                                                 138

<210> SEQ ID NO 44
<211> LENGTH: 252
<212> TYPE: DNA
<213> ORGANISM: Homo sapiens
<220> FEATURE:
<223> OTHER INFORMATION: BRCA2 region of interest (ROI) 11

<400> SEQUENCE: 44
gtgggtttgc aatttataaa gcagcttttc cacttatttt cttagaatat tgacatactt     60
tgcaatgaag cagaaaacaa gcttatgcat atactgcatg caaatgatcc caagtggtcc    120
accccaacta aagactgtac ttcagggccg tacactgctc aaatcattcc tggtacagga    180
aacaagcttc tggtaagtta atgtaaactc aaggaatatt ataagaagta tatatggagg    240
ccatcgtata tt                                                       252

<210> SEQ ID NO 45
<211> LENGTH: 366
<212> TYPE: DNA
<213> ORGANISM: Homo sapiens
<220> FEATURE:
<223> OTHER INFORMATION: BRCA2 region of interest (ROI) 12

<400> SEQUENCE: 45
ttactacata attatgatag gctacgtttt cattttttta tcagatgtct tctcctaatt     60
gtgagatata ttatcaaagt cctttatcac tttgtatggc caaaaggaag tctgtttcca    120
cacctgtctc agcccagatg acttcaaagt cttgtaaagg ggagaaagag attgatgacc    180
aaaagaactg caaaaagaga agagccttgg atttcttgag tagactgcct ttacctccac    240
ctgttagtcc catttgtaca tttgtttctc cggctgcaca gaaggcattt cagccaccaa    300
```

```
ggagttgtgg caccaaatac gaaacaccca taaagaaaaa agaactgaat tctcctcaga    360
tgactc                                                              366

<210> SEQ ID NO 46
<211> LENGTH: 337
<212> TYPE: DNA
<213> ORGANISM: Homo sapiens
<220> FEATURE:
<223> OTHER INFORMATION: BRCA1 region of interest (ROI) 1

<400> SEQUENCE: 46
aggagctccc agggcctgga aaggccactt tgtaagctca ttcttggggt cctgtggctc     60
tgtacctgtg gctggctgca gtcagtagtg gctgtggggg atctggggta tcaggtaggt    120
gtccagctcc tggcactggt agagtgctac actgtccaac cccactctc gggtcaccac     180 aggtgcctca cacatctgcc caattgctgg agacagagaa cacaagcaga gattagtgtc    240
aattcattct cctggactag gctctaatca atcgactcca gggtcctggt tgtatgagtt    300
cttaggatta atgaggtaga agctaatttt ttttttt                             337

<210> SEQ ID NO 47
<211> LENGTH: 278
<212> TYPE: DNA
<213> ORGANISM: Homo sapiens
<220> FEATURE:
<223> OTHER INFORMATION: BRCA1 region of interest (ROI) 2

<400> SEQUENCE: 47
tgtgcagttc tcaaatcctt acccatccct tacagatgga gtcttttggc acaggtatgt     60
gggcagagaa gacttctgag gctacagtag gggcatccat agggactgac aggtgccagt    120
cttgctcaca ggagagaata ttgtgtcctc cctctctgac agggcaccca atacttactg    180
tgccaagggt gaatgatgaa agctccttca ccacagaagc accacacagc tgtaccatcc    240
attccagttg atctaaaatg gacatttaga tgtaaaat                            278

<210> SEQ ID NO 48
<211> LENGTH: 150
<212> TYPE: DNA
<213> ORGANISM: Homo sapiens
<220> FEATURE:
<223> OTHER INFORMATION: BRCA1 region of interest (ROI) 3

<400> SEQUENCE: 48
tgcttataat actccactat gtaagacaaa ggctggtgct ggaactctgg ggttctccca     60
ggctcttacc tgtgggcatg ttggtgaagg gcccatagca acagatttct agcccctga    120 agatctggaa gaagagagga agagagaggg                                     150

<210> SEQ ID NO 49
<211> LENGTH: 128
<212> TYPE: DNA
<213> ORGANISM: Homo sapiens
<220> FEATURE:
<223> OTHER INFORMATION: BRCA1 region of interest (ROI) 4

<400> SEQUENCE: 49
aaggggagtg gaatacagag tggtggggtg agattttttgt caacttgagg gagggagctt    60
tacctttctg tcctgggatt ctcttgctcg ctttggacct tggtggtttc ttccattgac    120
cacatctc                                                            128
```

<210> SEQ ID NO 50
<211> LENGTH: 704
<212> TYPE: DNA
<213> ORGANISM: Homo sapiens
<220> FEATURE:
<223> OTHER INFORMATION: BRCA1 region of interest (ROI) 5

<400> SEQUENCE: 50

```
atatgactga atgaatatct ctggttagtt tgtaacatca agtacttacc tcattcagca    60
tttttctttc tttaatagac tgggtcaccc ctaaagagat catagaaaag acaggttaca   120
tacagcagaa gaacgtgctc ttttcacgga gatagagagg tcagcgattc acaaaagagc   180
acaggaagaa tgacagagga gaggtccttc cctctaaagc cacagccctt taataaggct   240
tgtagcagca gtttccttct ggagacagag ttgatgttta atttaaacat tataagtttg   300
cctgctgcac atggattcct gccgactatt aaataaatcc ctagctcata tgctaacatt   360
gctaggagca gattaggtcc tattagttat aaaagagacc cattttccca gcatcaccag   420
cttatctgaa caaagtgata ttaaagataa aagtagttta gtattacaat taaagacctt   480
ttggtaactc agactcagca tcagcaaaaa ccttaggtgt taaacgttag gtgtaaaaat   540
gcaattctga ggtgttaaag ggaggagggg agaaatagta ttatacttac agaaatagct   600
aactacccat tttcctcccg caattcctag aaaatatttc agtgtccgtt cacacacaaa   660
ctcagcatct gcagaatgaa aaacactcaa aggattagaa gttg                    704
```

<210> SEQ ID NO 51
<211> LENGTH: 243
<212> TYPE: DNA
<213> ORGANISM: Homo sapiens
<220> FEATURE:
<223> OTHER INFORMATION: BRCA1 region of interest (ROI) 6

<400> SEQUENCE: 51

```
tacaggcatg cgccaccgtg cctcgcctca tgtggtttta tgcagcagat gcaaggtatt    60
ctgtaaaggt tcttggtata cctgttttca taacaacatg agtagtctct tcagtaatta   120
gattagttaa agtgatgtgg tgtttttctgg caaacttgta cacgagcatc tgaaattaaa   180
tcaaatattc cattatcatg agttacctct agcacacagc tcagaatact agttattcca   240
cca                                                                  243
```

<210> SEQ ID NO 52
<211> LENGTH: 306
<212> TYPE: DNA
<213> ORGANISM: Homo sapiens
<220> FEATURE:
<223> OTHER INFORMATION: BRCA1 region of interest (ROI) 7

<400> SEQUENCE: 52

```
acctacataa aactctttcc agaatgttgt taagtcttag tcattaggga gatacatatg    60
gatacactca caaattcttc tggggtcagg ccagacacca ccatggacat tcttttgttg   120
acccttttctg ttgaagctgt caattctggc ttctccctgc tcacactttc ttccattgca   180
ttatacccag cagtatcagt agtatgagca gcagctggac tctgggcaga ttctgcaact   240
ttcaattggg gaactttcaa tgcagaggtt gaagatggta tgttgccaac acgagctgac   300
tctggg                                                              306
```

<210> SEQ ID NO 53
<211> LENGTH: 346

```
<212> TYPE: DNA
<213> ORGANISM: Homo sapiens
<220> FEATURE:
<223> OTHER INFORMATION: BRCA1 region of interest (ROI) 8

<400> SEQUENCE: 53
ttaagtataa caaaagtgtc catgatagac tagtacatct aaaagttggt taaccagaat      60
atctttatgt aggattcaga gtaaaatcaa agtgtttgtt ccaatacagc agatgaaata     120
ttacctagat cttgccttgg caagtaagat gtttccgtca atcgtgtgg cccagactct      180 tccagctgtt gctcctccac atcaacaacc ttaatgagct cctcttgaga tgggtagttt     240
ctattctgaa gactcccaga gcaactgtgc atgtaccacc tatcatctaa tgatgggcat     300
ttagaagggg atgacctaga agataaatg gaaggagaaa accatc                     346

<210> SEQ ID NO 54
<211> LENGTH: 386
<212> TYPE: DNA
<213> ORGANISM: Homo sapiens
<220> FEATURE:
<223> OTHER INFORMATION: BRCA1 region of interest (ROI) 9

<400> SEQUENCE: 54
tcatgttgta gcttatgtta taggttcaaa aaacctatat aggattaaac aaaagaagta      60
tcctagagca ataaaagtgt ataaatgcct gtatgcaaaa aactggagaa agtatggtga     120
aaaaaattaa caatcagagt tcaatataaa taaagatgtc agataccaca gcatctttac     180
attgatgttt cttaccttc cactcctggt tctttatttt tactggtaga actatctgca      240
gacacctcaa acttgtcagc agaaaggcct tctggattct ggcttatagg gtattcacta     300
cttttctgtg aagttaatac tgctttaaat ggaatgagaa acaaatcta ctttactgct      360 ttgttctgat agtgataatt caggtt                                          386

<210> SEQ ID NO 55
<211> LENGTH: 262
<212> TYPE: DNA
<213> ORGANISM: Homo sapiens
<220> FEATURE:
<223> OTHER INFORMATION: BRCA1 region of interest (ROI) 10

<400> SEQUENCE: 55
taggtcctta ctcttcagaa ggagataaag gggaaggaaa gaattttgct taagatatca      60
gtgtttggcc aacaatacac acctttttct gatgtgcttt gttctggatt tcgcaggtcc     120
tcaagggcag aagagtcact tatgatggaa gggtagctgt tagaaggctg gctcccatgc     180
tgttctaaca cagcttctag ttcagccatt tcctgctgga gctttatcag gttatgttgc     240
atggtatccc tctgcttcaa aa                                              262

<210> SEQ ID NO 56
<211> LENGTH: 3899
<212> TYPE: DNA
<213> ORGANISM: Homo sapiens
<220> FEATURE:
<223> OTHER INFORMATION: BRCA1 region of interest (ROI) 11, preferred
      for mutation analyses

<400> SEQUENCE: 56
accacacaca cgcatgtgca cacacacaca cgcttttac ctgagtggtt aaaatgtcac       60
tctgagagga tagccctgag cagtcttcag agacgcttgt ttcactctca cacccagatg     120
ctgcttcacc ttaaataaca aaaacagagg ttcagatgta aaagcagact ataaacgctg     180
```

```
caacttgctg tgtcttttc ttctcattgg caggactgga tttactttca tgtcacacaa    240
aatgattaaa ttccttgctt tgggacacct ggatttgctt ttataaaatg aaaccagaag    300
taagtccacc agtaattagg atgttaaagc tcattcagtc aaagatgacg tcctagctgt    360
gtgaaggact tttttctatg aaaagcacct taggaggaac atgtttcaag tttaagaagc    420 agttcccttta actatacttg gaaatttgta aaatgtgctc cccaaaagca taaacattta    480
gctcacttct ataaatagac tggggcaaac acaaaaacct ggttccaata cctaagtttg    540
aatccatgct ttgctcttct tgattatttt cttccaagcc cgttcctctt tcttcatcat    600
ctgaaaccaa ttccttgtca ctcagaccaa ctccctggct ttcagactga tgcctcattt    660
gtttggaaga accaatcaag aaaggatcct gggtgtttgt atttgcagtc aagtcttcca    720
attcactgca ctgtgaagaa acaagctag cagaacattt tgtttcctca ctaaggtgat    780
gttcctgaga tgcctttgcc aatattacct ggttactgca gtcatttaag ctattcttca    840
atgataataa attctcctct gtgttcttag acagacactc ggtagcaacg gtgctatgcc    900
tagtagactg agaaggtata ttgtttactt taccaaataa caagtgttgg aagcagggaa    960
gctcttcatc ctcactagat aagttctctt ctgaggactc taatttcttg gcccctcttc   1020
ggtaaccctg agccaaatgt gtatgggtga aagggctagg actcctgcta agctctcctt   1080
tctggacgct tttgctaaaa acagcagaac tttccttaat gtcatttta gcaaaactag   1140 tatcttcctt tatttcacca tcatctaaca ggtcatcagg tgtctcagaa caaacctgag   1200
atgcatgact acttcccata ggctgttcta agttatctga aatcagatat ggagagaaat   1260
ctgtattaac agtctgaact acttcttcat attcttgctt ttttatttca ggatgcttac   1320
aattacttcc aggaagactt tgtttataga cctcaggttg caaaaccct aatctaagca   1380 tagcattcaa ttttggccct ctgtttctac ctagttctgc ttgaatgttt tcatcactgg   1440
aacctatttc attaatactg gagcccactt cattagtact ggaacctact tcattaatat   1500
tgcttgagct ggcttcttta aaaacatttt ctctaatgtt attacggcta attgtgctca   1560
ctgtacttgg aatgttctca tttcccattt ctctttcagg tgacattgaa tgttcctcaa   1620
agttttcctc tagcagattt ttcttacatt tagttttaac aaatgacttg atgggaaaaa   1680
gtggtggtat acgatatggg ttttgtaaaa gtccatgttt atttggagta atgagtccag   1740
tttcgttgcc tctgaactga gatgatagac aaaacctaga gcctcctttg atactacatt   1800
tggcattatc aactggctta tctttctgac caaccacagg aaagcctgca gtgatattaa   1860
ctgtctgtac aggcttgata ttagactcat tctttccttg attttcttcc ttttgttcac   1920
attcaaaagt gacttttgga ctttgtttct ttaaggaccc agagtgggca gagaatgttg   1980
cacattcctc ttctgcattt cctggatttg aaaacggagc aaatgactgg cgctttgaaa   2040
ccttgaatgt attctgcaaa tactgagcat caagttcact ttcttccatt tctatgcttg   2100
tttcccgact gtggttaact tcatgtccca atggatactt aaagccttct gtgtcatttc   2160
tattatcttt ggaacaacca tgaattagtc ccttggggtt ttcaaatgct gcacactgac   2220
tcacacattt atttggttct gttttttgcct tccctagagt gctaacttcc agtaacgaga   2280
tactttcctg agtgccataa tcagtaccag gtaccaatga aatactgcta ctctctacag   2340
atctttcagt ttgcaaaacc ctttctccac ttaacatgag atctttgggg tcttcagcat   2400
tattagacac tttaactgtt tctagtttct cttctttttc ttctcttgga aggctaggat   2460 tgacaaaattc tttaagttca ctggtatttg aacacttagt aaaagaacca ggtgcatttg   2520
```

| | |
|---|---|
| ttaacttcag ctctgggaaa gtatcgctgt catgtcttt acttgtctgt tcatttggct | 2580 |
| tgttactctt cttggctcca gttgcaggtt ctttaccttc catgagttgt aggtttctgc | 2640 |
| tgtgcctgac tggcatttgg ttgtactttt ttttctttat ctcttcactg ctagaacaac | 2700 |
| tatcaatttg caattcagta caattaggtg ggcttagatt tctactgact actagttcaa | 2760 |
| gcgcatgaat atgcctggta gaagacttcc tcctcagcct attctttta ggtgcttttg | 2820 |
| aattgtggat atttaattcg agttccatat tgcttatact gctgcttata ggttcagctt | 2880 |
| tcgttttgaa agcagattct ttttcgagtg attctattgg gttaggattt ttctcattct | 2940 |
| gaatagaatc accttttgtt ttattctcat gaccactatt agtaatattc atcacttgac | 3000 |
| cattctgctc cgtttggtta gttccctgat ttatcatttc aggagtcttt tgaactgcca | 3060 |
| aatctgcttt cttgataaaa tcctcaggat gaaggcctga tgtaggtctc cttttacgct | 3120 |
| ttaatttatt tgtgagggga cgtcttgta ttatctgtgg ctcagtaaca aatgctccta | 3180 |
| taattagatt ttcagttaca tggcttaagt tggggaggct tgccttcttc cgataggttt | 3240 |
| tcccaaatat tttgtcttca atattactct ctactgattt ggagtgaact cttcacttt | 3300 |
| tacatattaa agcctcatga ggatcactgg ccagtaagtc tattttctct gaagaaccag | 3360 |
| aatattcatc tacctcattt agaacgtcca atacatcagc tactttggca tttgattcag | 3420 |
| actccccatc atgtgagtca tcagaaccta acagttcatc acttctggaa aaccactcat | 3480 |
| taactttctg aatgctgcta tttagtgtta tccaaggaac atcttcagta tctctaggat | 3540 |
| tctctgagca tggcagtttc tgcttattcc attctttct ctcacacagg ggatcagcat | 3600 |
| tcagatctac cttttttct gtgctgggag tccgcctatc attacatgtt tccttacttc | 3660 |
| cagcccatct gttatgttgg ctccttgcta agccaggctg tttgctttta ttacagaatt | 3720 |
| cagccttttc tacattcatt ctgtctttag tgagtaataa actgctgttc tcatgctgta | 3780 |
| atgagctggc atgagtattt gtgccacatg gctccacatg caagtttgaa acagaactac | 3840 |
| cctgatactt ttctggatgc ctctcagctg cacgcttctc agtggtgttc aaatcatta | 3899 |

<210> SEQ ID NO 57
<211> LENGTH: 1100
<212> TYPE: DNA
<213> ORGANISM: Homo sapiens
<220> FEATURE:
<223> OTHER INFORMATION: BRCA1 region of interest (ROI) 12

<400> SEQUENCE: 57

| | |
|---|---|
| accccgtctc tactaaaaat acaaaaatta gcctggcatg gtggcgcgtg cctgtaatcc | 60 |
| cagctactaa gggggctaag gcaggaggac tgcttctagc ctgggccaca gagcaagact | 120 |
| ccatctcaaa aaaaaaaaag aaaaaaaaaa gaaaagaaga agaagaagaa gaagaaaaca | 180 |
| aatggtttta ccaaggaagg attttcgggt tcactctgta gaagtctttt ggcacggttt | 240 |
| ctgtagccca ctttggat gatagaaact tcatcttta gatgttcagg agagttattt | 300 |
| tccttttttg caaaattata gctgtttgca tctgtaaaat acagggaaa acattatgtt | 360 |
| tgcagttaga gaaaaatgta tgaattataa tcaaagaaac caagagaaac cctatgtatg | 420 |
| ctctttgttg tgttaagaca atgcattaag gttacctgtg attttttta aaaatcaaat | 480 |
| tttaaaaaat caactggaaa ttttactcct aggaaacaaa aacaaataca cagaccatca | 540 |
| aagttattta gagtccttgt tttctacctt aacactaaga atttgccta tcaatactgt | 600 |
| atttcactaa agctaagaca ccaacaatgt aagttgcact attattttct gtatcactaa | 660 |
| gaaagaaagc acacaaatta aacaaatgac acaccctcaa tagtaaaatg ttcccaattt | 720 |

```
cagagatgtt aagatgtgaa aaatgtgcac cttacgattg ataaaataag gtgtgagacc    780
agtgggagta attttttaaa aatagattac agatacagaa ctaaaattaa cctagactaa    840
aaggtcttat caccacgtca tagaaagtaa ttgtgcaaac ttcctgagtt ttcatggaca    900
gcacttgagt gtcattcttg ggatattcaa cacttacact ccaaacctgt gtcaagctga    960
aaagcacaaa tgattttcaa tagctcttca acaagttgac taaatctcgt actttcttgt   1020
aggctcctga aattaaattg tttgagaaac acactcagca agtgattatc aacctttaa    1080 ggacactaaa ataagaaaag                                               1100
```

<210> SEQ ID NO 58
<211> LENGTH: 101
<212> TYPE: DNA
<213> ORGANISM: Homo sapiens
<220> FEATURE:
<223> OTHER INFORMATION: BRCA1 region of interest (ROI) 13

<400> SEQUENCE: 58

```
tcctactgtg gttgcttcca acctagcatc attaccaaat tatataccttt ttggttatat    60 cattcttaca taaaggacac tgtgaaggcc ctttcttctg g                         101
```

<210> SEQ ID NO 59
<211> LENGTH: 1229
<212> TYPE: DNA
<213> ORGANISM: Homo sapiens
<220> FEATURE:
<223> OTHER INFORMATION: BRCA1 region of interest (ROI) 14

<400> SEQUENCE: 59

```
tgtaaaacac cataaaaatt aatcttaagg ccgggcgcgg tggctcacgc ctgtaatccc     60
agcactttgg gaggccgagg tgggcggatc acgaggtcag gaagtggaga ccatcctggc    120
taacacggtg aaaccccgtc tctactaaaa atacaaaaaa ttagccgggc gtggtggtgg    180
gcgcctgtag tcccagctac ttgggggggcc gaggcaggag aatggcgtga acccgggagg    240
cggagcttgc agtgagccga gatggcgcca ctgcactccg gcctgggtga agagcgaga    300 ctccgtctca aaaacaaaac aaacaaaaat taatcttaag ccaggcgcag tggctcacgc    360
cagcactttg gaaggccgag gcgggtggat cacgagatca ggacttcaag accagcctga    420
ccaacgtgat gaaaccctat ctctactaaa aatacaaaat tagccggcca cggtggcgtg    480
cgcctataat cccagctact caggaggctg aggcaggaga agcgcttgaa cttgaacctg    540
gcaggcggag gttgcagtga gccaagatgg cgccactgca ctccagcctg ggcgacagag    600
ccagactcca accccccacc ccgaaaaaaa aaggtccagg ccgggcgcag tggctcagga    660
ctgtaatccc agcactttgg aaggctgagg cgggtggatc acaaggtcag gagatcgaga    720
ccatcttggc taacatggtg aaaccccgtc tctactaaaa atacaaaaaa ttagccgggc    780
atagtggtgg gcgcctgtag tcccagctac tcgggaggct gaggcaggag aatggcctga    840
acccgggagg cggagctggc agtgagccaa gatcgtgcca ctgcactcca gcctaggcag    900
cagagcgaga ccgtgtctca aaaaaacaaa acaaaacaaa acaaaaagtc tgggagcggt    960
ggctcacgcc tgtaatccca gcactttcgg aggccaaggc aggaggatca cctgaggtca   1020
ggagttcgag accaacctga ccaatatgga gaaaccctgt ctctactaaa aatacaaaat   1080
tagctggtgt gatggcacat gcctgcaatc ccagtactc cggaggctga ggcagcagaa   1140 ttgccttgaac ccgggaggtg gaggttgtag tgagccgaga ttgtgccact gcactccagc   1200
```

```
ctgggcaaca agagccaaag tctgtctca                                      1229

<210> SEQ ID NO 60
<211> LENGTH: 1369
<212> TYPE: DNA
<213> ORGANISM: Homo sapiens
<220> FEATURE:
<223> OTHER INFORMATION: BRCA1 region of interest (ROI) 15

<400> SEQUENCE: 60
agcatggcca acatagcaaa accctatctc tacaacagaa aaatacaaga atggctggac        60
gcagtggctt atgcctgtaa tcctagcact ttgggaggcc caggcgggtg gatcacaagg       120
tcaggagatc aagactatcc tggctaacac ggtgaaatcc cgcctctact aaaaaagaaa       180
aaaaaataca aaaaattagc cgggcgtggt agtgggtgct tgtagtccca gctattcagg       240
aggctcaggc agaagaatgg catgaacccg ggaggcagag tttgcagtga gctgagatcg       300
cgccactgca ctccagcctg ggcaacagag caagactcca tctcaaaaaa agaaaaaaaa       360
atacaaaaat tagctgggca tggtggtgca cacctatcgt ccctgctact ctggaggctg       420
aggtgggagg attgcttgag cctgacgagg ttgaggctgc agtgagctgt gatagcacca       480
ctgcactcca gcctctcgac agagatccta tataaaaaaa aaacctctgc atttcattgt       540
atgtaaataa gtatgtaatt tcattgtatg tacagagcca gtttcaaaca aaggttcttc       600
caaataccta tcctctcaac gacaccgatc atccatgttt tttttttttt ttttttttt       660 ttgagatgga gtttagctct gtcgctggag ttcagtggtg ccatattggc tcacagcaac       720
atctgcctcc tggttcaagt gattctcctg cctcagcctc ctgagtagct gggattacag       780
gcacatgcca ctacgcccag ctaattttg tattttagt ggagaggggg tttcaccatg        840
ttggccagga tggtctcgat ctcctgacct cgtgatccta ccaccttggc ctcccaaagt       900
gctgggatta caggcataag ccaccgccct cggcctcatc catgattta ttttgccatt        960 tcaagtgatg gagcttgttt tagagctgga agaaaagcca aaatgccagt taatctaaac      1020
tagattcctg ccccagtgca gaaccaatca agacagagtc cctgtctttc ccggaccaca      1080
ggatttgtgt tgaaaggag aggagtggga gaggcagagt ggatggagaa caaggaatca       1140
ttttctatat ttttaaagtt cttcagttaa gaaaatcagc aattacaata gcctaatctt      1200
actagacatg tcttttcttc cctagtatgt aaggtcaatt ctgttcattt gcataggaga      1260
taatcatagg aatcccaaat taatacactc ttgtgctgac ttaccagatg ggacactcta      1320
agattttctg catagcatta atgacatttt gtacttcttc aacgcgaag               1369

<210> SEQ ID NO 61
<211> LENGTH: 1308
<212> TYPE: DNA
<213> ORGANISM: Homo sapiens
<220> FEATURE:
<223> OTHER INFORMATION: BRCA1 region of interest (ROI) 16, preferred
      for methylation analyses

<400> SEQUENCE: 61
aatcaacaac gaccaaacca acaccaatca aggcctcccc gccctaacc tttcccagtg         60 acctgctctc atctctggat cctcctcaag cacatccctg ccggcagcat ctgttactac       120
tgacgctcct ctacttccct cttgcgcttt tcaatggcg caaatggatc cagttcttaa       180
gttctccctc ccacaaaatc ctgtctcctc cccttcccag acatattcct ggcacctctt      240
cttccacaag gtcccatcct ctcatacata ccagccggtg ttttttgttt tgttttgttt      300
```

```
tgttttgttt tgagacagtc tcgctctgtc gcccaggctg gagtgcaatg gcgcgatctc      360
ggctcactgc aacctccgcc tcccgggttc tagcgattct cctgcctcag cctcctgagt      420
agctggagcg gcaccacgcc cggctaattt ttgtattttt agtagagacg gagtttcacc      480
acgttggtca ggctggtctg gaactcctga cctcatgacc agccgacgtt tttaaagaca      540
tagtgtcccc ctcaaggcat attccagttc ctatcacgag gattccccca cggacactca      600
gtgccccctt cctgatcctc agcgcttccc tcgcgaccta caaactgccc cctccccag       660 ggttcacaac gccttacgcc tctcaggttc cgcccctacc ccccgtcaaa gaatacccat      720
ctgtcagctt cggaaatcca ctctcccacg ccagtacccc agagcatcac ttgggccccc      780
tgtccctttc ccgggactct actacccttta cccagagcag agggtgaagg cctcctgagc     840
gcagggcccc agttatctga gaaacccccac agcctgtccc ccgtccagga agtctcagcg     900
agctcacgcc gcgcagtcgc agttttaatt tatctgtaat tcccgcgctt ttccgttgcc      960
acggaaacca aggggctacc gctaagcagc agcctctcag aatacgaaat caaggtacaa      1020
tcagaggatg ggagggacag aaagagccaa gcgtctctcg gggctctgga ttggccaccc     1080
agtctgcccc cggatgacgt aaaaggaaag agacggaaga ggaagaattc tacctgagtt     1140
tgccataaag tgcctgccct ctagcctcta ctcttccagt tgcggcttat tgcatcacag     1200
taattgctgt acgaaggtca gaatcgctac ctattgtcca aagcagtcgt aagaagaggt     1260
cccaatcccc cactctttcc gccctaatgg aggtctccag tttcggta                  1308
```

<210> SEQ ID NO 62
<211> LENGTH: 1411
<212> TYPE: DNA
<213> ORGANISM: Homo sapiens
<220> FEATURE:
<223> OTHER INFORMATION: BRCA1 region of interest (ROI) 17

<400> SEQUENCE: 62

```
atgcgttgcg gaatgaaagg tcttcgccac agtgttcctt agaaactgta gtcttatgga       60
gaggaacatc caataccaga gcgggcacaa ttctcacgga aatccagtgg atagattgga      120
gacctgtgcg cgcttgtact tgtcaacagt tatggactgg agtgttatgt tttcgtattt      180
tgaaagcaga aactaggcct taaaaagata cgtacaactc tttagggaga ctacaattcc      240
catccagccc caggagtctg gggcaagtag tcttgtaagg tcagtggcct gcggggacgc      300
agtgagcgcc gaatttgcct ggggcagggg aaatgcgctc tgcccatgt ctgcgcactc       360 gtagttccac ccctcagccc cagtgttttgt tatttttcgg gttcagcttg cttttgcccc     420
gtctccgtcg acgcaatcgc caccagtcaa tggggtggtc gttttgaggg acaagtggta     480
agagccaatc ttcttggcga aaacgcggag aaacgggact agttactgtc tttgtccgcc     540
atgttagatt caccccacag agatagcggc agagctggca gcggacggtc tttgcattgc     600
cgcctcccca gggggcggga agctggtaag gaagcagcct gggttagcta ggggtggggt     660
cacgtcacac taagagggtt tggagaagtt caagggagga atcctgcaaa gaagaggggc     720 gacttttttcc gtgtctccgg acagctaatc gttttagtga caggatgaga gagcccttcg    780
tgttctgagg gaccgagtgg gcgaaaaagc ccggagagtt ggagagtctg tggttcagaa     840
tgcgaggtga caacgtgcta gcagccctcg ctcgctctcg gcgcctcctc ggccttggcg     900
tccattctgg ccgtgctgga ggagcccttc agcccgccac tgcgctgtgg gggcccctct    960
ctgggctggc cgaagccaga gccggctccc tctgcttgcg gggaagtgtg gagggagagg    1020 cggggtgtggg aactgggggct gcgcgcagcg ctcgccagcc agcgcgagtt ccaggtgggc   1080
```

```
gcgggctcag cgggccccgc accccggcc ccgggcagtc aggggcctag caccggggcc    1140
agcagctgca gagggtgcgc cgggtcccc agcactgccg gccgcctgc accccgcttg     1200 aattctcacc gggccccagc cgccctgcac agggcaaggc tcaggacctg cagcccgcca   1260
tgcccgagcc ccctcccaac ccctgtgagc tccagcgtgg cctgagcctc cccgacgggc   1320 accgcccct gctcctcagc gcccggtccc atcgactgcc aagggctga gaggagtgca     1380 ggcgcccggc acagccctgc gcaggatcca c                                  1411
```

<210> SEQ ID NO 63
<211> LENGTH: 2166
<212> TYPE: DNA
<213> ORGANISM: Homo sapiens
<220> FEATURE:
<223> OTHER INFORMATION: BRCA1 region of interest (ROI) 18

<400> SEQUENCE: 63

```
ggatcacgag gtcaagagat cgagaccatc ctggctaaca cagtgaaacc ccgactctac     60
taaaaagaca aaatattagc tgggtgcggt ggtgggtgcc tgtaatcccc tctactgggg    120
aggttgaggc aggagaatgg cgtgaacccg ggaggcggag cttgcagtga gcccagattg    180
caccactgca ttccagcctg ggtgacagag ggagactcca tctcaaaaaa aaaaaaaaaa    240
aaaaaaaaaa atgcaggctg cctgagccag cagcagcaac ccgctctggt ctccttccac    300
gctgtggaag cttttgttctt gtgctctttg caataaatct tgctgctgct cactctttgg   360
gtccgcatag catttatctg ctggtaacac cgaccgcaga ggtctgcagc ttcactcctg    420
aagccagcga gaccacgaac ccaccaggag gaatgaacaa ctccagacgg gaggaacgaa    480
caaactccag acatgccgcc ttaagagctg taacactcac cgcaaaggtc tgcagcttca    540
ctcctgaagc cagcgagacc acgaatccac cagaaggagg taactctgaa cacgtccgaa    600
catcagaagg aacaaactct ggacacatca tctttaagaa ctgtaccact caccgtgagg    660
gtccgcaact tcattcttga agtcagtgag accaagaacc caccaatttc ggacacaaga    720
acatccggct tctactgatg gaaggccacg actcctcagt agaaagaggg cccaggcaaa    780
gaaaatgaga gagagtcctt ggggtggtga cactatcttg ggaacatgga gtgctaggaa    840
acgataactg gaagactagg atgaaatctg caagttaaaa aatgacacta cccatatatc    900
cttctcatcc cattctcctt ttttcgagac cccgttaaag agatcttggt tagggacctt    960
tggttttgga aaggcactgt ttctcctttt tgtcaaacac tcaactttca ggccacactt   1020 ttttttttt tttcgagaca aagtctcgct ttctcaaaga ccagcccagg ctggtcttga   1080
actcctgagc tcaagcgatc ctcctgcctt ggcctcccaa agtgctggga ttacaggcat   1140
gagccaccac tccggcctc agcttggata acttggcttg tacaggcctc tggtggagac    1200
agtaaccaaa gttcgggttg ccaggtttgt ttcattaaag ggattttgtt gaggctgaaa   1260 gaaaaaaaa tcgatgtgga ggaaaagcta acttgtgcca agacaaggtg agtcagtcac    1320
atggacttaa caataatgtc aattatgaaa gctgaaggcc taggacccag ctatctgact   1380
ctactggctg tagacctaag gagcaggtag ggttaaccat agctttcgtg tttacacacg   1440
ttcaagatta atgctcttgc tgaaagaatt tttttacatg ccagccaaag agagttcctt   1500
atggagacct ggatatggtc cagctaagct agaatctccc acttcctgtt ttctcttagt   1560
tggcccacca gctggaggag ctccagaata tctaaattaa tttccaattg tgtaatttga   1620
gaaaaagaga cgaagattaa tttccctaac gagtagggaa gtgtgtttct ttttttttctt  1680
```

| | |
|---|---|
| ttttttttga gactgagtct cgctctgtcg cccagcctga agtgcagtgg cacgatcgcg | 1740 |
| gctagtgcac tgcgaactct gtctcccggg ttcacgccat tctcctgcct cagcctcccg | 1800 |
| agtagctggg actacaggca cccgccatca cgcccagcta atttttttgtg tttttagtag | 1860 |
| agatgggggt tcaccgcgt tagccaggat gacctcgatc tcctgacctc gtgatctgcc | 1920 |
| ttcctcggcc tcccaaagtg ctgggattat aggcgtgagc caccgcacct ggcaggaagt | 1980 |
| gtttcttaaa gttggaaagt ggtatttcag aatatccgct tttggcagac tgagtcagtc | 2040 |
| acttcatttt cctgattttt tgcctaaggt cctggtgaat tgacaaagat tctgcccaaa | 2100 |
| ttttaacgac cccagtaatt acatgtcata tgaatgaata cttgacgtca gcaggactgc | 2160 |
| gttttg | 2166 |

<210> SEQ ID NO 64
<211> LENGTH: 99
<212> TYPE: DNA
<213> ORGANISM: Homo sapiens
<220> FEATURE:
<223> OTHER INFORMATION: EGFR region of interest (ROI) 1, exon 19

<400> SEQUENCE: 64

| | |
|---|---|
| ggactctgga tcccagaagg tgagaaagtt aaaattcccg tcgctatcaa ggaattaaga | 60 |
| gaagcaacat ctccgaaagc caacaaggaa atcctcgat | 99 |

<210> SEQ ID NO 65
<211> LENGTH: 156
<212> TYPE: DNA
<213> ORGANISM: Homo sapiens
<220> FEATURE:
<223> OTHER INFORMATION: EGFR region of interest (ROI) 2, exon 21

<400> SEQUENCE: 65

| | |
|---|---|
| ggcatgaact acttggagga ccgtcgcttg gtgcaccgcg acctggcagc caggaacgta | 60 |
| ctggtgaaaa caccgcagca tgtcaagatc acagattttg gctggccaa actgctgggt | 120 |
| gcggaagaga aagaatacca tgcagaagga ggcaaa | 156 |

<210> SEQ ID NO 66
<211> LENGTH: 2728
<212> TYPE: DNA
<213> ORGANISM: Homo sapiens
<220> FEATURE:
<223> OTHER INFORMATION: EGFR region of interest (ROI) 3, exon 20

<400> SEQUENCE: 66

| | |
|---|---|
| ttgcatcggt actgaacata tacggacttt ttttcttgtc attattccct aaacaataca | 60 |
| gcataacaat tattcacata gcatttgcac tgtattaggt actataggta atcaggagat | 120 |
| gctgtagatg ggaggatgtc tgtaggttac acacaaatgc tgtgccactt tatatcaggg | 180 |
| gcttgagcat cctcacattt tgatatttaa gggaggtcct ggaaccaatt ccccagatac | 240 |
| tgagggtcca ctgtctgtgt cccctcgccc caccttgcct ttgtctcctg tctcctatct | 300 |
| ccaccctgcc tcccgccagc ctgttgctcc tgacctgccc gggcaccctg gagcagcacc | 360 |
| ctatctcaga gcctggctca gtgtgttcac ttctgcagag aaactaactt gcccaagtcc | 420 |
| acactcaaaa cataggcatt gctgagatgt gaaaagcagc tgtggatgct ttctgctaca | 480 |
| gtctgtgtgt cttttccat atctgaataa aaggtcacca ccatttgtat tttaaagaga | 540 |
| aagagaattt atgggtggaa attggggatt ccctcattct cagtcagaca gaaaagaggg | 600 |
| ccccattgtg tgcctgattg caaataaatt tagcttcctc agcccaagaa tagcagaagg | 660 |

```
gttaaaataa agtctgtatt tatggctctg tcaaaggaag gccctgcct tggcagccag    720 ccggaattag cagggcagca gatgcctgac tcagtgcagc atggatttcc catagggagc    780
ctgggggcac agcacagaga gaccacttct ctttagaaat gggtcccggg cagccaggca    840
gcctttagtc actgtagatt gaatgctctg tccatttcaa aacctgggac tggtctattg    900
aaagagctta ccagctact ctttgcagag gtgctgtggg cagggtcccc agcccaaatg     960
cccacccatt tcccagagca cagtcagggc aagcctggc ctgtggggaa gggaggcctt    1020
tctccctgct ggctcggtgc tccccggatg ccttctccat cgcttgtcct ctgcagcacc    1080
cacagccagc gttcctgatg tgcagggtca gtcattaccc agggtgttcc ggaccccaca    1140
cagattccta caggccctca tgatattta aaacacagca tcctcaacct tgaggcggag     1200
gtcttcataa caaagatact atcagttccc aaactcagag atcaggtgac tccgactcct    1260
cctttatcca atgtgctcct catggccact gttgcctggg cctctctgtc atggggaatc    1320
cccagatgca cccaggaggg gccctctccc actgcatctg tcacttcaca gccctgcgta    1380
aacgtccctg tgctaggtct tttgcaggca cagcttttcc tccatgagta cgtattttga    1440
aactcaagat cgcattcatg cgtcttcacc tggaagggt ccatgtgccc ctccttctgg     1500
ccaccatgcg aagccacact gacgtgcctc tccctccctc caggaagcct acgtgatggc    1560
cagcgtggac aaccccacg tgtgccgcct gctgggcatc tgcctcacct ccaccgtgca     1620
gctcatcacg cagctcatgc ccttcggctg cctcctggac tatgtccggg aacacaaaga    1680
caatattggc tcccagtacc tgctcaactg gtgtgtgcag atcgcaaagg taatcaggga    1740
agggagatac ggggagggga gataaggagc caggatcctc acatgcggtc tgcgctcctg    1800
ggatagcaag agtttgccat ggggatatgt gtgtgcgtgc atgcagcaca cacacattcc    1860
tttattttgg attcaatcaa gttgatcttc ttgtgcacaa atcagtgcct gtcccatctg    1920
catgtggaaa ctctcatcaa tcagctacct ttgaagaatt ttctctttat tgagtgctca    1980
gtgtggtctg atgtctctgt tcttatttct ctggaattct ttgtgaatac tgtggtgatt    2040
tgtagtggag aaggaatatt gcttccccca ttcaggactt gataacaagg taagcaagcc    2100
aggccaaggc caggaggacc caggtgatag tggtggagtg gagcaggtgc cttgcaggag    2160
gcccagtgag gaggtgcaag gagctgacag agggcgcagc tgctgctgct atgtggctgg    2220
ggccttggct aagtgtcccc cttttccacag gctcgctcca gagccaggc ggggctgaga     2280 gagcagagtg gtcaggtagc cctgcctggg tgctggagac aggcacagaa caacaagcca    2340
ggtatttcac agctggtgcg gacccagaaa gacttctgct tttgccccaa accctccca     2400 tctccatccc agtcttgcat cagttatttg cactcaactt gctaagtcct atttttttct    2460
aacaatgggt atacattca tcccattgac tttaaaggat ttgcaggcag gcctgtctc     2520 tgagaatacg ccgttgcccg tcatctctct ccgacagcag gcaggggt ccagagatgt      2580 gccagggacc agagggaggg agcagacacc caccgcct gggcaggtcc tcctcattgc      2640
ttgcatccgc ctggttagca gtggcagtca gtcctgccga gtcattcgtg aggcgctcac    2700
ccaactccag gcagatgtaa aaggtgac                                        2728
```

<210> SEQ ID NO 67
<211> LENGTH: 123
<212> TYPE: DNA
<213> ORGANISM: Homo sapiens
<220> FEATURE:
<223> OTHER INFORMATION: EGFR region of interest (ROI) 4, exon 18

<400> SEQUENCE: 67

```
cttgtggagc tcttacacc cagtggagaa gctcccaacc aagctctctt gaggatcttg      60
aaggaaactg aattcaaaaa gatcaaagtg ctgggctccg gtgcgttcgg cacggtgtat    120
aag                                                                  123
```

<210> SEQ ID NO 68
<211> LENGTH: 122
<212> TYPE: DNA
<213> ORGANISM: Homo sapiens
<220> FEATURE:
<223> OTHER INFORMATION: KRAS region of interest (ROI) 1, exon 2

<400> SEQUENCE: 68

```
ctctattgtt ggatcatatt cgtccacaaa atgattctga attagctgta tcgtcaaggc      60
actcttgcct acgccaccag ctccaactac cacaagttta tattcagtca ttttcagcag    120
gc                                                                   122
```

<210> SEQ ID NO 69
<211> LENGTH: 179
<212> TYPE: DNA
<213> ORGANISM: Homo sapiens
<220> FEATURE:
<223> OTHER INFORMATION: KRAS region of interest (ROI) 2, exon 3

<400> SEQUENCE: 69

```
ctataatggt gaatatcttc aaatgattta gtattattta tggcaaatac acaagaaag      60
ccctccccag tcctcatgta ctggtccctc attgcactgt actcctcttg acctgctgtg    120
tcgagaatat ccaagagaca ggtttctcca tcaattacta cttgcttcct gtaggaatc    179
```

<210> SEQ ID NO 70
<211> LENGTH: 671
<212> TYPE: DNA
<213> ORGANISM: Homo sapiens
<220> FEATURE:
<223> OTHER INFORMATION: KRAS region of interest (ROI) 3, exon 4

<400> SEQUENCE: 70

```
tctgttggct ttctgggtat tgtctttctt taatgagacc tttctccaga aataaacaca      60
tcctcaaaaa aattctgcca agtaaaaatt cttcaaatac aacaacgttt aacctagaaa    120
catgacataa tggtttaaaa gtactaccga aatagaaaac gcaaaaattt gttgccctgt    180
tctttatata tatatatata tatatatata tatatatata tatatatata tatgtaacca    240
tgggaaaaaa aaatccccac ctcttgaatt ctaaatgtta acatgtgctc agaattgaag    300
agaaattttc aatgtagaaa gaaaccaaag ccaaaagcag taccatggac actggattaa    360
gaagcaatgc cctctcaaga gacaaaaaca tttactaaat attgttttat ttcctagtat    420
agcataattg agagaaaaac tgatatatta aatgacataa cagttatgat tttgcagaaa    480
acagatctgt atttatttca gtgttactta cctgtcttgt ctttgctgat gtttcaataa    540
aaggaattcc ataacttctt gctaagtcct gagcctgttt tgtgtctact gttctagaag    600
gcaaatcaca tttatttcct actaggacca taggtacatc ttcagagtcc ttaactcttt    660
taatttgttc t                                                         671
```

<210> SEQ ID NO 71
<211> LENGTH: 119
<212> TYPE: DNA
<213> ORGANISM: Homo sapiens
<220> FEATURE:
<223> OTHER INFORMATION: BRAF region of interest (ROI) 1, exon 15

<400> SEQUENCE: 71

| | |
|---|---|
| catccacaaa atggatccag acaactgttc aaactgatgg gacccactcc atcgagattt | 60 |
| cactgtagct agaccaaaat cacctatttt tactgtgagg tcttcatgaa gaaatatat | 119 |

<210> SEQ ID NO 72
<211> LENGTH: 118
<212> TYPE: DNA
<213> ORGANISM: Homo sapiens
<220> FEATURE:
<223> OTHER INFORMATION: BRAF region of interest (ROI) 2, exon 11

<400> SEQUENCE: 72

| | |
|---|---|
| catgccactt tcccttgtag actgttccaa atgatccaga tccaattctt tgtcccactg | 60 |
| taatctgccc atcaggaatc tcccaatcat cactcgagtc ccgtctacca agtgtttt | 118 |

<210> SEQ ID NO 73
<211> LENGTH: 287
<212> TYPE: DNA
<213> ORGANISM: Homo sapiens
<220> FEATURE:
<223> OTHER INFORMATION: AKT1 region of interest (ROI)

<400> SEQUENCE: 73

| | |
|---|---|
| gggatactta cgcgccacag agaagttgtt gaggggagcc tcacgttggt ccacatcctg | 60 |
| cggccgctcc ttgtagccaa tgaaggtgcc atcattcttg aggaggaagt agcgtggccg | 120 |
| ccaggtcttg atgtactccc ctacagacgt gcgggtggtg agagccacgc acactctacc | 180 |
| cgtcagaccc tcgccaggca gccaggcagg aactgggtgt gccaggacag atgtgcctgg | 240 |
| gatgcctgag tcccagggg caggcgcggt acgggagctg tttctta | 287 |

<210> SEQ ID NO 74
<211> LENGTH: 135
<212> TYPE: DNA
<213> ORGANISM: Homo sapiens
<220> FEATURE:
<223> OTHER INFORMATION: DDR2 region of interest (ROI) 1, exon 19

<400> SEQUENCE: 74

| | |
|---|---|
| acttacctcc ctcaaccagc catttgtcct gactctgtgt ataagctgat gctcagctgc | 60 |
| tggagaagag atacgaagaa ccgtccctca ttccaagaaa tccaccttct gctccttcaa | 120 |
| caaggcgacg agtga | 135 |

<210> SEQ ID NO 75
<211> LENGTH: 150
<212> TYPE: DNA
<213> ORGANISM: Homo sapiens
<220> FEATURE:
<223> OTHER INFORMATION: DDR2 region of interest (ROI) 2, exon 18

<400> SEQUENCE: 75

| | |
|---|---|
| ggcaagttca ctacagcaag tgatgtgtgg gcctttgggg ttactttgtg ggagactttc | 60 |
| accttttgtc aagaacagcc ctattcccag ctgtcagatg aacaggttat tgagaatact | 120 |
| ggagagttct tccgagacca agggaggcag | 150 |

<210> SEQ ID NO 76
<211> LENGTH: 719
<212> TYPE: DNA

<213> ORGANISM: Homo sapiens
<220> FEATURE:
<223> OTHER INFORMATION: DDR2 region of interest (ROI) 3, exons 16 and 17

<400> SEQUENCE: 76

```
gaatgatttt cttaaggaga taaagatcat gtctcggctc aaggacccaa acatcatcca    60
tctattagct gtgtgtatca ctgatgaccc tctctgtatg atcactgaat acatggagaa   120
tggagatctc aatcagtttc tttcccgcca cgagccccct aattcttcct ccagcgatgt   180
acgcactgtc aggtaaacaa gccaggtctt ccttctcctc cctgtggtca tgagagtaac   240
ctgggatctg aaaatagga gcagtgagcc ttaaagtgta tcaatgttct gggatggtgg   300
gggaagtcag tgtgcaggga ataatggagc agctgccctt tggggaaacg caagggattc   360
atcaagagta gagaaagaat gttgagcttt caacccctagt ttgttgatac cattttagaa   420
tgtgtacctt tcacatcttc ctgtttccat aggctaccctt ctgtcttctt gtctatttcc   480
tcagttacac caatctgaag tttatggcta cccaaattgc ctctggcatg aagtacccttt   540
cctctcttaa ttttgttcac cgagatctgg ccacacgaaa ctgtttagtg ggtaagaact   600
acacaatcaa gatagctgac tttggaatga gcaggaacct gtacagtggt gactattacc   660
ggatccaggg ccgggcagtg ctccctatcc gctggatgtc ttgggagagt atcttgctg   719
```

<210> SEQ ID NO 77
<211> LENGTH: 186
<212> TYPE: DNA
<213> ORGANISM: Homo sapiens
<220> FEATURE:
<223> OTHER INFORMATION: ERBB2 region of interest (ROI)

<400> SEQUENCE: 77

```
gaagcatacg tgatggctgg tgtgggctcc ccatatgtct cccgccttct gggcatctgc    60
ctgacatcca cggtgcagct ggtgacacag cttatgccct atggctgcct cttagaccat   120
gtccgggaaa accgcggacg cctgggctcc caggacctgc tgaactggtg tatgcagatt   180
gccaag                                                             186
```

<210> SEQ ID NO 78
<211> LENGTH: 211
<212> TYPE: DNA
<213> ORGANISM: Homo sapiens
<220> FEATURE:
<223> OTHER INFORMATION: MAP2K1 (MEK1) region of interest (ROI)

<400> SEQUENCE: 78

```
gaccaacttg gaggccttgc agaagaagct ggaggagcta gagcttgatg agcagcagcg    60
aaagcgccctt gaggcctttc ttacccagaa gcagaaggtg ggagaactga aggatgacga   120
ctttgagaag atcagtgagc tgggggctgg caatggcggt gtggtgttca aggtctccca   180
caagccttct ggcctggtca tggccagaaa g                                   211
```

<210> SEQ ID NO 79
<211> LENGTH: 66
<212> TYPE: DNA
<213> ORGANISM: Homo sapiens
<220> FEATURE:
<223> OTHER INFORMATION: NRAS region of interest (ROI) 1, codon 61

<400> SEQUENCE: 79

```
cctgtcctca tgtattggtc tctcatggca ctgtactctt cttgtccagc tgtatccagt    60
```

```
atgtcc                                                              66

<210> SEQ ID NO 80
<211> LENGTH: 66
<212> TYPE: DNA
<213> ORGANISM: Homo sapiens
<220> FEATURE:
<223> OTHER INFORMATION: NRAS region of interest (ROI) 2, codon 12

<400> SEQUENCE: 80
tttgttttta tgtattggtt ttttatggta ttgtatttt tttgtttagt tgtatttagt    60
atgttt                                                              66

<210> SEQ ID NO 81
<211> LENGTH: 303
<212> TYPE: DNA
<213> ORGANISM: Homo sapiens
<220> FEATURE:
<223> OTHER INFORMATION: PIK3CA region of interest (ROI) 1, exon 9

<400> SEQUENCE: 81
ataagatatt attttatttt acagagtaac agactagcta gagacaatga attaagggaa    60
aatgacaaag aacagctcaa agcaatttct acacgagatc ctctctctga aatcactgag   120
caggagaaag attttctatg gagtcacagg taagtgctaa aatggagatt ctctgtttct   180
ttttctttat tacagaaaaa ataactgaat ttggctgatc tcagcatgtt tttaccatac   240
ctattggaat aaataaagca gaatttacat gatttttaaa ctataaacat tgccttttta   300
aaa                                                                303

<210> SEQ ID NO 82
<211> LENGTH: 455
<212> TYPE: DNA
<213> ORGANISM: Homo sapiens
<220> FEATURE:
<223> OTHER INFORMATION: PIK3CA region of interest (ROI) 2, exon 20

<400> SEQUENCE: 82
gtctacgaaa gcctctctaa ttttgtgaca tttgagcaaa gacctgaagg tattaacatc    60
atttgctcca aactgaccaa actgttctta ttacttatag gtttcaggag atgtgttaca   120
aggcttatct agctattcga cagcatgcca atctcttcat aaatcttttc tcaatgatgc   180
ttggctctgg aatgccagaa ctacaatctt ttgatgacat tgcatacatt cgaaagaccc   240
tagccttaga taaaactgag caagaggctt tggagtattt catgaaacaa atgaatgatg   300
cacatcatgg tggctggaca acaaaaatgg attggatctt ccacacaatt aaacagcatg   360
cattgaactg aaaagataac tgagaaaatg aaagctcact ctggattcca cactgcactg   420
ttaataactc tcagcaggca aagaccgatt gcata                             455

<210> SEQ ID NO 83
<211> LENGTH: 455
<212> TYPE: DNA
<213> ORGANISM: Homo sapiens
<220> FEATURE:
<223> OTHER INFORMATION: PTEN region of interest (ROI), exon 7

<400> SEQUENCE: 83
tcaaactgga gaaatctta cattgtttat atttttattt catttatttc agttgatttg    60
cttgagatca agattgcaga tacagaatcc atatttcgtg tatattgctg atattaatca   120
ttaaaatcgt ttttgacagt ttgacagtta aaggcatttc ctgtgaaata atactggtat   180
```

```
gtatttaacc atgcagatcc tcagtttgtg gtctgccagc taaaggtgaa gatatattcc    240
tccaattcag gacccacacg acgggaagac aagttcatgt actttgagtt ccctcagccg    300
ttacctgtgt gtggtgatat caaagtagag ttcttccaca aacagaacaa gatgctaaaa    360
aaggtttgta ctttactttc attgggaaa atatccaaaa taaggacaga ttaaaagcta     420
tattttattt tatgacatgt aaggaactat aattt                              455
```

<210> SEQ ID NO 84
<211> LENGTH: 593
<212> TYPE: DNA
<213> ORGANISM: Homo sapiens
<220> FEATURE:
<223> OTHER INFORMATION: IDH1 region of interest (ROI)

<400> SEQUENCE: 84

```
tatggtataa ctgaataaaa ggataaagga aaaaaaacag catgtttgaa aaaaaatgtg    60
ttgagatgga cgcctatttg taagtttatt tgtatttgcc tttagctaaa tgtgtgtaaa    120
tatacagtta tacatatatg catttctcaa tttcataccct tgcttaatgg gtgtagatac   180
caaaagataa gaataaaaca catacaagtt ggaaatttct gggccatgaa aaaaaaaaca    240
tgcaaaatca cattattgcc aacatgactt acttgatccc cataagcatg acgacctatg    300
atgataggtt ttacccatcc actcacaagc cggggggatat ttttgcagat aatggcttct   360
ctgaagaccg tgccacccag aatatttcgt atggtgccat ttggtgattt ccacatttgt    420
ttcaacttga actcctcaac cctcttctca tcaggagtga tagtggcaca tttgacgcca    480
acattatgct tctttatagc ttctgcagca tccttggtga cttggtcgtt ggtggcatca    540
cgattctcta tgcctaaatc atagcttgaa agagaaaaat tagaagcaaa gtt           593
```

<210> SEQ ID NO 85
<211> LENGTH: 377
<212> TYPE: DNA
<213> ORGANISM: Homo sapiens
<220> FEATURE:
<223> OTHER INFORMATION: IDH2 region of interest (ROI)

<400> SEQUENCE: 85

```
ggaagttgta cacttcccac tccttgacac cactgccatc ttttggggtg aagaccattt     60
tgaaagtgcc ggcccggtct gccacaaagt ctgtggcctt gtactgcaga gacaagagga    120
tggctaggcg aggagctcca gtcgggggt gcccaggtca gtggatcccc tctccaccct    180
ggcctacctg gtcgccatgg gcgtgcctgc caatggtgat gggcttggtc cagccaggga    240
ctaggcgtgg gatgttttg cagatgatgg gctcccggaa gacagtcccc cccaggatgt    300
tccggatagt tccattggga ctttttccaca tcttcttcag cttgaactct gtgaggacag   360
agataatagt ggtccca                                                   377
```

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer (F1) suitable for BRCA1
      methylation analyses

<400> SEQUENCE: 86

```
ccaataccc  aaaacatcac tt                                               22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer (R1) suitable for BRCA1
      methylation analyses

<400> SEQUENCE: 87
ggggtagatt gggtggttaa tt                                               22

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer (F2) suitable for BRCA1
      methylation analyses

<400> SEQUENCE: 88
ctaaacgcaa aacccaatt atct                                              24

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer (R2) suitable for BRCA1
      methylation analyses

<400> SEQUENCE: 89 ggttttttt gttttttta tttttga                                            28

<210> SEQ ID NO 90
<211> LENGTH: 1791
<212> TYPE: DNA
<213> ORGANISM: Homo sapiens
<220> FEATURE:
<223> OTHER INFORMATION: PITX2 region of interest (ROI) 1 (promoter A),
      preferred for methylation analyses

<400> SEQUENCE: 90
cttccagtag ctgaaacttt gtacccagcc ctttatcttg agaatgctaa tccttggccc        60
gaggatttgt tcctgcagtg ttggcaccga gatttaaggg aagatacctc gttttaaatg       120
ccagccacgg tctggcttcc ctctcgactt cagcaccctg tagattgtta gtgtctgtgg       180
cgggggacga aggaacagg gctttgcaag gtctgtttgc cgactgcgtt accttgggcg        240
aaacttagcc ccaaaagcca caatcacct acggtgaaga ttctccgaag tggaacaaat       300
ttccagactc gcattatctc acatccctgc gggatagatg gcctccactt accggctacc       360
gggagagagc tgctgtctcc gcgtcccact gcttcccggg gcgatttcca gcgagccgag       420
cctccggctg cacggcaagc gcccgaaagc cgggcctgag aggactgcag ggctcctgag       480
ggtgccaagt tccgaaggag tccacgggtg cactgggggcc tccgaaatct agccgccact     540
```

-continued

```
ggcagtttct ttctgctcct ctccagcttt ctcgctcggt ctcgcactct ctctcctctc     600
cctccctctc atccctctct cttccctctg ctcctactcc gtgtggggag tgacgtgacg     660
tcagcagaga ttccaccaaa ctccactgca cagtggcgcg cgggcggccg gccgagcccg     720
gctgcgcggc tggcgatcca ggagcgagca cagcgcccgg gcgagcgccg ggggagcga     780 gcagggcgga cgagaaacga ggcaggggag ggaagcagat gccagcgggc cgaagagtcg     840
ggagccggag ccgggagagc gaaaggagag gggacctggc ggggcactta ggagccaacc     900
gaggagcagg agcacggact cccactgtgg aaaggaggac cagaagggag gatgggatgg     960
aagagaagaa aaagcaatct gcgccaaccc ggcagcccta ataaatcaaa ggggagcgc    1020 cagggcagcg gggagacaga aacgtacttt tggggagcaa atcaggacgg gctggaggaa   1080
agcgacaggg aaagtggccc aagagacgga acaaaggaca atgttcatgg ggttgtttgg   1140
gacgaggcgt gtggagtgtg ggtgtgagcg tgcgtgtgtg accttctttc aggcctgcag   1200
agttgaggaa agaggtcaca gcaagagggg actgcggagg gaggaaagtg agagaccggt   1260
agagggcggg agtggaggtg ggcgcggtgg ggatgggaga ggatgagtga agagaaatct   1320
agaagaatgg agtgagctag tgggagaggg tgggagggcc acagccggga gcgaacgagc   1380
taggcttgtc agctggggaa ggccgggacg ctgggcccag cttagctggg acaccgcgcc   1440
cgaggtcaag gcgggtggac caggcatgct gagagtgtcg gcgcacaggt gggcacggcc   1500
acgcactgac ccagtgttca cgaagggttt gcactggaca aggctcagac gctcatagag   1560
tctagaattt cctctgctgt acctacattc aacaagttca ccctgggtca cggatatctc   1620 atttttaaa atgacgaggt taaggttcct ggcgaggatg gtattaaatt gcacgggata   1680
gaagtggggg tgggggagag agtttccctc aagtccacat ttgctcctgc aaagcaaaga   1740
gtatgtgaaa ttacagggca tattctcact cgaaaagtgt gccttacttc t             1791
```

<210> SEQ ID NO 91
<211> LENGTH: 6265
<212> TYPE: DNA
<213> ORGANISM: Homo sapiens
<220> FEATURE:
<223> OTHER INFORMATION: PITX2 region of interest (ROI) 2 (promoter C),
      preferred for methylation analyses

<400> SEQUENCE: 91

```
tattactaac aactgctttt ataaaattaa tttgacattt cgatatatat acatcctttc      60
agtcatttaa atgttaacaa tgctaaactt aaaaaataac aagcttatag taatgttaaa    120
atgtcatatc cagtcaaaca tttgtttgtg tatgtgtcct tgcaactgtt agaaatactt    180
gtagtgaaag atgtcagaca ctgaggacat ccctttgaaa tcaaggagc tctctctttg    240 attcagtggt ttccttttct ctatatagct tctctttctc tcccttttctt tagtgcccac    300 gaccttctag cataattccc agtctttcaa gggcggagtt gccccatccg gcaaggtcct    360
aggatcccgg cgctgtgggt gcggctcaca cgggccggtc cactgcatac tggcaagcac    420
tcaggttgga ggccgggttc tgcacgctgg cgtagccgaa gctggagtgc tgctttgctt    480
tcagtctcag gctggccagg ctcgagttac acgtgtccct ataaacatac ggaggagtcg    540
gcggcgcgta aggacaggca ggcgtcgcca ccgcggaatt cagcgacggg ctactcaggt    600
tgttcaagtt attcaggctg ttgagactgg agcccgggac gcctgtcact gctgagggca    660
ccatgctgga cgacatgctc atggacgaga tagagttggg tggggaaaac atgtctgtg    720 atgacagggg gttgacgttc atagagttga agaagggaa gctcttggtg gataggagg     780
```

| | | | | |
|---|---|---|---|---|
| cggatgtaag | gcccttggcg | gcccagttgt | tgtaggaata | gcctgggtac | atgtcgtcgt | 840 |
| agggctgcat | gagcccattg | aactgcggcc | cgaagccatt | cttgcatagc | tcggcctgct | 900 |
| ggttgcgctc | cctctttctc | catttggccc | gacgattctt | gaaccaaacc | tggggcggt | 960 |
| tggggcaagg | gagcaaacag | atgccacagt | gcagattact | aaaacttcca | tcggaggcca | 1020 |
| accccgcct | tccccgaca | cacacgctag | cgcactcaca | caccctggcc | tcgcttcact | 1080 |
| gcaccgccct | gcacaccaag | ataccagggc | cagctttcag | ttactggccc | gggtctccac | 1140 |
| caagcgcagg | agacctggtc | tgctctggcc | tgcgagctgg | gactcggagc | tacgccacaa | 1200 |
| acctcagccg | aacgcatgga | gacctgcgga | cggtttgatc | actcagccag | gcgtttctcc | 1260 |
| aggtccaaaa | acacttaatg | taaaacaaac | gcggggcagc | aggcttttcc | aacccttccc | 1320 |
| ggggcacctt | gcaaacttgc | ttccattcca | aagccacaga | cccacggatg | aggagaaggg | 1380 |
| gctggaaggg | cactagagga | tcgctctttc | tcccacgcaa | ttcctcccctt | ccttccctga | 1440 |
| cctccactgt | cgtcccccac | cccctggtac | gtgctcccctt | aacagggact | aggccgccaa | 1500 |
| cactctttct | cgcctagcaa | aacaaccaaa | taaagagcaa | aagaccacct | cttcgtcagc | 1560 |
| tcgttaactc | caggagcttg | gcatattaaa | ctccgggaac | ccggaaaggg | tagttttgga | 1620 |
| gattccccct | tctttcgctc | tgcctcttct | ttacccctaag | cccaccacag | gcctgtccgc | 1680 |
| gcgccaggcc | cagccgggtc | gtttggcttt | gcaggcggcc | acccaggccg | gccggcttcc | 1740 |
| acccgtgtcc | ggtggcccag | ccgcaacccc | gatcccaatc | cacatcgggc | ctccctgtcg | 1800 |
| ccccagacgg | cggcttttgt | gtattggaga | gaggcctggc | ctgagatatc | cgagctgaca | 1860 |
| ccagtgatgt | ttcacattac | acatctccgc | cgggcccagc | cgtgtaatcc | gcttttctc | 1920 |
| ttttttccttt | cattcttgat | ttcctttta | tccccttcc | tctttgcacc | cgactgctat | 1980 |
| aaaaagcacg | cctcactccc | acttggctcg | acaagcagcc | gccctggaag | gagaggcagc | 2040 |
| tgcaaggaga | gcccagcgcc | gcggctacaa | agcactaggg | tggagctgcg | aatagcggg | 2100 |
| cggggtggga | gggcgttttc | gaaggatccc | agaaaaccca | tagactctgt | ctttaattac | 2160 |
| ttgccatttc | taccctaggc | catctaaact | ttgctcaggc | gagaagagta | cgtgagaggc | 2220 |
| ccgttcccctt | gatgtgcaag | agagctaatg | aaagactgac | cttgctcaaa | accacgccgc | 2280 |
| ccaggaccca | gctctggctc | tggacagtta | aactaaaacc | attttcaact | tcttcccggc | 2340 |
| cttttatcca | ccagcatagc | ctcatgcctt | gcacaaatgc | cacccagaga | gtgtcttcat | 2400 |
| tccctctgat | ttgggagagc | attttggtct | ttattcttt | tatcgttgtt | ttcttctttt | 2460 |
| tgtttgctct | gctctaaccg | ggggctttat | ttttttctacc | cagagcactt | aattttttt | 2520 |
| ttttaacagc | aaagcctctg | gatgccgctt | gatttgcttg | attctgttt | ctgcttccag | 2580 |
| aatcctaaca | aatttggaat | cttccaccga | ccagcataaa | ccaggacgtt | gctattgggt | 2640 |
| tatttatttg | agctcatttt | tgccaatcca | taaagtacag | atttgctaca | aagttaaggt | 2700 |
| aagcccttt | tacaaaacta | tgattataat | ttagaagagg | gggtgtgagt | ttcaatttcc | 2760 |
| agagttcaac | tcctgagaga | agataaataa | accaagcaga | aaagtctttc | ttcttttttt | 2820 |
| ctttctccttt | ctaagaggac | tagtagttgt | gtattaaaac | tttgctcccg | gagatcacaa | 2880 |
| aactaggaaa | tagggtgtgt | gggagagacc | tgaatggccg | aaacaaccgt | aaagaaggtg | 2940 |
| taagaagcgc | gagcccagga | gggaaaaagc | tgggccaggg | ccgggacaaa | ggtttcccag | 3000 |
| ggagggccaa | ctcttccgtg | tctctggcgg | gttttccttg | ttaaaggctc | acaggttgga | 3060 |
| gcctgttcgc | ggctcttggc | ctggtaggga | ttttattagc | tctgctctgg | caactgcaag | 3120 |
| ccaggaacac | aatgtcctgt | gcaggggatt | gcccatgcag | cccagctcgt | gagatcgcgg | 3180 |

```
gatggcgggg cagtgagccg gtgccgctct gggagcctga gccagggcgg cagtcctgtc   3240
ggcctcggag agggaactgt aatctcgcaa ccaggccgcc gcgaggcctt ctgcctttgc   3300
aaagctgcgc cccaccggcg ccctcccagg cggcgctgcc ttccacattc tctcctggtc   3360
tacttggcct gtacctccac aacatcctcc ccccatccct cccagactcc gtgctggctc   3420
ctacccggac tcgggcttcc gtaaggttgg tccacacagc gatttcttcg cgtgtggaca   3480
tgtccgggta gcggttcctc tggaaagtgg cctccagctc ctggagctgc tggctggtaa   3540
agtgagtccg ctgccgcctt tgccgcttct tcttagacgg gtcctcggcg cccacgtcct   3600
cattcttccc ctgctggctt ttatctttct ctgaaaacga acacacaca ctttcccgtc   3660 agcatgccca cctgcaacgc ggacgccaac tggaccggcg gcagaagccg tggaagagct   3720
gggctgcctg gcgccggagg agggtgcgcg cggcggctcc gggccgcgag gagcgctgcg   3780
cctgtggggt gtgcaggcgc aagtgtgggt gtccgcgccc catttcctcc cctcccccag   3840
cgccgcacgt tttatttaca tgtttatctc actgcagcgg cacattcact tttatagcct   3900
gtgctttcaa gtatatttat acacctctgc gcagacacac caaatctcct gggacgcgca   3960
cacgcgcgtg gttacagac ccccctcccc ctcgcagaaa gctcagattt ccatgcggtt   4020
tgggaaggct aggaaaagat gtggggattc ggttgggcac cgaagttcgc cggccctttc   4080
ccaaaaaaaa aaaaaaaatg cctcttcgcg aagggcattt ctgagtggtt tcaggcaatt   4140
tcctaacgag tggagctcct cgggagctga agccgagag gaaaacaggg acagaggtcg   4200
gcggcctctg aagtcctcg aatcaagatg ctgggatttt tgtgacccag gaaacagaag   4260
ggaggccagg gtacgaatag agagggcggc agaattgctc gcgcccttag cgccccagga   4320
gccgggccgt tcgagggaga actaaaggga tgcggggtag tcaaaattcc ggctcccgga   4380
agttctgcgg ggagccaggc gaacgaccac tcccaccacg cctcccccg gaggggctga   4440 cttccttggg gcgagaggga gcgggtggcg cagagcagct gagcgggaat gtctgcaggg   4500
cggcgcggcg ccttacctgc ggcctccggg ctggaggtgt cggagatggt gtgcacctcc   4560
agcctgtgct tggaggagtc cagcgaccgg ggctgaccgg gagccagaac cgaagccatg   4620
gctaacggct ggggatggtg acaggaagat gaggagacgg ccgacagctt ggtccccgct   4680
gctcggtgct ccaagtgaag cgggccttc atgcagttca tggacgaggg agcgcgacgc   4740
tctactagtc cttggctact gccccgccga gcccccgtag ccgccgctgc ccgctccggg   4800
tcgcgctcta ggcgcggagt ttccccgctg cggggagagc caggggacgc aaccccgcc   4860 gagttctcaa gccaagctgc ccccgtctcc tccggaaggc tcaagcgaaa aagtccggag   4920
acggaaagtc agcgggcaaa cgaagacatg ggatgtgggc agaagggcac cactcagagc   4980
gtctttaggg agcaggcttc caagctccaa agcgaaacaa gagtgggcaa agacccctt   5040 cttctctccc tccctccccc aagaacccct ccaataagga aagctaacgc cgaccgcgct   5100
ctgcccgccc cccccacg cggcagccct gacagagaag tgtcaagagt gacagggaca   5160
ggtaggtgat attagatccc ctgcggcggc agcagccgct gcagccacga cgcggccctc   5220
tgagcgcacc ctccgcaacg cgcacacgca cacccctcgg gcggtcgaac aggagccggg   5280
ccttgccgca gctcagctcc aggcacccag gcgagcgacg gaccagatct gcggctccgc   5340
gcttccctgt tggcctaaca tcttaaaacc agaggcgggc ttcctggtgc cgagacgtca   5400
ctccgccgcg gccctcccca gccctctccg cctccgcctc ctcccagacc cttctccggg   5460
tgcgactgac gtggctccgc accaatcagg acgccccgag ccgcggtgga gggactgtcc   5520
```

```
tgcctgcacc tatcagcagt gcggggccgg gctactgcct cgccgtgcgc actgggtcta    5580
cacaggcaag ctcccgggaa ttcagctcct gcccagccca aggcgatccg gcttttagta    5640
cgaacccaaa ggtgaagaga tgaggctagg agtcgaaggc ttgggagaag agagtggaat    5700
ggtcaagaag agaaaggtac aaggatcaac aagacaccca ctctttgtgt ctcactacat    5760
ccatttccaa tcccccaccc catataaaaa ggagacacgt tacttaaaac tagaaaattt    5820
gaaaaacagc aacaaatcac ctctccgatc ttaaattttc caaacagcct gtcaagtgaa    5880
tgctgcgcta atctgaagaa gctttaattg caaagaagac agagccctga aaaggcaggc    5940
taataaatta gaaatcgaga agcaaatgga cccgtcaaaa gaaaattacc ttgactttaa    6000
acgaacaact gtttggtggt tcactctgga tttatacaag aataaaaagt cgcctcagat    6060
cacgttctct gtgatgctta ttagtcccca gacagaaaac acacaataga agagaaaccc    6120
taacccagcg ttttcaaaat gctgaaagct tatccattct acttaacgtt gattaagaca    6180
catatcctag atctttcaaa ttccttgtac actgtattaa gctcgtccta acccgagaga    6240
gccacgcttt aaattcgact ctctt                                         6265
```

<210> SEQ ID NO 92
<211> LENGTH: 2449
<212> TYPE: DNA
<213> ORGANISM: Homo sapiens
<220> FEATURE:
<223> OTHER INFORMATION: MGMT region of interest (ROI) 1, preferred for
      methylation analyses

<400> SEQUENCE: 92

```
ctccaacata gcttctctgg tggacacaat tcaactccta ataacgtcca cacaacccca      60
agcagggcct ggcaccctgt gtgctctctg gagagcggct gagtcaggct ctggcagtgt     120
ctaggccatc ggtgactgca gccctggac ggcatcgccc accacaggcc ctggaggctg     180
cccccacggc cccctgacag ggtctctgct ggtctggggg tccctgacta ggggagcggc     240
accaggaggg gagagactcg cgctccgggc tcagcgtagc cgccccgagc aggaccggga     300
ttctcactaa gcgggcgccg tcctacgacc cccgcgcgct tcaggacca ctcgggcacg      360 tggcaggtcg cttgcacgcc cgcggactat ccctgtgaca ggaaaaggta cgggccattt     420
ggcaaactaa ggcacagagc ctcaggcgga agctgggaag gcgccgcccg gcttgtaccg     480
gccgaagggc catccgggtc aggcgcacag ggcagcggcg ctgccggagg accagggccg     540
gcgtgccggc gtccagcgag gatgcgcaga ctgcctcagg cccggcgccg ccgcacaggg     600
catgcgccga cccggtcggg cgggaacacc ccgcccctcc cgggctccgc cccagctccg     660 ccccccgcgcg ccccggcccc gccccgcgcg gctctcttgc tttttctcagg tcctcggctc    720 cgccccgctc tagaccccgc cccacgccgc catccccgtg cccctcggcc ccgccccgc     780 gccccggata tgctgggaca gcccgcgccc ctagaacgct tgcgtcccg acgcccgcag     840 gtcctcgcgc tgcgcaccgt ttgcgacttg gtgagtgtct gggtcgcctc gctcccggaa     900
gagtgcggag ctctcccctcg ggacggtggc agcctcgagt ggtcctgcag gcgccctcac     960
ttcgccgtcg ggtgtggggc cgccctgacc cccacccatc ccgggcgagc tccaggtgcg    1020 cccccaagtgc ctcccaggtg ttgcccagcc tttccccggg cctggggttc ctggactagg    1080
ctgcgctgca gtgactgtgg actggcgtgt ggcggggtc gtggcagccc ctgccttacc    1140
tctaggtgcc agcccaggc ccgggccccg ggttcttcct acccttccat gctgccagct    1200
ttccctccgc cagctgctcc aggaagcttc cagaagcccc tgcgcgggcc ttggcttgca    1260
```

| | |
|---|---|
| gcaacccttt agcatactta ggcagagtcc catatttcct tcctgctgga ggccaagttc | 1320 |
| tagggccctt ctggttacta tggctggtgt ttgtgtacat catacgctaa ctgtattcat | 1380 |
| caacacttag agtaagcaag gctcgctgga gagccacaca cactgggcac cgtaatgtcg | 1440 |
| gttataacac cgcagaggag ttctgaacta tgtatttcgc actcctgggt tcatcatctc | 1500 |
| ctgaaatctc agggtggtgt ttgctctcag ttgcttcagc tgagtagctg gctttctgtc | 1560 |
| ctggaaagca gactttgtac atgtgtgtgc aacctatgcc tgctgagatc atcatcagac | 1620 |
| agggaagcgg cttggtccag agagctgttc tcagtagaat gttaagcaca gagagctgag | 1680 |
| aattagactg gttatttaca tagacatcca aatagaaacc tatagagtat ctgttaagtc | 1740 |
| aggctctccc gtcatctccc ccatccctgg gcaggtgtct aggagatggt tttgttattt | 1800 |
| tcagggccct ctcaatggct aaaacactct gggagatgaa caagatttta aaaacccaaa | 1860 |
| gcttagcgca cctggtgggt ggggtgtga aactttgaa ggaaaccgcg tcaagagcct | 1920 |
| ggctgattgt taatatcacg ttaactcaga gggccaggat acttgccag acccggagtc | 1980 |
| tgcctgcaag tagcagagga gagctggcct tgctctgccg cgtgtctttc ttcctgggcc | 2040 |
| ctctgtctcg ggttggaatt tgaatagtgg agtagtgtct gccacagtca ggggcctgga | 2100 |
| tgaagtagac caccagtacg gagctatact caggtacttt tcaatgtata tatcttcatt | 2160 |
| aaaaaaaaaa aatctgggcc aggcacagtg ggtcacgcct gtaatctcag cactttggga | 2220 |
| ggccgaggtg ggtggatcac ctgaagtcag gagtttgaga ccagcctggc caacatggtg | 2280 |
| aaacccagtt tctactaaaa acacaaaaat tatccaggcg tggtggtgca tgctggtaat | 2340 |
| cccagttact tgggagactg aggcaggaga attgcttgaa cctgggaggc ggaggttgca | 2400 |
| gtgagccgag attgcgccat tgcactccaa cctgggcgac gagagtgaaa | 2449 |

<210> SEQ ID NO 93
<211> LENGTH: 2928
<212> TYPE: DNA
<213> ORGANISM: Homo sapiens
<220> FEATURE:
<223> OTHER INFORMATION: SEPT9 region of interest (ROI) 1, preferred
      for methylation analyses

<400> SEQUENCE: 93

| | |
|---|---|
| tttcagaggg ggtggggagg ggcaagtggg cagcgagcga cctcagaccc aggatgagct | 60 |
| gtcaggcgct ccccggccac acattcaagg gaccggagtg cagttgtagc gttgcggcct | 120 |
| gctgcttcgg gggtggggt gttgttccat gctgtgaatt ctcacatggc ccctgactct | 180 |
| gggcagaggc cgagggtcta agggacgggg tgacagggag agcatgcagg agtgggtttc | 240 |
| tggcttttcca gggcgagtgg aagaagcgcc tctctctctt gtaggtgaca gacctggggg | 300 |
| gcccttcttg aggatgagag cctgttgctt ctcaagttct gtgtctaacc caggtcccca | 360 |
| ggtctacccc agcccctcgg ccctgcctgc cttgtggatg atatagttta agggtagaga | 420 |
| ccgctggcct ggagggaagg ctaggcctca ggttagggcc cagaagggag ggagaagccc | 480 |
| ttggggcagc tcccttttctg ctcactcact gcctagctcc ttccttcaca ccttccttcg | 540 |
| gaaacgtctg ctcctgacaa ggtctacttc ctgctctcag gaggccctta ttgtggagga | 600 |
| agggaggcgt cgcccgtccc tggcttctct gacagccgtg ttccatcccc gcctgtgcc | 660 |
| ccttctcccg gacagtgcct tctccagggc tcacccagga gggtgcagcg gtggccccg | 720 |
| gggcggtggt cgtggtgggg gtgttagctg caggggtgcc ctcggtgggt gggagttggt | 780 |
| ggcctctcgc tggtgccatg ggactcgcat gttcgccctg cgccctcgg ctcttgagcc | 840 |

```
cacaggccgg gatcctgcct gccagccgcg tgcgctgccg tttaacccctt gcaggcgcag      900 agcgcgcggc ggcggtgaca gagaactttg tttggctgcc caaatacagc ctcctgcaga      960
aggaccctgc gcccggggaa ggggaggaat ctcttcccct ctgggcgccc gccctcctcg     1020
ccatggcccg gcctccacat ccgcccacat ctggccgcag cggggcgccc ggggggaggg     1080
gctgaggccg cgtctctcgc cgtcccctgg gcgcgggcca ggcggggagg agggggggcgc    1140 tccggtcgtg tgcccaggac tgtccccag cggccactcg gccccagcc cccaggcct        1200 ggccttgaca ggcgggcgga gcagccagtg cgagacaggg aggccggtgc gggtgcggga     1260
acctgatccg cccggggaggc gggggcgggg cgggggcgca gcgcgcgggg aggggccggc    1320
gcccgccttc ctcccccatt cattcagctg agccagggg cctaggggct cctccggcgg      1380
ctagctctgc actgcaggag cgcgggcgcg gcgcccagc cagcgcgcag ggcccgggcc      1440
ccgccggggg cgcttcctcg ccgctgccct ccgcgcgacc cgctgccac cagccatcat      1500 gtcggacccc gcggtcaacg cgcagctgga tgggatcatt tcggacttcg aaggtgggtg    1560
ctgggctggc tgctgcggcc gcggacgtgc tggagaggac cctgcgggtg ggcctggcgc    1620
gggacggggg tgcgctgagg ggagacggga gtgcgctgag gggagacggg acccctaatc    1680
caggcgccct cccgctgaga gcgcgcgcg ccccccggccc cgtgcccgcg ccgcctacgt      1740 ggggggaccct gttagggga cccgcgtaga ccctgcgcgc cctcacagga ccctgtgctc    1800
gttctgcgca ctgccgcctg ggtttccttc cttttatttg tgtttgtgtt tgccaagcga    1860
cagcgacctc ctcgagggct cgcgaggctg cctcggaact ctccaggacg cacagtttca    1920
ctctgggaaa tccatcggtc ccctcccttt ggctctcccc ggcggctctc gggcccgct      1980 tggacccggc aacgggatag ggaggtcgtt cctcacctcc gactgagtgg acagccgcgt    2040
cctgctcggg tggacagccc tcccctcccc cacgccagtt tcggggccgc caagttgtgc    2100
agcccgtggg ccgggagcac cgaacggaca cagcccaggt cgtggcaggg tctagagtgg    2160
gatgtcccat ggccccccatc caggcctggg gatatcctca tccgcctccc agaatcgggc   2220
cgtgggggac agaagggggcc tgcgtgcggg cagggagagt attttggctc tctcctgtct    2280
tcggggttta caaagtgtgt tgggacttgc ggggctgctc tgtccaagcc tgggtctggc    2340
gtccgcgtct ctgagcctgt gagtgcgtgc gctttcctgc gtcctcttga ctgccggtgc    2400
tggggctctg cgtcctgcgt ccgcgggagt aaatacagca ggcgaagggg aagctcacac    2460
aatggtctcc agcgctctgg ggcagggctt ctgaggggcg ggcctgcctc tgccgggacc    2520
tggagccccc gccccctcgga gaggctccta ggctgacttg gcagagccc tctggtgggc    2580 cgggagggggg aaaaggctgtg ttgaaatgag caaactgtcc aggtgtcagg ccaagctggg   2640
aggtgaccag cctgaggtcc tccccgctcc atgccagaa ccaggctga catctgggtg      2700 tcctgagccc agctgcccac acggcccacc tggggtcagc cctatctgag tggggaggc     2760 gggggcctcct gggggaccag aactttggct ggacgccaag cagagtgcca gtggctgttc   2820
ttcagggctg ggcctgagga gggtgtgggg cggcgaaggg acgggagggg gttgtgatcc    2880
agtggccact ggcgctgtgc agagtgtgag ctggaaacat cgtagtta                 2928
```

<210> SEQ ID NO 94  
<211> LENGTH: 8485  
<212> TYPE: DNA  
<213> ORGANISM: Homo sapiens  
<220> FEATURE:  
<223> OTHER INFORMATION: TP53 region of interest (ROI)

<400> SEQUENCE: 94

```
cccccagccc acactcattg cagactcagg tggctgcttc ccagcacctc ctcactcacc      60
cctgcacctg ctgaccccag tagcctgcac tggcgttcac ccctcagaca cacaggtggc     120
agcaaagttt tattgtaaaa taagagatcg atataaaaat gggatataaa aagggagaag     180
gaggggaagg gtggggtgaa aatgcagatg tgcttgcaga atgtaaaaga tgttgaccct     240
tccagctgga cgtggtggct cacaattgta atcccagcac tctgggaggc tgagacaggt     300
ggatcgcctg agcccaggag tttgagacca gcctgggcaa cactgtgaga ccccatctct     360
acaaaacatg caaaagttgg ctggccatgg tggcatgaac ctgtggtccc agctactccg     420
gaggctgagg caggactgct cgagccgggg aggcaaaggc tgcagtaagc caagatcacg     480
ccactccact ccagcctggg caacaaagcg agacccagtc tcaaagaaaa agaaaaaaaa     540
aaaaaaaaaa gaaaaaagaa attgaccctg agcataaaac aagtcttggt ggatccagat     600
catcatatac aagagatgaa atcctccagg gtgtgggatg gggtgagatt cccttttagg     660
tactaaggtt caccaagagg ttgtcagaca gggtttggct gggccagcag agacttgaca     720
actccctcta cctaaccagc tgcccaactg tagaaactac caacccaccg accaacaggg     780
agagggaaca agcaccctca aggggtcaa gttctagacc ccatgtaata aaagtggtt     840 tcaaggccag atgtacatta tttcattaac cctcacaatg cactctgtga ggtaggtgca     900
aatgccagca tttcacagat atgggccttg aagttagaga aaattcaaca gtgagggaca     960
gcttccctgg ttagtacggt gaagtgggcc cctacctaga atgtggctga ttgtaaacta    1020
acccttaact gcaagaacat ttcttacatc tcccaaacat ccctcacagt aaaaaccta    1080 aaatctaagc tggtatgtcc tactccccat cctcctcccc acaacaaaac accagtgcag    1140
gccaacttgt tcagtggagc cccgggacaa agcaaatgga agtcctgggt gcttctgacg    1200
cacacctatt gcaagcaagg gttcaaagac ccaaaaccca aaatgcagg ggagggagag    1260 atggggtgg gaggctgtca gtggggaaca agaagtggag aatgtcagtc tgagtcaggc    1320
ccttctgtct tgaacatgag ttttttatgg cgggaggtag actgacccct tttggacttc    1380
aggtggctgt aggagacaga agcagggagg agagatgaca tcacatgagt gagagggtct    1440
gtgccccttt tccctgacca atgctttgaa gggcctaagg ctgggacaac gggaattcaa    1500
atcaagatgg tggccacacc ccatgcaaat atgtttactg agcacctcag agtattagtg    1560
tgtattagtc tcgtaatctt cccttacccc attttacttt atttatcttt tttgagacgg    1620
agtttcactc ttgttgccca ggctggagtg taatggtgag atctcagctc accgcaacct    1680
ctgcctcccg ggttcaagcg attctcctgc ctcagcctcc cgagtaggta gctgggatta    1740
caggcatgca tcaccacgcc cggctacttt tgtatttta gtagagatgg ggtttctcca    1800
tgttggtcag gctgggctca aactcccgac ctcaggtgat ccactcgcct tggcctccca    1860
gagtgtggga ttcgtgagcc actgcgcccg gccccttac cccatttat atataaggaa    1920 actgagtttg acggggtca cctaggacct gccggtgcat ggcagggctg agtatatgac    1980
ctgaaactct ggctgtattc agtattacac aattattagg cccctccttg agaccctcca    2040
gctctgggct gggagttgcg gagaatggca aagaagtatc cacactcgtc cctgggtttg    2100
gatgttctgt ggatacactg aggcaagaat gtggttatag gattcaaccg gaggaagact    2160
aaaaaaatgt ctgtgcaggg ctgggaccca atgagatggg gtcagctgcc tttgaccatg    2220
aaggcaggat gagaatggaa tcctatggct ttccaaccta ggaaggcagg ggagtagggc    2280
caggaagggg ctgaggtcac tcacctggag tgagccctgc tcccccctgg ctccttccca    2340
```

```
gcctgggcat ccttgagttc caaggcctca ttcagctctc ggaacatctc gaagcgctca    2400
cgcccacgga tctgcagcaa cagaggaggg ggagaagtaa gtatatacac agtacctgag    2460
ttaaaagatg gttcaagtta caattgtttg actttatgac ggtacaaaag caacatgcat    2520
ttagtagaaa ctgcacttca agtacctata cagctgactt ttaaaaatat ttatttattt    2580
attttgagat ggggtctcac tctgttgccc aggcgggagt gcaatggtgc aatcttggct    2640
gattgcaatc tccgcctctg ggttcaagt gattcttgtg cctcagcctc ccgagtagct    2700
gggactacag gcgtgtgcta ccacacctgg ctaattttg tgttttagt agagatgggg    2760 cttcaccatg ttagccaggc tggttttcaa ctcctgacgt caggtgatct acccacctcc    2820
acctcccaaa gtgctgggat tacaggtgtg agccactgtg cccggcccttt ttttaaattt    2880 tagagatgat gtcttgctat gttgttcagg ctggactcaa actcttgggc tcaagagatc    2940
ctcctgcctt agcctctcaa gtaactggga ctacatgtgc atgcgactgt gcctcgtttc    3000 ttttctttt tttctgagac ggagtctcac tctatcgccc aggctggagt gcagtggcgc    3060
catcttggct ccctgcaacc tccgcctcct ggttcaagcg attctcctgc ctcagcctcc    3120
caagtagctg ggattacagg cacctgccat cacgcccggt taattttgt attttagtag    3180 agacggggtt tcaccatgtt ggctaggctg gtcttgaact cctgacctca ggtgatccac    3240
ccgcctcagc ctcccgaaat gctgggatta caggcgtgag ccagtgcgcc tggcctttc    3300 ttttttgag tctcgctctg cgcccaggct gtgcctggct cgactgtgcc tcctttcatg    3360
caaccatgct gtttctcact ttcagtaaca atattcaata aatcacatga gatatacaac    3420
attttattac tataaaaagg gctttgtgtt agatgactttt gcccaactgt agggtaactt    3480
aaatgctctg aacacgtttc aagtaggcta gggctgagtg tggtagctca tgcctgtaac    3540
cccaatactt ggggaggctg aggtggaagg attgattgag cccaggggtt tgataccagc    3600
atgggcaacg tagcaagacc ttgacttcac agaaaataaa aaattagctg ggtgtcgtgg    3660
catgtgcctg tagtcctagc tacttgggag ggtgaaatca ccggagccca gggaggtcaa    3720
ggctgcagtg agctgagatg gtgccactgc actctagcct gagtgacaga gtgagactct    3780 gtcttaaat aaataaataa aaattagccg ggcgtggtgg ctcacacctg taatcccagc    3840
actttgggag gccgaggcgg gcggatcaca tggtcagaag ttcgagacca gcctggccaa    3900
catggtgaaa ccctgtctct actaaaaata caaaaattag ctgggcgtgg tagcaggcgc    3960
ttgtagtcct agctattcgg gaggctgagg caggagaatc acttgaaccc aggaggcaga    4020
ggttgcagtg agccgagatc atgccactgc actccagcct gggcgacaga gtgagactga    4080
gtctcaaaaa aataaaataa aataaaataa aaataaaataa ataaaaatta gccaggcatg    4140
gtggtgcagg cctgtagttg aagcaacttg ggaggctgag ctgggaggat ggatggagcc    4200
tgggaggtgg aggctgcagt gagctgtgac tgcactactg cactctatcc agcctgggtg    4260
acagagcaag accttgtctc aaaaaagtag gctagagacc agcctgggca acatagtgag    4320
actctatcta tctacaaaaa attttaaaaa ttagctgggt atggtggtgt atgcctgtgg    4380
tcctagctac tggggaggca gagttagggg gattgcttga gcccaggagg gtataatgag    4440
ctatgatcac atcactgtaa tccagcctgg gcaacagagc aagatgctgt ctccattaaa    4500
aataaaataa aagtaggcta ggcaggccgg gtgcggtggc tcacgcctgt aatcccagca    4560
ctttgggagg ccaaggcagg cagatcacaa ggtcaggagt cgagactag cctggccaac    4620 atggtgaaac ctcatctcta ctaaaaaaaa aaataaataa ataacaaaaa attagctggg    4680
cgtcggggca ggtgcctgta atcccagcta ctcagtgggc tgaggcagga gaatcgcttg    4740
```

```
aacccagaag gcggaggttg cagtgagccg agatcccgcc actgcactcc agcctgggtg    4800
acagagtgag actctgtctc caaaaaaaaa aaaaaaaaaa gcaggctagg ctaagctatg    4860
atgttcctta gattaggtgt attaaatcca ttttcaactt acaatatttt caacttacga    4920
cgagtttatc aggaagtaac accatcgtaa gtcaagtagc atctgtatca ggcaaagtca    4980
tagaaccatt ttcatgctct ctttaacaat tttctttttg aaagctggtc tggtccttta    5040
aaatatatat tatggtataa gttggtgttc tgaagttagt tagctacaac caggagccat    5100
tgtctttgag gcatcactgc cccctgatgg caaatgcccc aattgcaggt aaaacagtca    5160
agaagaaaac ggcattttga gtgttagact ggaaactttc cacttgataa gaggtcccaa    5220
gacttagtac ctgaagggtg aaatattctc catccagtgg tttcttcttt ggctggggag    5280
aggagctggt gttgttgggc agtgctagga aagaggcaag gaaaggtgat aaaagtgaat    5340
ctgaggcata actgcaccct tggtctcctc caccgcttct tgtcctgctt gcttacctcg    5400
cttagtgctc cctgggggca gctcgtggtg aggctcccct ttcttgcgga gattctcttc    5460
ctctgtgcgc cggtctctcc caggacaggc acaaacacgc acctcaaagc tgttccgtcc    5520
cagtagatta ccactactca ggataggaaa agagaagcaa gaggcagtaa ggaaatcagg    5580
tcctacctgt cccatttaaa aaaccaggct ccatctactc ccaaccaccc ttgtcctttc    5640
tggagcctaa gctccagctc caggtaggtg gaggagaagc cacaggttaa gaggtcccaa    5700
agccagagaa aagaaaactg agtgggagca gtaaggagat tccccgccgg ggatgtgatg    5760
agaggtggat gggtagtagt atggaagaaa tcggtaagag gtgggcccag gggtcagagg    5820
caagcagagg ctggggcaca gcaggccagt gtgcagggtg gcaagtggct cctgacctgg    5880
agtcttccag tgtgatgatg gtgaggatgg gcctccggtt catgccgccc atgcaggaac    5940
tgttacacat gtagttgtag tggatggtgg tacagtcaga gccaacctag gagataacac    6000
aggcccaaga tgaggccagt gcgccttggg gagacctgtg gcaagcaggg gaggcctttt    6060
tttttttttt ttgagatgga atctcgctct gtcgcccagg ctggagtgca gtggcgtgat    6120
ctcagctcac tgcaagctcc accgcccagg ttcacgccat tctccttcct cagcctcccg    6180
agtagctggg actacaggtg cccagcacca cgcccggcta attttttttt gtattttca    6240
gtagagacgg ggtttcaccg ttagccagga tggtctcgat ctcccaacct cgtgatccgc    6300
ctgccttggc ctcccaaagt gctgggatta caggcatgag ccactgcgcc cagccaagca    6360
ggggaggccc ttagcctctg taagcttcag ttttttcaac tgtgcaatag ttaaacccat    6420
ttactttgca catctcatgg ggttataggg aggtcaaata agcagcagga gaaagccccc    6480
ctactgctca cctggagggc cactgacaac caccctttaac cctcctccc agagacccca    6540
gttgcaaacc agacctcagg cggctcatag gcaccacca cactatgtcg aaaagtgttt    6600
ctgtcatcca aatactccac acgcaaattt ccttccactc ggataagatg ctgaggaggg    6660
gccagaccta agagcaatca gtgaggaatc agaggcctgg ggaccctggg caaccagccc    6720
tgtcgtctct ccagccccag ctgctcacca tcgctatctg agcagcgctc atggtggggg    6780
cagcgcctca caacctccgt catgtgctgt gactgcttgt agatggccat ggcgcggacg    6840
cgggtgccgg gcggggtgt ggaatcaacc cacagctgca cagggcaggt cttggccagt    6900
tggcaaaaca tcttgttgag ggcaggggag tactgtagga agaggaagga gacagagttg    6960
aaagtcaggg cacaagtgaa cagataaagc aactggaaga cggcagcaaa gaaacaaaca    7020
tgcgtaagca cctcctgcaa cccactagcg agctagagag agttggcgtc tacacctcag    7080
```

```
                                                        -continued
gagcttttct ttttttttttt tttttttgag atagggtctt gctctgtcac tcaggctgga    7140
gcacagtggt gtgatcacag ctcactgcag cctccatctc ctggcctcaa gtgatcttcc    7200
cacctcagcc tcctaagtgg ctgggactat aggtgtgcac caccatgcct ggctaatttt    7260 ttgtatttt  ttgtagagac gaggtttcat catgttaccc aggctggtct tgaactcctg    7320
ggctcaggtg atctgcctgc cttggcctct ttgagagtgc tgggattgca ggtgtgagcc    7380
accaagcctg gtcaggagct tattttcaaa agccaaggaa tacacgtgga tgaagaaaaa    7440
gaaaagttct gcatccccag gagagatgct gagggtgtga tgggatggat aaaagcccaa    7500
attcaagggg ggaatattca actttgggac aggagtcaga gatcacacat taagtgggta    7560
aactataaaa aaacactgac aggaagccaa agggtgaaga ggaatcccaa agttccaaac    7620
aaaagaaatg caggggggata cggccaggca ttgaagtctc atggaagcca gcccctcagg    7680
gcaactgacc gtgcaagtca cagacttggc tgtcccagaa tgcaagaagc ccagacggaa    7740
accgtagctg ccctggtagg ttttctggga agggacagaa gatgacaggg gccaggaggg    7800
ggctggtgca ggggccgccg gtgtaggagc tgctggtgca ggggccacgg ggggagcagc    7860
ctctggcatt ctgggagctt catctggacc tgggtcttca gtgaaccatt gttcaatatc    7920
gtccggggac agcatcaaat catccattgc ttgggacggc aaggggggact gtagatgggt    7980 gaaagagca gtcagaggac caggtcctca gcccccagc  cccccagccc tccaggtccc    8040
cagccctcca ggtccccagc ccaacccttg tccttaccag aacgttgttt tcaggaagtc    8100
tgaaagacaa gagcagaaag tcagtcccat ggaattttcg cttcccacag gtctctgcta    8160
gggggctggg gttggggtgg gggtggtggg cctgcccttc caatggatcc actcacagtt    8220
tccataggtc tgaaaatgtt tcctgactca gagggggctc gacgctagga tctgactgcg    8280
gctcctccat ggcagtgacc cggaaggcag tctggctgct gcaagaggaa aagtgggat     8340 ccagcatgag acacttccaa ccctgggtca cctgggcctg cagagaagga accccctccc    8400
ccaacaccat gccagtgtct gagacagctc ggcttcctgt ggagcaggaa aagaatggct    8460
gcttcacatt ctctcttcca atgtt                                         8485
```

METHOD FOR DETERMINING A MUTATION IN GENOMIC DNA, USE OF THE METHOD AND KIT FOR CARRYING OUT SAID METHOD

CROSS-REFERENCE TO RELATED APPLICATIONS

This patent application is a § 371 national stage entry of PCT/EP2016/001237, filed Jul. 15, 2016, which claims priority of German [patent application no.] Patent Application No. 10 2015 009 187.5, filed Jul. 16, 2015, the entire disclosure of which is [hereby] incorporated herein by reference.

SEQUENCE LISTING

The instant application contains a Sequence Listing which has been submitted electronically in ASCII format and is hereby incorporated by reference in its entirety. Said ASCII copy, created on Oct. 2, 2019, is named Hansepatent-3PUS_SL.txt and is 95,733 bytes in size.

SEQUENCE LISTING

This application contains an electronic sequence listing in txt-format according to WIPO ST.25 standard with 94 sequences as part of the description.

FIELD OF THE INVENTION

This invention relates to molecular diagnostic methods in the field of oncology for the determination of mutations in genomic DNA. The invention also relates to use of such molecular diagnostic methods in connection with the diagnosis, prognosis, prediction and monitoring of malignant diseases. Furthermore, the invention relates to a kit for carrying out the specified methods or for the specified uses. In particular, the methods of the present invention relate to in vitro methods.

BACKGROUND OF THE INVENTION

In the age of personalized medicine, targeted therapies are of paramount importance. In the field of oncology, several drugs are already successfully used to inhibit specific proteins that are mutated in tumors. One example is the drug Vemurafenib (common name: Zelboraf), which selectively inhibits the BRAF oncogene. This gene is mutated in about 70% of malignant melanoma tumors. The mutation leads to an increased activity of the resulting gene product. Patients whose tumors have such a mutation therefore respond well to therapy with the BRAF inhibitor Vemurafenib. The mutation of BRAF is thus a predictive biomarker for response to Vemurafenib treatment. Therefore, the determination of a mutation of BRAF is nowadays established as a routine diagnostic procedure in order to identify patients for whom Vemurafenib can be used.

Another example of such a targeted therapy, in which the mutation status of a gene is relevant, is the drug Cetuximab (common name: Erbitux). Cetuximab selectively inhibits the epidermal growth factor receptor (EGFR) and is used, for example, in the treatment of metastatic colorectal cancer. However, this drug is not effective if another gene (KRAS) in the signaling pathway has a mutation. Therefore, determination of a KRAS mutation is predictive for the patient's non-response to treatment with Cetuximab.

The determination of a mutation of the corresponding genes therefore plays a decisive role. This is usually done by DNA sequencing. For this purpose, a surgically removed tumor or a biopsy of the tumor is usually assessed pathologically and the tumor tissue contained in the tissue sample is marked. If the sequencing is afterwards negative in the tumor material identified by the pathologist, it is shown that the mutation is absent. If the sequencing result is positive, then the presence of the mutation is proven.

The problem is that sample material can be incorrectly identified, treated or analyzed at every stage of the diagnostic chain, which can lead to false-negative results. For example, it is possible that the histopathologist identifies healthy normal tissue as tumor material or that too much healthy normal tissue is carried over into the further analytical work flow. Under such conditions, it is usually difficult or even impossible to detect a mutation on a molecular level. Under certain circumstances, the assessment of the sample material by several pathologists can provide improvement. However, this leads to longer processing time and higher personnel expenses, resulting in higher costs. Furthermore, it does not eliminate the risk that the tumor contains only a small proportion of neoplastic cells or that the tumor cells are scattered in normal tissue, so that the molecular analysis can produce false-negative results despite careful assessment. Incorrect molecular diagnostic results can have fatal consequences. In the worst-case scenario, patients who can be treated or need treatment do not receive the appropriate therapy or do not receive any therapy at all. On the other hand, it is also possible that patients receive unnecessary therapies or receive therapy at a wrong time.

It is therefore an object of the present invention to provide methods and uses thereof as well as kits that allow a robust, in particular more sensitive and/or more specific, and cost effective molecular diagnosis of mutations or malignant diseases, respectively, and support a more differentiated clinical decision-making, thus at least partially reducing or solving the aforementioned problems.

SUMMARY OF THE INVENTION

In a first aspect of the invention, this object is solved by a method for determining at least one mutation in genomic DNA. The method of the invention is characterized in that the mutation analysis is carried out with genomic DNA, in which at least part of the cytosines contained therein has previously been converted into uracil or another base with a base pairing behavior and/or molecular weight that is distinguishable from that of cytosine.

According to a second aspect of the invention, this object is solved by using the method of the first aspect for diagnosis, prognosis, prediction and/or monitoring of a malignant disease.

In a third aspect of the invention, this object is solved by a kit for carrying out the method of the first aspect or for the use of the second aspect, respectively.

Preferred variants of these aspects will become apparent from the description and the dependent claims.

Definitions and General Explanations

In this description, various documents are cited in order to provide a general technical background in relation to the present invention. The disclosures and teachings of these documents are hereby incorporated by reference in their entirety to supplement the following description, in order to avoid repetition.

The following definitions and general explanations are intended to guide and support the skilled reader in understanding, interpreting and practicing the present invention. Unless indicated otherwise, all technical and scientific terms shall have the meaning which corresponds to the usual understanding of one of ordinary skill in the art in the field of the present invention.

The various aspects and variants of the present invention involve techniques and methods that are routinely practiced in molecular biology. Useful laboratory manuals for these techniques and methods are readily available for the skilled person, such as "Molecular Cloning, A Laboratory Manual" by M. R. Green and J. Sambrook, 4th Edition, 2012, Cold Spring Harbor Laboratory Press; "Next-Generation Sequencing: Current Technologies and Applications" by Jianping Xu, 2014, Caister Academic Press; "Next-Generation DNA Sequencing Informatics" by Stuart M. Brown, 2nd Edition, 2015, Cold Spring Harbor Laboratory Press.

The design of primers and oligonucleotide probes is part of the technical knowledge of a molecular biologist or molecular geneticist. A suitable algorithm which enables the design of primers and probes for converted (bisulfite-converted) DNA is MethPrimer (Li, L. C. and Dahiya, R., Bioinformatics, 2002, 18, 1427-31). BiSearch (Tusnddy, G. E. et al., Nucleic Acids Research, 2005, 33, e9) is another suitable primer design algorithm that is suitable for both converted (bisulfite-converted) as well as for genomic unconverted DNA.

MethBlast (Pattyn, F. et al., BMC Bioinformatics 2006, 7, 496) is a search program for the analysis of in silico converted (bisulfite-converted) DNA, both in methylated as well as in unmethylated state. This program is particularly designed for determining primer binding sites and thus the optimization of the specificity of PCR-amplifications.

As used herein, indefinite articles such as "a" or "an" include the possibility that two or more of these features may also exist.

Herein, a "gene" is defined as a section of DNA that includes regulatory, transcribed and/or functional sequence regions and thus contains the basic information for the production of a biologically active RNA.

The nomenclature for the designation of genes and their nucleotides is based on the recommendation of the "Human Genome Organization Gene Nomenclature Committee" (HGNC) as of Jun. 30, 2015. For example, a gene stem is designated with italic Latin capital letters (e.g., EGFR, BRAF). Where applicable, the stem symbol is followed by one or more Arabic numerals or a combination of Arabic numerals and Latin letters to denote a family member of the gene stem (e.g., BRCA1, BRCA2, SHOX2).

The description of genes at the DNA level, for example the denotation of nucleotides, sequence variations and mutations, follows the "Human Genome Variation Society" (HGVS) recommendations for the description of sequence variants as of Jun. 30, 2015 (den Dunnen, J. T. and Antonarakis, S. E., Human Mutation, 2000, 15, 7-12).

The genes described herein are publicly available from the "GenBank" of the National Institute of Health, USA, as from Jun. 30, 2015 (Benson, D. A. et al., Nucleic Acids Research, 2013, 41, D36-42).

If, in the following, reference is made to "at least 95% sequence identity", higher sequence identities such as at least 96%, at least 97%, at least 98%, at least 99% or 100% sequence identity are also included. The sequence identity of two nucleic acid sequences can be determined, for example, using the algorithm ClustalW (Thompson et al., Nucleic Acids Research, 1994, 22, 4673-4680).

For the purpose of the invention, "genomic DNA" means any part of the DNA that at least partially forms or has formed the genome of one or more cells. In particular, genomic DNA also includes cell-free DNA, such as circulating DNA that has been released from one or more cells of a tumor. Accordingly, "genomic DNA" also includes DNA isolated from cells and purified if necessary.

A "mutation" comprises a permanent change in the genetic material, the origin of which lies in a single cell and which is then passed on to the daughter cells. In several variants of the invention, a "mutation" includes a gene mutation, such as a point mutation, deletion, insertion, duplication, amplification, translocation, fusion or inversion. In certain variants of the invention, a mutation can be characterized by an allele frequency of less than or equal to 1% in the world population, and is thus to be distinguished from a polymorphism, which by definition has an allele frequency of more than 1% in the world population.

As the term is used here, a mutation also includes the integration of DNA of viral origin into genomic DNA in the sense of an insertion mutation. Non-limiting examples of such viruses which have the ability to integrate into the genome of the infected cell and cause insertion mutations are the Epstein-Barr virus (EBV), the hepatitis B virus (HBV), human papillomaviruses (HPV), the human T-lymphotropic virus 1 (HTLV-1), and the Merkel cell polyomavirus (MCPyV).

Accordingly, a "mutation analysis" comprises an investigation as to whether such a change in the genetic material is present, and if so, in which form or to which extent. In several variants of the invention, this can be determined, for example, by a deviation of the base sequence, the molecular weight, the hybridization strength or another suitable property of a section of the genomic DNA to be analyzed from a standard value. A suitable standard value is, for example, the corresponding property, in particular the base sequence, of a corresponding section of a genomic DNA that does not have said change, in the following also referred to as wild type, wild typical state or reference DNA. A suitable wild type is, for example, genomic DNA from normal tissue, in particular healthy tissue, of the same individual. For example, this can be the preferred wild type for determining a somatic mutation. A reference genome can also be used as a wild type. A suitable reference genome includes the human genome version of the Genome Reference Consortium Human Build 38 patch release 2 (GRCh38.p2) as of Jul. 16, 2015. A reference genome may be the preferred wild type with respect to the determination of a germline mutation and/or a somatic mutation. In certain variants, "mutation analysis" means the determination of whether the genomic DNA to be analyzed differs in base sequence from a wild typical DNA, in particular from a specific gene or a specific sequence of the wild typical DNA. These variants explicitly include cases wherein the mutation analysis encompasses a deviation in only a part of the gene or the specific sequence from the wild type DNA in order to determine the mutation.

A "polymorphism" is understood as the occurrence of several gene variants resulting from sequence variations within a population. A polymorphism pertains to the germline, can be inherited from one individual to another and occurs equally in all cells of an organism. In contrast to a sequence variation or germline mutation, the rarer gene variant must by definition have a frequency of occurrence (allele frequency) of more than one percent within a population.

The "germline" is the cell sequence (genealogy) from which the germ cells (generative cells, gametes) emerge. The somatic cell lines that descend from the germline constitute the body (the soma). Accordingly, a "germline mutation" is to be understood as a mutation that occurs in the cells of the germline of an organism, pertains to all cells of the organism equally and can be inherited from one individual to another. Conversely, a "somatic mutation" is a mutation that occurs outside of the germline, i.e. in cells of the soma (somatic cells). This mutation affects only part of the cells of an organism, such as tumor cells. This type of mutation cannot be inherited from one individual to another.

A "recurrent mutation" is a mutation that occurs very often in a specific malignant disease. In particular, a mutation is recurrent when it occurs in at least 1%, at least 3% or at least 10% of cases of this specific malignant disease. A "recurrently mutated gene" is to be understood as a gene that very often has at least one mutation in a specific malignant disease. In particular, a gene is recurrently mutated when it contains at least one mutation in at least 5%, at least 10% or at least 20% of cases of the specific malignant disease.

A "CpG dinucleotide" is a DNA motif which has the nucleoside sequence cytidine-phosphate-guanosine in the general reading direction from 5' to 3'. Guanosine consists of the nucleobase guanine and the sugar R-D-ribose. Cytidine consists of the nucleobase cytosine and the sugar R-D-ribose.

A "methylation analysis" in the sense of the present invention comprises determining the methylation state of a CpG dinucleotide or several CpG dinucleotides within a particular sequence context. In various variants of the present invention, "methylation analysis" means the determination whether the cytosine in the CpG dinucleotide(s) is methylated. The methylation analysis may include a single copy of the CpG dinucleotide. The methylation analysis can also include a plurality of copies of the CpG dinucleotide, for example if the DNA of a plurality of cells is present in the genomic DNA. In this case, the methylation analysis can provide a methylation status or methylation value of the CpG dinucleotide, i.e. an average value that incorporates the methylation state of the plurality of copies of the CpG dinucleotide.

A CpG dinucleotide can be "aberrantly methylated" in a tissue or cell type or have an "aberrant methylation state", which means a CpG dinucleotide which is hypermethylated or hypomethylated in the genomic DNA compared to a standard value. A suitable standard value is, for example, the methylation state of the corresponding CpG dinucleotide in the genomic DNA of the same tissue or cell type, wherein said tissue or cell type differs in a property with respect to which the CpG dinucleotide is "aberrantly methylated". For example, genes are "aberrantly methylated" that have a higher or lower methylation in tumor cells than in the tissue from which the tumor originated. The "aberrant methylation state" is maintained when the genomic DNA is released from the tumor or cell, for example in the form of circulating DNA into the blood. Suitable standard values can thus be determined experimentally, for example by carrying out a methylation analysis of the same cell type or tissue type, but which does not have the property with respect to which the at least one CpG dinucleotide is to be determined as "aberrantly methylated". Hence, hypermethylated and hypomethylated can denote a higher or lower methylation compared to the standard value. Hypermethylated CpG dinucleotides have a methylation value that is higher than the standard value, in particular that is at least 25% higher than the standard value. Hypomethylated CpG dinucleotides have a methylation value that is lower than the standard value, in particular that is at least 25% lower than the standard value. If however the standard value of a certain CpG dinucleotide is zero, then said certain CpG dinucleotide is not hypomethylated.

"Malignant" diseases include diseases that are characterized by a course of disease that is progressively destructive and may also lead to the death of the patient. Malignant diseases include malignant formation of new tissue, such as neoplasia or tumors, where malignancy may be characterized by uncontrolled, space-consuming, displacing, infiltrative and/or invasive growth. Malignant tumors are usually able to form secondary tumors (metastases). Malignant tumors include for example carcinomas, sarcomas, melanomas, blastomas and teratomas. Malignant diseases also include hematological malignancies, i.e. malignant diseases affecting the blood system or the hematopoietic system, such as leukemias, lymphomas, myeloproliferative disorders and myelodysplastic syndromes. Leukemias include a group of malignant diseases in which immature hematopoietic cells have changed malignantly, proliferate excessively and lead to an accumulation of cells in the peripheral bloodstream. Lymphomas comprise diseases in which cells of the lymphatic system are malignantly degenerated. Myeloproliferative disorders comprise a group of diseases in which one or more hematopoietic cell lines proliferate excessively. Myelodysplastic syndromes comprise a clonal expansion of progenitor cells of all hematopoietic cell lines, which is based on a chronic differentiation disorder of the hematopoietic stem cells.

Biomarkers are characteristic indicators and/or biological features that can be measured objectively and allow conclusions to be drawn with respect to the status of a normal biological or pathological process in an organism, or the response of a normal or pathological process to an intervention, such as surgery, irradiation or drug treatment. Biomarkers are often (bio-)chemical substances, such as proteins, hormones, metabolites, sugars and nucleic acids, as well as modifications thereof.

As the terms are used herein, "diagnosis" includes detection or determination of a malignant disease, "prognosis" an estimation of the development of a malignant disease in the future, especially in absence of a therapeutic invention, "prediction" a forecast of the response behavior of a malignant disease to a particular therapy, and "monitoring" a determination of a state of a malignant disease at different points in time, for example prior to, during and after therapy. In particular, these terms refer to deductive steps in connection with a preceding in vitro procedure, so that no essential technical step of the present invention is practiced on the human or animal body.

Both the above general description as well as the following detailed description are to be understood as examples and are intended to illustrate the claimed invention. Further advantages and features of the invention are evident from the following description, the drawings and the claims. Even if the invention is described on the basis of preferred embodiments, many other variations can be made without departing from the scope of the present invention. Therefore, it is intended that the claims cover variations and combinations of features that are included in the actual scope of the invention, even if they are not expressly mentioned in the claims.

BRIEF DESCRIPTION OF THE SEQUENCES

Figure 1:
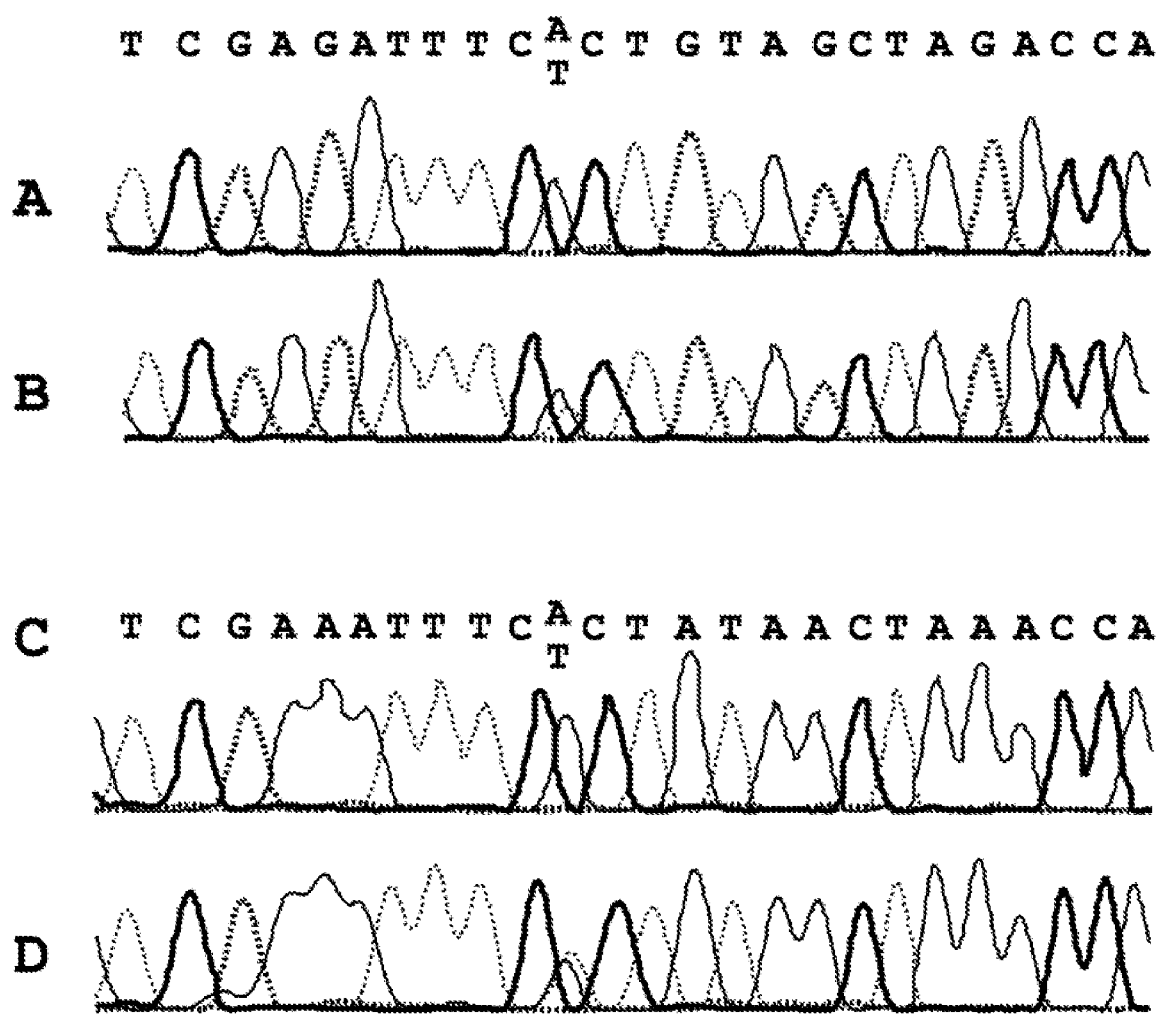
FIG. 1 shows the result of a reference analysis of a sequence of the BRAF gene with unconverted genomic DNA from normal tissue (A) and malignant tissue (B) as well as the result of the analysis according to the present invention of the sequence of the BRAF gene with converted genomic DNA from normal tissue (C) and malignant tissue (D).

SEQ ID NO:1 forward primer used for amplification of the unconverted (SEQ ID NO:3) and the converted (SEQ ID NO:4) BRAF V600E locus.

SEQ ID NO:2 reverse primer used for amplification of the unconverted (SEQ ID NO:3) and the converted (SEQ ID NO:4) BRAF V600E locus.

SEQ ID NO:3 BRAF gene locus comprising the position of the V600E mutation.

SEQ ID NO:4 converted BRAF gene locus (bisulfite-II strand) comprising the position of the V600E mutation.

SEQ ID NO:5 qPCR detection probe targeting the bisulfite converted BRAF gene locus (SEQ ID NO:4) comprising the V600E mutation.

SEQ ID NO:6 SHOX2 gene locus, which was investigated in methylation analyses.

SEQ ID NO:7 forward primer used for amplification of the converted SHOX2 gene locus (SEQ ID NO:10).

SEQ ID NO:8 reverse primer used for amplification of the converted SHOX2 gene locus (SEQ ID NO:10).

SEQ ID NO:9 blocker oligonucleotide used to prevent the forward primer (SEQ ID NO:7) from binding to the converted SHOX2 gene locus (SEQ ID NO:10) when it is unmethylated.

SEQ ID NO:10 converted (bisulfite-I strand) SHOX2 gene locus derived from the genomic sequence SEQ ID NO:6.

SEQ ID NO:11 qPCR detection probe targeting the converted methylated SHOX2 gene locus (SEQ ID NO:10).

SEQ ID NO:12 sequencing primer used for the Sanger sequencing of the converted BRAF gene locus (SEQ ID NO:4).

SEQ ID NO:13 forward primer used to amplify the unconverted EGFR exon 21 gene locus (SEQ ID NO:15) comprising the L858R mutation.

SEQ ID NO:14 reverse primer used to amplify the unconverted EGFR exon 21 gene locus (SEQ ID NO:15) comprising the L858R mutation.

SEQ ID NO:15 unconverted EGFR Exon 21 gene locus comprising the L858R mutation.

SEQ ID NO:16 forward primer used to amplify the converted EGFR exon 21 gene locus (SEQ ID NO:18) comprising the L858R mutation.

SEQ ID NO:17 reverse primer used to amplify the converted EGFR exon 21 gene locus (SEQ ID NO:18) comprising the L858R mutation.

SEQ ID NO:18 converted EGFR exon 21 gene locus (bisulfite-I strand) derived from SEQ ID NO:15 comprising the L858R mutation.

SEQ ID NO:19 forward primer used to amplify the unconverted EGFR exon 19 gene locus (SEQ ID NO:21).

SEQ ID NO:20 reverse primer used to amplify the unconverted EGFR exon 19 gene locus (SEQ ID NO:21).

SEQ ID NO:21 unconverted EGFR exon 19 gene locus.

SEQ ID NO:22 forward primer used to amplify the converted EGFR exon 19 gene locus (SEQ ID NO:24).

SEQ ID NO:23 reverse primer used to amplify the converted EGFR exon 19 gene locus (SEQ ID NO:24).

SEQ ID NO:24 converted EGFR Exon 19 gene locus (bisulfite-I strand) derived from SEQ ID NO:21.

SEQ ID NO:25 forward primer used to amplify the unconverted KRAS exon 4 gene locus (SEQ ID NO:27).

SEQ ID NO:26 reverse primer used to amplify the unconverted KRAS exon 4 gene locus (SEQ ID NO:27).

SEQ ID NO:27 unconverted KRAS exon 4 gene locus.

SEQ ID NO:28 converted KRAS exon 4 gene locus (bisulfite-I strand) derived from SEQ ID NO:27.

SEQ ID NO:29 forward primer used to amplify the converted KRAS exon 4 gene locus (SEQ ID NO:28).

SEQ ID NO:30 reverse primer used to amplify the converted KRAS exon 4 gene locus (SEQ ID NO:28).

SEQ ID NO:31 converted KRAS exon 4 gene locus (bisulfite-II strand) derived from SEQ ID NO:27.
SEQ ID NO:32 forward primer used to amplify the converted KRAS exon 4 gene locus (SEQ ID NO:31).
SEQ ID NO:33 reverse primer used to amplify the converted KRAS exon 4 gene locus (SEQ ID NO:31).
SEQ ID NO:34 BRCA2, "Region of Interest" (ROI) 1.
SEQ ID NO:35 BRCA2, ROI 2.
SEQ ID NO:36 BRCA2, ROI 3.
SEQ ID NO:37 BRCA2, ROI 4.
SEQ ID NO:38 BRCA2, ROI 5 SEQ ID NO:39 BRCA2, ROI 6, preferred for methylation analyses.
SEQ ID NO:40 BRCA2, ROI 7.
SEQ ID NO:41 BRCA2, ROI 8.
SEQ ID NO:42 BRCA2, ROI 9.
SEQ ID NO:43 BRCA2, ROI 10.
SEQ ID NO:44 BRCA2, ROI 11.
SEQ ID NO:45 BRCA2, ROI 12.
SEQ ID NO:46 BRCA1, "Region of Interest" (ROI) 1.
SEQ ID NO:47 BRCA1, ROI 2.
SEQ ID NO:48 BRCA1, ROI 3.
SEQ ID NO:49 BRCA1, ROI 4.
SEQ ID NO:50 BRCA1, ROI 5.
SEQ ID NO:51 BRCA1, ROI 6.
SEQ ID NO:52 BRCA1, ROI 7.
SEQ ID NO:53 BRCA1, ROI 8.
SEQ ID NO:54 BRCA1, ROI 9.
SEQ ID NO:55 BRCA1, ROI 10.
SEQ ID NO:56 BRCA1, ROI 11, preferred for mutation analyses.
SEQ ID NO:57 BRCA1, ROI 12.
SEQ ID NO:58 BRCA1, ROI 13.
SEQ ID NO:59 BRCA1, ROI 14.
SEQ ID NO:60 BRCA1, ROI 15.
SEQ ID NO:61 BRCA1, ROI 16, preferred for methylation analyses.
SEQ ID NO:62 BRCA1, ROI 17.
SEQ ID NO:63 BRCA1, ROI 18.
SEQ ID NO:64 EGFR, "Region of Interest" (ROI) 1, exon 19.
SEQ ID NO:65 EGFR, ROI 2, exon 21.
SEQ ID NO:66 EGFR, ROI 3, exon 20.
SEQ ID NO:67 EGFR, ROI 4, exon 18.
SEQ ID NO:68 KRAS, "Region of Interest" (ROI) 1, exon 2.
SEQ ID NO:69 KRAS, ROI 2, exon 3.
SEQ ID NO:70 KRAS, ROI 3, exon 4.
SEQ ID NO:71 BRAF, "Region of Interest" (ROI) 1, exon 15.
SEQ ID NO:72 BRAF, ROI 2, exon 11.
SEQ ID NO:73 AKT1, "Region of Interest" (ROI) 1.
SEQ ID NO:74 DDR2, "Region of Interest" (ROI) 1, exon 19.
SEQ ID NO:75 DDR2, ROI 2, exon 18.
SEQ ID NO:76 DDR2, ROI 3, exons 16 and 17.
SEQ ID NO:77 ERBB2 (HER2), "Region of Interest" (ROI) 1.
SEQ ID NO:78 MAP2K1 (MEK1), "Region of Interest" (ROI) 1.
SEQ ID NO:79 NRAS, "Region of Interest" (ROI) 1, codon 61.
SEQ ID NO:80 NRAS, ROI 2, codon 12.
SEQ ID NO:81 PIK3CA, "Region of Interest" (ROI) 1, exon 9.
SEQ ID NO:82 PIK3CA, ROI 2, exon 20.
SEQ ID NO:83 PTEN, "Region of Interest" (ROI) 1, exon 7.
SEQ ID NO:84 IDH1, "Region of Interest" (ROI) 1.
SEQ ID NO:85 IDH2, "Region of Interest" (ROI) 1.
SEQ ID NO:86 forward primer (F1) suitable for BRCA1 methylation analyses.
SEQ ID NO:87 reverse primer (R1) suitable for BRCA1 methylation analyses.
SEQ ID NO:88 forward primer (F2) suitable for BRCA1 methylation analyses.
SEQ ID NO:89 reverse primer (R2) suitable for BRCA1 methylation analyses.
SEQ ID NO:90 PITX2, "Region of Interest" (ROI) 1, promotor A, preferred for methylation analyses.
SEQ ID NO:91 PITX2, ROI 2, promotor C, preferred for methylation analyses.
SEQ ID NO:92 MGMT, "Region of Interest" (ROI) 1, preferred for methylation analyses.
SEQ ID NO:93 SEPT9, "Region of Interest" (ROI) 1, preferred for methylation analyses.
SEQ ID NO:94 TP53 "Region of Interest" (ROI) 1.

DESCRIPTION OF THE INVENTION

The first aspect of the present invention relates to a method for determining at least one mutation in genomic DNA. The method comprises the following steps: A) converting at least a part of the cytosines contained in the genomic DNA into uracil or another base having a base pairing behavior and/or molecular weight distinguishable from that of cytosine, B) performing a mutation analysis with the genomic DNA obtained from step A) to determine the at least one mutation. The genomic DNA obtained from step A) is hereinafter also referred to as "converted DNA". Accordingly, "unconverted DNA" means genomic DNA that has not passed through step A).

The present invention is based, among other things, on the inventor's insight that many clinically relevant samples, such as biopsies, fine needle aspirates, laser-microdissected cells, blood plasma or circulating tumor cells, only contain very small amounts of genomic DNA, whereas at the same time an ever-increasing number of genetic parameters is required in clinical routine for personalized and optimized treatment of the patient. Blood plasma, for example, often contains only a few hundred to several thousand copies of circulating cell-free DNA per milliliter of plasma. Circulating tumor cells even occur only in the order of a few single cells up to several dozen tumor cells per 10 milliliters of whole blood. With laser-microdissected cells, the amount of DNA depends on the number of microdissected cells and can range from a single cell with two DNA copies to more than 1000 cells. Laser-microdissection is often performed with formalin-fixed and paraffin-embedded samples, in which the majority of DNA is degraded and therefore not available for molecular diagnostic testing. The problem is that the genomic DNA cannot usually be recovered unchanged or not recovered at all after performing a conventional molecular diagnostic procedure. Therefore, additional molecular diagnostic procedures or repetitions of molecular diagnostic procedures are not possible.

Such an additional molecular diagnostic method is methylation analysis, in which the genomic DNA must first be converted, for example by bisulfite treatment. For example, unmethylated cytosine is converted to uracil, while methylated cytosine (methylcytosine, meC) remains unchanged. Uracil has the same base pairing properties as thymine. Therefore, it is not possible to differentiate between the two during a subsequent amplification of the converted genomic DNA. Accordingly, a C to U conversion takes place, which behaves like a C to T conversion due to the same base pairing behavior of T and U. Consequently, the conversion of cytosine greatly reduces the sequence complexity of DNA, which leads to a considerable loss of genetic information. For this reason, a molecular physician has so far been forced to decide which analysis is to be carried out, for example either a mutation analysis or a methylation analysis, especially in the case of small and very small samples.

The mutation analysis of the present invention that is performed with converted DNA solves this problem. Although the conversion of genomic DNA for the purpose of methylation analysis has been known for about a quarter of a century (Frommer, M. et al., Proc. Natl. Acad. Sci. USA, 1992, 89, 1827-1831), experts have not been able to show in this long time that it is also possible to analyze mutations in converted DNA. Rather, the teaching prevailed that the loss of genetic information through the conversion of genomic DNA makes it difficult if not impossible to determine a mutation, especially if cytosines are affected by mutations.

This view, which is widespread among experts, was overcome in the course of this invention. It has been shown for the first time that it is possible to analyze mutations in converted DNA. This inventive insight results in various unexpected advantages. For example, mutation analysis in converted DNA according to the present invention for the first time allows direct combination of the mutation analysis with further analyses such as methylation analysis within the same sample. In this way, various clinically relevant genetic and epigenetic parameters can be highly multiplexed and analyzed in parallel. This does not only lead to a more cost-efficient molecular diagnosis of diseases, but also enables more differentiated clinical decision-making and shorter analysis times. Surprisingly, it has also been found that certain mutations can be analyzed even better than with a conventional mutation analysis with unconverted genomic DNA. In this regard, reference is also made to the examples below.

The genomic DNA can be obtained from different sources, for example from cells of surgically or bioptically excised tissues. The cells can also be derived from swabs and aspirates such as rinsing fluids, fine needle aspirates or sputum. The genomic DNA can also be obtained from blood, blood serum and blood plasma, for example in the form of circulating cell-free DNA, exosomal DNA, or in the form of circulating cells from which the genomic DNA is extracted. The genomic DNA can also originate from other body fluids such as urine, pleural effusions or ascites, for example in the form of free DNA or cells from which the genomic DNA is extracted. The DNA can be obtained from non-preserved (fresh) cells, tissues and body fluids as well as from fixed cells, tissues and body fluids. The fixation of cells, tissues and body fluids can be achieved by precipitating fixatives such as ethanol and other alcohols or by cross-linking fixatives such as formaldehyde. The genomic DNA can also originate from any combination of these sources. It can also be extracted DNA from the sources mentioned above. It is also possible to enrich the genomic DNA, for example by precipitation or extraction. This can be beneficial, for example, in the case of circulating cell-free genomic DNA from the aforementioned body fluids. It is also possible to enrich the cells, for example by size filtration or surface bound antibodies (e. g. to magnetic particles, membranes or polymers) whose antigens are located on the surface of the cells to be enriched, such as an anti-EpCAM antibody. This may be a preferable solution, for example, in the case of circulating cells from the body fluids mentioned above. A suitable device for enriching circulating cells from the bloodstream of a patient is described in WO 2010/145824 A1, for example, which is hereby incorporated by reference in its entirety to more fully describe the technical background of this invention. Corresponding commercially available devices are for example the CellCollector detector CANCER01 (DC01) and the detector CANCER02 (DC02) (both GILUPI GmbH, Potsdam, Germany). Other suitable sources of genomic DNA are lysates or homogenizates of fresh tissue and lysates of fixed tissues.

In principle, the conversion of the genomic DNA in step A) can be carried out using any state-of-the-art method known and suitable for this purpose. This is typically a chemical or enzymatic conversion, for example by contacting the genomic DNA with bisulfite, for example sodium bisulfite or ammonium bisulfite, or with cytidine deaminases.

If necessary, the genomic DNA obtained from step A) can be purified after the conversion in step A) and before the mutation analysis in step B). Suitable purification methods and protocols are known to one of ordinary skill in the art and can include, for example, DNA extraction, precipitation or polymer-mediated enrichment.

The type of mutation analysis in step B) is not particularly limited. A skilled person can easily determine suitable methods on the basis of this disclosure. In this regard, reference is also made to the above-mentioned laboratory manuals. In a preferred variant, a polymerase chain reaction (PCR) is first carried out using oligonucleotides, so-called primers, which is designed to amplify a portion of the converted genomic DNA that is suspected of containing the mutation. Subsequently, at least part of the amplicon is preferably sequenced, e. g. by Sanger sequencing, pyrosequencing, mass spectrometric sequencing or a sequencing of the second or third generation, which are also referred to as "Massive Parallel Sequencing", "Next Generation Sequencing" (NGS) or as nanopore sequencing. It is also possible to perform a hybridization with mutation-specific oligonucleotides (probes) after PCR, for example in the form of a DNA microarray. The mutation can also be determined by quantitative real-time PCR (quantitative real-time PCR, qPCR), optionally followed by a melting curve analysis. The mutation can also be determined by modified PCR-based methods such as ARMES (Amplification Refractory Mutation System).

In other preferred variants, however, a PCR step can be omitted, for example in the case of "Whole Genome Shotgun Bisulfite Sequencing" (WGSBS) or direct nanopore sequencing. In WGSBS, the DNA is fragmented and adapters are then ligated to the DNA fragments. Amplification and sequencing is then possible via the adapters. It is also possible to omit the step of fragmentation in the WGSBS, since the DNA may already be fragmented, e. g. through conversion by bisulfite treatment. Protocols for the implementation of a WGSBS are easily accessible to a skilled person (Johnson, M. D. et al., Curr. Protoc. Mol. Biol. 2012, 99, 21.23.1-21.23.28; Lister, R. et al., Nature, 2009, 462, 315-322; Berman, B. P. et al., Nat. Genet, 2011, 44, 40-46).

In the case of nanopore sequencing, a DNA molecule is passed through a pore. During passage, the nucleotides trigger a measurable electrical signal which is characteristic of the nucleotides in the nanopore and can thus be assigned to them.

In another preferred variant, a hybridization with specific oligonucleotides (probes) can be performed prior to PCR amplification, which are ligated in the case of binding and subsequently amplified by PCR. Suitable methods and protocols, such as a "multiplex ligation dependent probe amplification" (MLPA) are readily available to the skilled person, for example "PCR Mutation Detection Protocols" by B. D. M. Theophilus and R. Rapley, 2nd Edition, 2011, Springer.

In another preferred variant, mutation analysis is performed using real-time quantitative PCR.

The mutation can thereafter be determined by comparing the property of the converted genomic DNA, for example the nucleotide sequence, molecular weight or hybridization strength, with a standard value. A suitable standard value is, for example, the corresponding property of the wild-typical DNA. Where appropriate, a corresponding conversion of the wild typical DNA according to step A) can also be taken into account, for example by suitable bioinformatic methods or by also passing the wild typical DNA through the method of the invention, for example as a reference sample.

The mutation can basically comprise a germline mutation or a somatic mutation or combinations thereof. In a preferred variant of the method, the mutation comprises a somatic mutation. While germline mutations can essentially be detected in all cells of an organism, somatic mutations can usually only be detected in cells of a certain tissue, for example in neoplastic cells of a tumor. It is a surprising advantage of the present invention that even such mutations with a low abundance in the organism can be detected with the help of the method of the present invention with high specificity and sensitivity.

In a preferred variant, the mutation analysis comprises at least a part or more parts of a gene contained in the genomic DNA. Alternatively or in addition, the mutation analysis may also comprise at least a part or more parts each of two or more genes contained in the genomic DNA.

In preferred variants, the mutation analysis includes at least one or more parts of a gene selected from the group consisting of BRAF, EGFR, KRAS, NRAS, BRCA1, BRCA2, AKT1, VGFR, IDH1, IDH2, CRLF2, TSC1, PDGFRA, NF1, GNAQ, GNA11, CTNNB1, ASXL1, BCOR, DNMT3A, ETV6, EZH2, SF3B1, SRSF2, STAG2, TET2, TP53, U2AF1, ZRSR2, HRAS, TERT (hTERT), SMO, FLT3, JAK2, ESR1, BCR, SMAD4, DNMT3A, AR, ERBB2 (HER2), MAP2K1 (MEK1), PIK3CA, PTEN, PALB2, DDR2, and any combinations thereof.

In other preferred variants, the mutation analysis is designed to determine a fusion, translocation and/or inversion of at least a part or more parts of a gene selected from the group consisting of NTRK1 (TRKA), RET, DEK-NUP214, MLL-MLLT3, CBFB-MYH11, RPN1-EVI1, RUNX1-RUNX1T1, PML-RARA, RBM15-MKL, KIT, ALK, ROS1, and any combinations thereof.

In other preferred variants, the mutation analysis is designed to determine amplification of at least one or more parts of a gene selected from the group of FGFR1, MET, ERBB2 (HER2), FGFR1, FGFR2, BCR-ABL1, RET, MEK, mTOR and VEGFR, and any combinations thereof.

In a preferred variant, the mutation analysis comprises at least one part or more parts of the BRAF gene. In particular, the mutation analysis can be designed to determine a mutation in at least part of a sequence which, in the wild type state, has at least 95% sequence identity with SEQ ID NO:71 and/or SEQ ID NO:72. In a particularly preferred variant, the mutation analysis includes the BRAF mutation c.1799T>A (V600E). For example, tumors that bear the point mutation V600E within the BRAF gene respond particularly well to treatment with Vemurafenib. The mutation analysis can also include any combination of these variants.

In another preferred variant, the mutation analysis includes at least one part or more parts of the EGFR gene. In particular, the mutation analysis can be designed to determine a mutation in at least part of a sequence which, in the wild type state, has at least 95% sequence identity with SEQ ID NO:64, SEQ ID NO:65, SEQ ID NO:66 or SEQ ID NO:67, as well as combinations thereof.

In another preferred variant, the mutation analysis includes at least one part or more parts of the KRAS gene. In particular, the mutation analysis can be designed to determine a mutation in at least part of a sequence which, in the wild type state, has at least 95% sequence identity with SEQ ID NO:68, SEQ ID NO:69 or SEQ ID NO:70, as well as combinations thereof.

In yet another preferred variant, the mutation analysis includes at least one part or more parts of the NRAS gene. In particular, the mutation analysis can be designed to determine a mutation in at least part of a sequence which, in the wild type state, has at least 95% sequence identity with SEQ ID NO:79 or SEQ ID NO:80, as well as combinations thereof.

The mutation analysis of ERBB2 (HER2) is preferably designed to determine a mutation in at least part of a sequence which, in the wild typical state, has at least 95% sequence identity with SEQ ID NO:77. The mutation analysis of MAP2K1 (MEK1) is preferably designed to determine a mutation in at least part of a sequence which, in the wild typical state, has at least 95% sequence identity with SEQ ID NO:78. The mutation analysis of PIK3CA is preferably designed to determine a mutation in at least part of a sequence which, in the wild typical state, has at least 95% sequence identity with SEQ ID NO:81 or SEQ ID NO:82, or combinations thereof. The mutation analysis of PTEN is preferably designed to determine a mutation in at least part of a sequence which, in the wild typical state, has at least 95% sequence identity with SEQ ID NO:83. The mutation analysis of DDR2 is preferably designed to determine a mutation in at least part of a sequence which, in the wild type state, has at least 95% sequence identity with SEQ ID NO:74, SEQ ID NO:75 or SEQ ID NO:76, or combinations thereof. The mutation analysis of AKT1 is preferably designed to determine a mutation in at least part of a sequence which, in the wild typical state, has at least 95% sequence identity with SEQ ID NO:73.

In a further variant, the mutation analysis is designed to determine viral DNA integrated into the genomic DNA, in particular at least a part or more parts of the DNA of one or more human papilloma viruses (HPV). The mutation analysis is preferably designed to determine at least a part or more parts of the DNA of one or more human papilloma viruses of the subgroups HPV 16, 18, 31, 33, 35, 39, 45, 51, 52, 56, 58, 59, 68, 73 and/or 82 in the genomic DNA.

Yet another variant of the mutation analysis is designed to determine amplifications and/or deletions that affect repetitive DNA sequences. In particular, it is possible to determine the amplification and deletion of short tandem repeats (STRs). In particular, this allows the determination of microsatellite instability (MSI). A microsatellite instability is indicative of a defective DNA repair system in the cell and therefore predictive for the response to DNA-damaging chemotherapy.

In a preferred variant, the genomic DNA comprises circulating cell-free DNA, DNA from exosomes and/or DNA from circulating cells from a body fluid, so-called "liquid biopsies". Liquid biopsies are currently a central area of oncological research. Instead of analyzing the suspicious tissue itself, for example a tumor tissue, this involves analyzing a sample of a body fluid, such as a blood sample. In this sample, different substances from the tumor can be investigated, since circulating cell-free genomic DNA, exosomal DNA or circulating cells are released from the tumor into the bloodstream. It is advantageous to use the method of the present invention for the analysis of liquid biopsies, in particular if the tumor or a metastasis cannot be biopsied or if a biopsy would be too dangerous for the patient in the advanced stage of the tumor.

It is possible to analyze mutations in circulating cell-free genomic DNA or in circulating cells with the method of the present invention. In particular, it is possible to detect few mutation-bearing DNA molecules against a background of circulating cell-free genomic DNA of healthy origin. For example, it is possible that the genomic DNA, in particular the converted genomic DNA, may comprise a greater proportion of DNA of healthy origin (wild typical DNA) and a smaller proportion of genomic DNA containing the at least one mutation. However, it was recognized in the course of the present invention that this can lead to sensitivity problems in determining a mutation when using a conventional method. For example, if a conventional mutation analysis was carried out on a patient with a malignant disease using a sample of circulating cell-free DNA and the detection of the mutation in the circulating cell-free DNA is negative, this may have two causes. Either the malignant disease in fact does not bear this mutation or there is insufficient or no DNA of the malignant disease in the patient's bloodstream or in the sample. In the latter case, the detection result is therefore false-negative.

It was therefore a further object of the invention to improve the sensitivity of the mutation analysis by reducing the number of false-negative results. This object is solved with a particularly preferred variant of the method that additionally includes C) performing a methylation analysis with the genomic DNA obtained from step A) to determine a methylation state of at least one CpG dinucleotide contained in the genomic DNA.

DNA methylation is an important process in the development and progression of malignant diseases, such as tumors. This methylation occurs mainly on the cytosines in the CpG dinucleotide sequence context. Many genes are hypermethylated in malignant diseases such as tumors, which means that these genes contain CpG dinucleotides, which are more often methylated than in the corresponding normal tissue from which the tumor originated. The methylation state of a CpG dinucleotide is therefore well suited for determining DNA of a malignant disease contained in genomic DNA. Thus, the methylation state of CpG dinucleotides can be used to differentiate the DNA of malignant disease from genomic DNA of healthy origin.

In this way, for the first time, a functional correlation between a mutation analysis and a methylation analysis can be established within a single analysis, for example in the form of normalization or internal standardization. For example, it is possible to determine the presence or absence of DNA from a malignant disease in genomic DNA using the methylation state of the CpG dinucleotide and correlate it with the presence or absence of the mutation. For example, if it can be demonstrated by the detection of an aberrantly methylated CpG dinucleotide that DNA of a malignant disease is contained in the genomic DNA and, at the same time, it can be shown that there is no mutation, then it has been established that the malignant disease does not carry the mutation and suitable treatment can be started. If the methylation analysis on the other hand shows that there is not any DNA of a malignant disease present, the mutation can thus not be detected. Consequently, it cannot be ruled out that the tumor may nevertheless carry the mutation. Supplementary analyses are necessary to find the most suitable treatment.

Due to this synergistic interaction of mutation analysis and methylation analysis, a significant improvement compared to conventional mutation analyses is achieved. For example, performing the mutation analysis and methylation analysis in one reaction according to the present invention leads to a significant improvement of the accuracy of measurement and thus to a significant improvement in the analytical performance of the method compared to conventional mutation analyses. The measurement accuracy of a molecular diagnostic test method can depend on many parameters. Quality features of a diagnostic test method are, for example, precision under intermediate conditions and robustness. The precision under intermediate conditions includes the variability that occurs when a test method is used at different points in time, with different test instruments and different reagent batches by different users, but in the same laboratory using the same sample and the same measurement method. The robustness of an analysis method indicates the level to which an analysis method remains unaffected by small, intentional changes in the process parameters and how reliable it is under normal operating conditions. By carrying out mutation analysis and methylation analysis in one reaction according to the invention, precision under intermediate conditions and robustness is significantly improved, since variances and changes within the measurement procedure are compensated and normalized or standardized by the internal correlation of both analyses. For example, false-negative diagnoses can be effectively avoided, which ultimately leads to an increase in sensitivity and a better and more efficient use of therapeutic options for the benefit of the patient. Of course, these advantages do not only apply to liquid biopsies, but also to other sources of genomic DNA. For example, the risk of false diagnosis due to a high proportion of healthy normal tissue in the analytical workflow, due to a low proportion of neoplastic cells in the malignant disease, or due to scattering of the cells in normal tissue is also drastically reduced.

In a further preferred variant, the methylation analysis includes determination of the methylation state of two or more CpG dinucleotides within a gene contained in the genomic DNA. Alternatively or in addition, the methylation analysis may also include at least one CpG dinucleotide in each of two or more genes contained in the genomic DNA. In this way, the invention solves the problem that CpG dinucleotides may sometimes be heterogeneously methylated in the DNA of a malignant disease, so that a particularly robust detection of DNA of the malignant disease is achieved. False-negative and false-positive diagnoses are thus avoided and the specificity and sensitivity of the diagnostic procedure is further improved.

The methylation analysis may comprise at least part of a gene selected from the group consisting of SHOX2, SEPT9, BRCA1, LIMK1, LIMK1, APC, VIM, RASSF2, RASSF1, GSTP1, FOXL2, CDKN2A (p16), RARB, and any combination thereof. The methylation state of CpG dinucleotides within these genes was found to be particularly reliable in detecting the presence or absence of DNA from a malignant disease within genomic DNA. In a preferred variant, the methylation analysis comprises at least part of SEPT9. In particular, the methylation analysis can be designed to determine the methylation state of one or more CpG dinucleotides of a sequence having in the wild type, unconverted state at least 95% sequence identity with SEQ ID NO:93. In a further preferred variant, the methylation analysis comprises at least part of SHOX2. In particular, the methylation analysis can be designed to determine the methylation state of one or more CpG dinucleotides of a sequence having in the wild type state at least 95% sequence identity with SEQ ID NO:6.

The methylation analysis may also include at least part of a gene described for this purpose in WO 2009/036922 A2 and/or US 2012/0101023 A1. The mutation analysis may also include at least part of a gene disclosed in US 2014/0303001 A1. The methylation analysis preferably comprises at least part of at least one gene from the group consisting of TWIST1, ONECUT2 and OTX1 and/or the mutation analysis at least part of at least one gene from the group consisting of FGFR3, TERT, KRAS, NRAS and PIK3CA. In this combination, for example, the method is designed to detect the presence and/or recurrence of bladder cancer according to the following second aspect of the invention. Favorably, the detection of bladder cancer is performed with genomic DNA comprising circulating cell-free DNA from urine and/or genomic DNA from cells of the urine sediment.

In a further embodiment, the methylation analysis comprises at least part of the gene SEPT9 and the mutation analysis at least part of the gene TP53. SEPT9 is aberrantly methylated in a large number of malignant diseases and regularly unmethylated in circulating cell-free DNA in plasma from healthy patients. The methylation analysis of this gene is therefore particularly suitable for the detection of a malignant disease in the blood. TP53 is recurrently mutated in various malignant diseases. The protein encoded by TP53 is relatively small with 393 amino acids. The 393 amino acids are encoded by 1179 bases within which the preferentially analyzed mutations are located. 86% of the mutations are found within amino acids 125 and 300. Accordingly, the mutation analysis of TP53 is preferably designed to determine a mutation in at least part of a sequence, which has in the unconverted wild type state at least 95% sequence identity with SEQ ID NO:94. In particular, with regard to the following second aspect of the invention, the mutation analysis of TP53 and the methylation analysis of SEPT9 are intended for the diagnosis of colorectal cancer, head and neck cancer, lung cancer, melanoma, ovarian cancer and esophageal cancer.

In a further variant, the mutation analysis comprises at least part of the TP53 gene as well as the determination of an insertion of viral DNA, in particular at least part or more parts of the DNA of one or more human papilloma viruses (HPV), in particular in combination with methylation analysis of at least part of SEPT9. For example, the most common causes of head and neck cancer are smoking and an insertion of the HPV virus. Head and neck tumors induced by an insertion of HPV usually do not carry a TP53 mutation. Therefore, in a preferred variant of the procedure, the mutation analysis of TP53 is carried out together with an analysis of the insertion of HPV, since the inventor has recognized that the majority of the tumors are detected when either one or the other mutation is present. SEPT9 is particularly often aberrantly methylated in head and neck tumors. Therefore, a combination of methylation analysis of SEPT9 with a mutation analysis of TP53 and/or a mutation analysis of an insertion of HPV is preferred, as this allows detecting these diseases with particularly high precision.

In preferred variants of the method, the mutation analysis in step B) is performed under conditions that allow a quantitative determination of said at least one mutation. Alternatively or additionally, the methylation analysis in step C) can also be performed under conditions that allow a quantitative determination of the methylation state of the at least one CpG dinucleotide.

For example, it is possible that the genomic DNA may comprise at least in a proportion DNA of a malignant disease, wherein the DNA of the malignant disease comprises said at least one, possibly aberrantly methylated, CpG dinucleotide and/or, if present, at least partially said at least one mutation. The proportion of the DNA of the malignant disease within the genomic DNA can then be determined by means of the mutation analysis in step B) and/or the methylation analysis in step C).

It is also possible to correlate the quantitative determination of the mutation in step B) with the quantitative determination of the methylation state in step C). In this way, for example, the proportion of mutation-bearing genomic DNA within the genomic DNA of the malignant disease can be determined. This is particularly advantageous because malignant diseases are often heterogeneous and not all cells of the disease carry the mutation. In this way, in addition to the diagnostic aspect, it is also possible to gain advantageous information regarding prognosis, prediction or monitoring of a malignant disease. This functional interaction of mutation analysis and methylation analysis is one of the unique features of the invention. In addition, the above-mentioned advantages in terms of robustness and precision of the process as well as the ability to analyze even very small amounts of genomic DNA also apply here.

In a further variant, the quantitative determination comprises a plurality of mutations distributed over one or more genes and/or the methylation state of a plurality of CpG dinucleotides in one or more genes. Subsequently, the obtained quantities can be averaged. For the relative quantification of the genomic DNA of the malignant disease within the genomic DNA, for example, the quantified methylation states of the individual CpG dinucleotides can be averaged to obtain a particularly robust value. It is also possible to use the CpG dinucleotide for quantification, for which the highest methylation value was determined, since this CpG dinucleotide is then particularly strongly methylated in the genomic DNA of the malignant disease and thus constitutes a reliable measure of its quantity. In this way, a particularly high robustness and precision of the method is achieved.

If the proportion of the genomic DNA of the malignant disease within the genomic DNA is to be determined by means of the mutation analysis in step B), the mutation analysis preferably comprises the determination of at least one recurrent mutation. It is also possible to determine the proportion of DNA of the malignant disease within the genomic DNA using at least one mutation of a recurrently mutated gene. Suitable and preferred recurrent mutations and recurrently mutated genes are listed in Example 11.

In preferred variants, the procedure comprises one or more of the following combinations: A mutation analysis comprising at least part of the BRAF gene and a methylation analysis comprising at least part of the SHOX2 gene; a mutation analysis comprising at least part of the BRCA1, BRCA2 and/or PALB2 gene and a methylation analysis comprising at least part of the BRCA1 gene; a mutation analysis comprising at least part of the IDH1, IDH2 and/or EGFR gene and a methylation analysis comprising at least part of the MGMT gene; a mutation analysis comprising at least part of the TP53 gene and a methylation analysis comprising at least part of the PITX2 gene; a mutation analysis comprising at least part of the AR, ESR1, BRCA1, BRCA2, PALB2 and/or ERBB2 (HER2) gene and a methylation analysis comprising at least part of the PITX2 gene; a mutation analysis comprising at least part of the FGFR3, TERT, PIK3CA, KRAS, TP53, NRAS and/or HRAS gene and a methylation analysis comprising at least part of the ONECUT2, OTX1, SHOX2, SEPT9 and/or TWIST1 gene; a mutation analysis comprising at least part of the TP53 gene and/or an insertion of viral DNA, in particular at least part or more parts of the DNA of one or more human papilloma viruses (HPV) and a methylation analysis comprising at least part of the SEPT9 gene. It is also possible to complement these combinations with methylation and/or mutation analyses of at least parts of further genes. For preferred genes and sequences, reference is made to the above description as well as the examples and the sequence listing.

The second aspect of the invention relates to a use of the method according to the first aspect for diagnosis, prognosis, prediction and/or monitoring of a malignant disease.

In particular, the malignant disease can include a carcinoma, a melanoma, a sarcoma, a glioma, a lymphoma and/or a leukaemia. The carcinoma can include, for example, an adenocarcinoma, a squamous cell carcinoma, a small cell carcinoma, a neuroendocrine carcinoma, a renal cell carcinoma, urothelial cancer, a hepatocellular carcinoma, an anal carcinoma, a bronchial carcinoma, an endometrial carcinoma, a cholangio-cellular carcinoma, a hepatocellular carcinoma, a testicular carcinoma, colorectal cancer, a head and neck carcinoma, an esophageal carcinoma, gastric cancer, breast cancer, a renal carcinoma, an ovarian carcinoma, a pancreatic carcinoma, a prostate carcinoma, a thyroid carcinoma and/or a cervical carcinoma.

A sarcoma can be, for example, an angiosarcoma, a chondrosarcoma, a Ewing sarcoma, a fibrosarcoma, a Kaposi sarcoma, a liposarcoma, a leiomyosarcoma, a malignant fibrous histiocytoma, a neurogenic sarcoma, an osteosarcoma or a rhabdomyosarcoma. For example, leukemia can be acute myeloid leukemia (AML), acute lymphatic leukemia (ALL), chronic lymphatic leukemia (CLL), or chronic myeloid leukemia (CML). Lymphoma can be Hodgkin's lymphoma or non-Hodgkin's lymphoma. A non-Hodgkin's lymphoma can be a B-cell lymphoma or a T-cell lymphoma.

In preferred uses, the method includes steps A), B) and C), because the synergistic effect of combined mutation analysis and methylation analysis of the present invention leads to a significant improvement in sensitivity and specificity of the diagnosis and to a more differentiated and reliable prognosis, prediction and monitoring, for example. In this regard, reference is also made to the following examples.

In a preferred use of the method for prognosis, the methylation analysis of a gene is used as a prognostic biomarker. To this end, the methylation analysis preferably comprises one or more CpG dinucleotides of the PITX2 gene. In particular, it can be designed to determine the methylation state of one or more CpG dinucleotides of a sequence having in the wild type, unconverted state at least 95% sequence identity with SEQ ID NO:90 and/or SEQ ID NO:91. Alternatively or in addition, the methylation analysis can also include one or more CpG dinucleotides of a gene selected from the group consisting of CDO1, PLAU, POU4F3, TFF1 and CXCL12, as well as combinations thereof. In this way, for example, the malignant disease can be detected and at the same time a conclusion can be made about the aggressiveness of the disease.

In a preferred use of the method for prediction and prognosis, the methylation analysis of a gene is used as a prognostic biomarker and mutation analysis of a gene is used as a predictive biomarker. For this purpose, the methylation analysis preferably comprises one or more CpG dinucleotides of the PITX2 gene, preferably one or more CpG dinucleotides of a sequence which in the wild type, unconverted state has at least 95% sequence identity with SEQ ID NO:90 and/or SEQ ID NO:91. Preferably, the mutation analysis comprises for this purpose one or more mutations of the genes BRAF, EGFR, KRAS, NRAS, BRCA1, BRCA2, AKT1, VGFR, IDH1, IDH2, CRLF2, TSC1, PDGFRA, NF1, GNAQ, GNA11, CTNNB1, ASXL1, BCOR, DNMT3A, ETV6, EZH2, SF3B1, SRSF2, STAG2, TET2, TP53, U2AF1, ZRSR2, HRAS, TERT (hTERT), SMO, FLT3, JAK2, ESR1, BCR, SMAD4, DNMT3A, AR, ERBB2 (HER2), MAP2K1 (MEK1), PIK3CA, PTEN, PALB2, DDR2, NTRK1 (TRKA), RET, DEK-NUP214, MLL-MLLT3, CBFB-MYH11, RPN1-EVI1, RUNX1-RUNX1T1, PML-RARA, RBM15-MKL, KIT, ALK, FGFR1, MET, ERBB2 (HER2), FGFR1, FGFR2, BCR-ABL1, RET, MEK, mTOR, VEGFR, and any combination of these genes. In a particularly preferred embodiment, the mutation analysis comprises for this purpose AR, ERBB2 (HER2), BRCA2, BRCA1 and/or ESR1.

In a variant, the response to therapy with inhibitors of the androgen receptor and/or the estrogen receptor, to therapy with PARP inhibitors and/or with therapeutic monoclonal antibodies directed against ERBB2 (HER2) can be predicted. In another variant, the effect of hormone receptor inhibitors such as anti-androgens and/or anti-estrogens is predicted. In a further variant, the prediction can concern substances such as enzalutamide, abiraterone, bicalutamide, flutamide, tamoxifen and cyproterone acetate. In yet another variant, the effect of PARP inhibitors such as Talazoparib (BMN-673), Olaparib (AZD-2281), Rucaparib (AG014699, PF-01367338), Veliparib (ABT-888), CEP 9722, MK 4827, BGB-290 and/or the effect of therapeutic monoclonal antibodies such as Trastuzumab is predicted. In yet another variant, the effect of AG-221, AGI-5198, AG-120, AG-881, Vemurafenib, Cetuximab, Crizotinib, Temozolomide, Erlotinib (Tarceva), Gefitinib (Iressa), Afatinib (Gilotrif), Dacomitinib, Neratinib, CO-1686 (Rociletinib) AZD9291 and/or HM61713 is predicted. Any combination of these variants is also possible.

Certain uses of the method for prediction can include, for example, a mutation analysis and methylation analysis of the same therapeutically relevant gene. This could be for instance a tumor suppressor gene such as a DNA repair gene and/or a proto-oncogene. For example, an aberrant methylation of the therapeutically relevant gene and/or a mutation, e. g. an inactivating mutation, can indicate the response of a patient with a malignant disease to a particular therapy, whereas the wild type and standard value, respectively, of the therapeutically relevant gene indicates that the patient will not respond to the therapy. The reverse case is also possible, wherein these constellations indicate that the patient will not respond to therapy.

In preferred variants of the method for prediction, the mutation analysis and/or methylation analysis comprises at least a part or more parts or one or more CpG dinucleotides of the BRCA1, BRCA2 and/or PALB2 gene. For particularly preferred sequences of these genes, reference is made to the sequences listed in Example 8.

However, it is also one of the unique advantages of the method of the invention that the interdependency between different therapeutically relevant genes can be determined, which influence each other with regard to the response of a patient to a therapy. For this purpose, as an alternative or in addition to the preceding variant, the mutation analysis can for instance comprise at least one part or more parts of a first therapeutically relevant gene and the methylation analysis can comprise one or more CpG dinucleotides of a second therapeutically relevant gene that is different from the first gene. In this way, the inventive discovery is taken into account that a methylation state of a first therapeutically relevant gene and a mutation of a second therapeutically relevant gene can have concomitant or opposite effects on a particular therapy. These interdependencies can be functionally brought into context and deciphered for the first time by the simultaneous mutation and methylation analysis of the present invention.

In preferred variants of method for prediction, the methylation analysis therefore comprises one or more CpG dinucleotides of the MGTM gene and the mutation analysis comprises at least one or more parts of the genes IDH1, IDH2 and/or EGFR. For particularly preferred sequences within these genes, reference is made to Example 9.

In a preferred use of the method, the prediction is made with regard to a patient's response to therapy with at least one substance selected from the group of alkylating chemotherapeutic agents, cytostatic drugs, therapeutic monoclonal antibodies and inhibitors, in particular tyrosine kinase inhibitors. Particularly preferred is the prediction with respect to an active ingredient selected from Temozolomide, Cetuximab, Bevacizumab, AG-221, AGI-5198, AG-120, AG-881, or combinations thereof.

In a preferred variant of the method for monitoring a patient's malignant disease, steps B) and C) are carried out under conditions that allow a quantitative determination of the at least one mutation and/or methylation state of the at least one CpG dinucleotide. Preferably, the use of the procedure for monitoring a malignant disease then includes the following steps: i) providing a first sample of genomic DNA from the patient from a first point in time and carrying out a method according to the first aspect, wherein the proportion of DNA of the malignant disease in the genomic DNA is determined by the mutation analysis in step B) and/or, if present, by the methylation analysis in step C); ii) providing a second sample of genomic DNA from the patient from a second point in time after the first point in time and repeating the method. The course of the malignant disease can then be monitored by a change of the proportion of DNA of the malignant disease in the genomic DNA in the second sample compared to the first sample. For example, the first point in time can be before the start of therapy and the second point in time after the start of therapy. An increase in the proportion of DNA of the malignant disease in the second sample can then indicate, for example, that the patient responds to the therapy. This is possible, for example, if the tumor dies and increasingly releases genomic DNA of the malignant disease into the blood during the dying process. It is also possible that an increase in the proportion of DNA of the malignant disease in the second sample may indicate that the patient is not responding to the therapy. This is possible, for example, if the tumor grows despite therapy and releases more genomic DNA from the malignant disease into the blood during the growth process. It is also possible that a slight decrease in the proportion of DNA of the malignant disease in the second sample may indicate that the patient is not responding to the therapy. This is possible, for example, if only part of the tumor responds to therapy and dies, so that still genomic DNA from the malignant disease enters the bloodstream.

In a variant of the method for monitoring, in step i) the first point in time is 2 to 12 days, preferably 4 to 10 days, particularly preferred 6 to 8 days after the start of a therapy, for example radiation therapy. In step ii) the second point in time can be 10 to 31 days, preferably 14 to 28 days, particularly preferred 18 to 24 days after the start of therapy. In another variant, the first or second point in time may also be 1 to 5 days, preferably 2 to 4 days after the beginning of a therapy or intervention, for example a surgery. The day on which the therapy was started or on which the intervention took place is considered to be day 0. Owing to the advantages already described above, a particularly specific detection of tumor DNA in the blood is achieved by the method according to the invention, so that, for example, it is possible to conclude with high reliability that a residual tumor remains and/or that occult metastases are present after a surgery.

It is possible to measure mutations in genomic DNA that do not originate from a malignant disease using the method of the present invention. For example, it is possible to detect mutations in fetal DNA circulating in the mother's blood. The detection of epileptic encephalopathies of the unborn child is possible, for example, by means of the analysis of fetal DNA in the mother's blood according to the invention. Preferably, mutations of the genes ALDH7A1, PNPO, SLC2A1, MECP2, FOXG1, ARX, CDKL5, STXBP1, SPTAN1, SCN1A, EIEE6, KCNQ2, EIEE7, ARHGEF9, EIEE8, PCDH19, PNKP, EIEE10, SCN2A, and/or EIEE11 are analyzed for this purpose. It is also possible to detect other genetic diseases of the unborn child in the mother's blood. Preferably, the use of the inventive method allows the diagnosis of achondroplasia by means of mutations in the FGFR3 gene; alpha-1-antitrypsin deficiency by means of mutations in the SERPINA1 gene; cystic fibrosis by means of mutations in the CFTR gene; Gaucher's disease using mutations in the GBA gene; Duchenne muscular dystrophy using mutations in the DMD gene; Mediterranean fever using mutations in the MEFV gene; Fragile X syndrome by mutations in the FMR1 gene; hereditary hemochromatosis by mutations in the HFE gene; Huntington's disease by mutations in the HTT gene; Marfan's syndrome by mutations in the FBN1 gene; Myotonic dystrophy by mutations in the genes CNPB and/or DMPK; factor V disease thrombophilia by mutations in the F5 gene; haemophilia by mutations in the genes F8 and/or F9; Noonan syndrome by mutations in the genes PTPN11, SOS1, RAF1 and/or KRAS; phenylketonuria by mutations in the PAH gene; X chromosomal severe combined immunodeficiency by mutations in the IL2RG gene; sickle cell anemia and thalassemia by mutations in the gene HBB; spinal muscular atrophy by mutations in the genes SMN1 and/or VAPB; neurofibromatosis type I and II by mutations in the genes NF1 and NF2; hypercholesterolemia based on mutations in the LDLR gene; osteogenesis imperfecta based on mutations in the genes COL1A1 and/or COL1A2; Tay-Sachs disease based on mutations in the HEXA gene; Velo-Cardio-Facial Syndrome by mutations in the genes COMT and/or TBX1; Wilson's disease by mutations in the gene ATP7B; trimethylaminuria by mutations in the gene FMO3. It is also possible to detect chromosomal mutations such as trisomy 21, deletion in chromosome 5 and/or microdeletions in chromosome 15 according to the invention for the diagnosis of Down's syndrome, cat cry syndrome and Angelman's syndrome. Any combination of these uses is also possible.

It is also possible to determine other benign and/or non-malignant diseases by the use of the method of the present invention. Preferred are KCNJ5 mutations in cortisol-producing adenomas of the adrenal glands and in hereditary hypertension; PRKACA and/or KCNJ5 mutations in cortisol-producing adenomas and hyperplasia of the adrenal glands; and CACNA1D mutations in aldosterone-producing adenomas and primary aldosteronism. Combinations of these uses are also possible.

The third aspect of the invention relates to a kit for carrying out the method according to the first aspect or for its use according to the second aspect. The kit comprises a) at least a first pair of oligonucleotides designed to hybridize to the genomic DNA obtained from step A) for amplifying at least a first part of the genomic DNA which is suspected of containing the at least one mutation. It is also possible that the first part additionally contains the at least one CpG dinucleotide whose methylation state is to be determined.

In a more preferred variant, the kit additionally comprises b) at least a second pair of oligonucleotides designed to hybridize to the genomic DNA obtained from step A) for amplifying at least a second part of the genomic DNA which contains the at least one CpG dinucleotide whose methylation state is to be analyzed.

It is possible that the first and/or second pair of oligonucleotides is designed in such a way that the part which is suspected to contain the at least one mutation, or the part which contains the at least one CpG dinucleotide, is at least partially reverse-complementary to one of the oligonucleotides of the first or second pair of oligonucleotides, respectively. In this way, a particularly specific amplification of the respective area to be analyzed is achieved. It is also possible, however, that the section in which the mutation is suspected or the section containing the CpG dinucleotide is located between the sequences which are reverse-complementary to the oligonucleotides.

The kit may also contain additional first and second oligonucleotide pairs to amplify further first and/or second parts of the converted genomic DNA suspected of containing a mutation or containing a CpG dinucleotide whose methylation state is to be analyzed.

Preferably, the first and second oligonucleotide pairs, as well as any additional oligonucleotide pairs, are designed for duplex or multiplex PCR. The GC content of oligonucleotides is preferably in the range of 20 to 70%, especially 30 to 60%. Primer length is preferably between 17 and 35 nucleotides, particularly preferred between 18 and 30 nucleotides. Preferably, one primer of a primer pair contains less than four cytosines and the other primer of the primer pair contains less than four guanines in the sequence which binds to the DNA. Preferably, one primer of a primer pair does not contain cytosine and the other primer of the primer pair does not contain guanine in the sequence which binds to the DNA.

Preferably, the binding site of an oligonucleotide of an oligonucleotide pair in the converted genomic DNA obtained from A) does not contain cytosines or methylcytosines. Preferably, the binding site of one oligonucleotide of an oligonucleotide pair or the reverse-complementary binding site of the other oligonucleotide of the oligonucleotide pair does not contain a CpG dinucleotide in the converted genomic DNA obtained from A).

In certain variants, the oligonucleotides of the first pair of oligonucleotides are designed in such a way that they are at least partially complementary to a sequence of converted DNA in which no conversion of cytosine takes place, in particular, which does not contain cytosine.

In a preferred variant, the first part contains at least a part of BRAF. In another preferred variant, the first part comprises at least a part of EGFR. In another preferred variant, the first part comprises at least a part of KRAS. In a further preferred variant, the first part comprises at least a part of BRCA1. In a further variant, the first part comprises at least a part of BRCA2. In yet another preferred variant, the first part comprises at least a part of PALB2. In another preferred variant, the first part comprises at least a part of IDH1. In another preferred variant, the first part comprises at least a part of IDH2. In another preferred variant, the first part comprises at least a part of TP53. Furthermore, any combination of these first parts is possible.

In a preferred variant, the second part comprises at least part of PITX2. In another preferred variant, the second part comprises at least part of CDO1, PLAU, POU4F3, TFF1 and/or CXCL12. In a further preferred variant, the second part comprises at least part of MGMT. In another preferred variant, the second part comprises at least part of SHOX2. In yet another preferred variant, the second part comprises at least part of SEPT9. Any combination of these second parts is also included.

Furthermore, any combination of one or more first and second parts is possible. In a preferred variant, for example, the first part comprises at least part of the BRAF gene and the second part comprises at least part of the SHOX2 gene. In a further preferred variant, the first part comprises at least part of the BRCA1, BRCA2 or PALB2 gene and the second part comprises at least part of the BRCA1 gene that can be different from the first part. In another preferred variant, the first part comprises at least part of the IDH1, IDH2 and/or EGFR gene and the second part comprises at least part of the MGMT gene. In another preferred variant, the first part comprises at least part of the TP53 gene and the second part comprises at least part of the PITX2 gene.

Further preferred parts and preferred sequences are given in the above descriptions, the examples as well as in the sequence listing.

The kit preferably includes instructions for performing the method according to the first aspect and/or for the use of the method according to the second aspect.

Detailed Description of Embodiments

In the following, the invention is described in more detail by way of examples and experimental results. These examples are intended as explanations and not as a limitation to specific details.

Example 1: Determination of a Point Mutation in Unconverted Genomic DNA (Reference Example)

Point mutations are mutations in which only a single nucleic base is changed. The reliable determination of point mutations therefore makes high demands on the specificity and sensitivity of a molecular diagnostic detection method.

The point mutation V600E within the BRAF gene was investigated as an example of a clinically highly relevant point mutation.

The genomic DNA to be analyzed can be obtained from different sources. In this example, fixed tissue was used. Three thin sections of 10 μm each of a formalin-fixed and paraffin-embedded malignant melanoma and a piece of tissue of the normal tissue (skin) adjacent to the melanoma were transferred into separate 2 ml reaction tubes. The genomic DNA was then extracted from the tissue sections. For this purpose, use of the QIAamp DNA FFPE Tissue Kit (Qiagen, Hilden, Germany) according to the manufacturer's instructions was suitable, for example.

The unconverted genomic DNA was then quantified using a NanoDrop ND-1000 spectrophotometer (Thermo Fisher Scientific, Waltham, MA, USA).

Afterwards, the locus of the BRAF gene in which the mutation was suspected was amplified from the unconverted genomic DNA. The locus was amplified using a PCR with the forward primer SEQ ID NO:1 and the reverse primer SEQ ID NO:2 to compare the resulting sequence with the unconverted wild typical sequence SEQ ID NO:3. For example, PCR reactions were performed in 20 µl volumes using the following conditions: 2 µl PCR reaction buffer with 20 mM MgCl$_2$ (10-fold concentrated, Roche, Penzberg, Germany), 2 U FastStart Taq DNA polymerase (Roche), 0.4 µM of each primer, 0.25 mM of each dNTP (dTTP, dATP, dGTP, dCTP). PCR was performed e. g. using a DNA Engine Tetrad Thermocycler (Biorad, USA). A suitable temperature profile included the following steps: 10 min at 95° C. followed by 40 cycles per 45 s at 54° C., 45 s at 72° C. and 15 s at 95° C. The resulting PCR product was then sequenced by Sanger sequencing, using the forward primer SEQ ID NO:1 as sequencing primer. Sanger sequencing of PCR products is a method that is easily accessible to the skilled person and is also offered as a service by many companies. The Sanger sequencings performed in this example were generated by Beckman Coulter Genomics, Hope End, Takeley, Essex CM22 6TA, United Kingdom.

FIG. 1A shows the result of the reference analysis of the unconverted genomic DNA from normal tissue. The normal tissue contains exclusively the wild type sequence CAC. Accordingly, there is no point mutation in this position. FIG. 1B shows the result of the reference analysis with the unconverted genomic DNA of the malignant tissue. In the sequence of the genomic DNA of the melanoma, the wild type sequence CAC and the V600E mutation with the base sequence CTC can be found.

Example 2: Determination of a Point Mutation in Genomic DNA

From the extracted DNA from example 1, a portion of each genomic DNA was converted according to the invention. The conversion can be carried out e.g. by contacting the genomic DNA with bisulfite. For example, the conversion was carried out with the innuCONVERT bisulfite all-in-one kit (Analytik Jena, Jena, Germany). For this purpose, 2 µg of the extracted DNA from each sample was converted according to the manufacturer's specifications. Afterwards, the amount of converted DNA was quantified using a NanoDrop ND-1000 spectrophotometer (Thermo Fisher Scientific, Waltham, MA, USA).

Normally, DNA is organized in the form of a double helix, which consists of two single strands that are complementary to each other. One strand is referred to as a positive or forward strand and the other strand is referred to as a negative or reverse strand. After the DNA has been converted, for example with bisulfite, the positive and negative strands are no longer reverse complementary to each other. For the description of the invention, the strand resulting from the bisulfite conversion of the positive strand is termed bisulfite-I strand. The strand resulting from the bisulfite conversion of the negative strand is termed the bisulfite-II strand.

In an exemplary embodiment of the invention, the mutation analysis can involve amplification of converted genomic DNA. In this example, the converted genomic DNA of the melanoma and normal tissue was amplified and quantified simultaneously using a real-time quantitative PCR (qPCR), as outlined below. Preferably, a PCR or qPCR is carried out as duplex or multiplex PCR in which, within the same reaction, one or more first parts of the converted genomic DNA are amplified which are suspected of containing a mutation and one or more second parts of the converted genomic DNA are amplified which contain a CpG dinucleotide whose methylation state is to be analyzed.

In order to quantify the total amount of converted genomic DNA, the locus of the BRAF gene was amplified in the qPCR with the primer sequences described in Example 1 above. The primers SEQ ID NO:1 and SEQ ID NO:2, for example, have been designed to hybridize to target sequence in the bisulfite-II strand in which no conversion of cytosine takes place. In the absence of a mutation, this sequence of the bisulfite-II strand corresponds to the sequence SEQ ID NO:4. By selecting these primers, both unconverted genomic DNA and converted genomic DNA can be amplified and quantified at the same time.

Sequence-specific detection and quantification of an amplicon can be achieved in different ways. For example, it can be accomplished using a probe. The detection of the BRAF amplicon was realized for example with a probe of SEQ ID NO:5, which contained a fluorophore/quencher system Atto-647N/BHQ-2.

The methylation analysis of the present invention can, for example, include a methylation-specific amplification reaction. For instance, oligonucleotides can be used for amplification, which in combination only lead to an amplification product if the CpG dinucleotide(s) to be investigated was/ were methylated. A suitable method is for example described in WO 02/072880 A2, which is hereby incorporated by reference in its entirety. Preferably, such methylation-specific amplification reactions are carried out as duplex or multiplex PCR in combination with the aforementioned amplification reaction of the mutation analysis.

For the methylation-specific amplification of the SHOX2 gene locus, whose unconverted wild type state corresponds to SEQ ID NO:6, the forward primer SEQ ID NO:7, the reverse primer SEQ ID NO:8 and a blocker oligonucleotide SEQ ID NO:9 were used, for example. As described in WO 02/072880 A2, the blocker oligonucleotide carries a phosphate instead of the OH-group at the 3'-end and thus cannot be extended by the polymerase, but prevents the hybridization of the forward primer to the converted genomic DNA if it was unmethylated. In this exemplary embodiment, a methylation-specific amplification of the bisulfite-I strand (SEQ ID NO:10) of the SHOX2 gene in the converted genomic DNA was thus achieved. The 6-FAM/BBQ-650 dual-labelled oligonucleotide of SEQ ID NO:11 was used for the sequence-specific detection of the amplicon.

It is possible to carry out a calibration to achieve a particularly high accuracy of the quantitative methylation analysis. For example, a calibration can be carried out using DNA which has the same sequence as the gene locus to be analyzed in the methylation analysis and which has been methylated in pre-defined proportions prior to conversion, for example to 50% or 100% methylation, hereinafter also referred to as standard DNA. In this example, the CpG methyltransferase M. SssI (New England Biolabs, Ipswich, MA, USA) was used in accordance with the manufacturer's instructions to completely methylate all CpG dinucleotides in human genomic DNA from leukocyte film (Roche Applied Science, Penzberg, Germany). In particular, all CpG dinucleotides within the sequence SEQ ID NO:6 were methylated. Afterwards, the DNA was converted using the innuCONVERT all-in-one bisulfite kit according to the manufacturer's specifications.

For the quantitative methylation analysis, 5 ng of the converted standard DNA or 50 ng of the converted DNA of the malignant melanoma or normal tissue were then used in the amplification reaction as described above.

In the present example, the real-time PCR quantification was performed in 20 µl PCR reactions in three independent measurements, with for instance the following suitable composition: 35 mM Tris-HCl, pH 8.4, 6 mM $MgCl_2$, 50 mM KCl, 4% glycerol, 0.25 mM of each dNTP (dTTP, dATP, dGTP, dCTP), 2 U FastStart Taq DNA polymerase (Roche Applied Science, Penzberg, Germany), 0.4 µM of each primer, 0.75 µM blocker oligonucleotide, 0.2 µM of each detection probe. For example, the qPCR was performed using an AB 7500 Fast Real-Time PCR system (Life Technologies Corporation, Carlsbad, CA, USA). A suitable temperature profile included for instance the following steps: 20 min at 95° C., followed by 45 cycles per 45 s at 56° C. and 15 s at 95° C.

The methylation state in the converted DNA of the malignant melanoma or normal tissue was calculated using the DeltaDelta-CT method and expressed as a percentage relative to the standard DNA, which was defined as 100%. The forward primer SEQ ID NO:7, reverse primer SEQ ID NO:8, blocker oligonucleotide SEQ ID NO:9 and the dual-labelled probe SEQ ID NO:11 used in this example are configured such that the methylation analysis encompasses a total of nine different CpG dinucleotides of the SHOX2 gene locus. The percentage methylation value calculated according to the DeltaDelta-CT method reflects the value that a corresponding mixture of DNA would have, which consists of the percentage parts of sequences that are correspondingly methylated or unmethylated at these nine CpG dinucleotides. For example, a measured methylation value of 66% corresponds to the behavior that a mixture of sequences would have in the qPCR, 66% of which are methylated in all nine analyzed CpG dinucleotides, whereas 34% of the sequences have no methylation in the nine CpG dinucleotides.

The methylation analysis using qPCR showed that the methylation state of the SHOX2 gene locus in the genomic DNA from the tissue section of the melanoma was 66%, whereas a methylation of less than 1% was measured in the adjacent skin tissue. Thus, it could be shown that the extracted genomic DNA of the melanoma contained a high proportion of DNA of the malignant disease.

Afterwards, the amplicon of the BRAF gene resulting from the qPCR was sequenced by Sanger sequencing as described in example 1. Instead of the primer SEQ ID NO:1, a modified sequencing primer SEQ ID NO:12 was used, which had a slightly shifted target sequence compared to SEQ ID NO:1. In this way, it can be avoided that unspecific amplification products from the qPCR are sequenced.

Simultaneously with the detection of the converted genomic DNA of the malignant disease, the presence of the BRAF V600E mutation in the genomic DNA of the melanoma could be confirmed unambiguously by Sanger sequencing of the qPCR product of the converted DNA (FIG. 1D), while the adjacent normal tissue showed no mutation (FIG. 1C).

Accordingly, the method of the present invention allows reliable determination of point mutations using converted genomic DNA. At the same time, the method of the present invention also allows simultaneous determination of the methylation state of at least one CpG dinucleotide, e. g. as a means of detecting the presence of DNA from a malignant disease in a sample of genomic DNA, and of the presence of a mutation. This simultaneous determination has the added benefit that false-negative results of a mutation analysis can be effectively avoided by correlating the mutation analysis and methylation analysis. Such false-negative results can occur in conventional analytical methods, for example through the unnoticed absence of DNA from a malignant disease in a sample of genomic DNA which is to be analyzed.

It is clear for the skilled person that this method can easily be adapted for the determination of further mutations and other malignant diseases. The mutations can be analyzed individually or in combination with each other simultaneously. Other methylation biomarkers can also be analyzed individually or in combination with each other. The combination of several DNA methylation biomarkers and/or mutations is limited only by the readout of different dyes when using real-time PCR based technology. An even higher multiplexability can be achieved with other methods. A preferred example of such a method is the multiplexed PCR amplification of several loci with subsequent analysis of the PCR amplicons using NGS.

Example 3: Determination of a Mutation in Circulating Cell-Free Genomic DNA

Mutation analysis in circulating cell-free genomic DNA from body fluids is particularly attractive, because it does not require surgical intervention on the patient. At the same time, this method is associated with an increased risk of producing false-negative results, as the amount of circulating DNA of a malignant disease can strongly depend on the stage of the disease. Especially in the early stages, only very small amounts of genomic DNA of a malignant disease circulate in the body, which is difficult to detect against a background of DNA of healthy origin.

This problem was recognized in the course of the present invention and solved with the help of the method according to the invention, as shown in the following example.

As an examplary body fluid, the blood plasma of four patients (A, B, C, D) with a malignant melanoma was analyzed. Two of the patients (C and D) were in an advanced stage of the disease and thus had a high tumor burden. Therefore, a high proportion of circulating cell-free tumor DNA in the blood was to be expected in these patients. The other two patients (A and B) suffered from a malignant melanoma in an earlier stage with very low tumor burden. As a consequence, a small amount of circulating cell-free tumor DNA had to be expected in these patients.

First, reference analyses were performed with the unconverted genomic DNA of the malignant tissue as described in example 1. One of the patients (D) in advanced stage and one patient in early stage (B) showed a V600E BRAF mutation after analysis of the tumor tissue, whereas the other two patients (A and C) did not have this mutation in the tumor tissue.

For performing the method of the present invention, genomic DNA from 3 ml blood plasma of each patient was first concentrated and then converted using the innuCONVERT bisulfite body fluid kit (Analytik Jena, Jena, Germany) according to the manufacturer's instructions. For example, the method used in this kit for concentrating circulating cell-free DNA from plasma is based on polymer-based enrichment. The conversion took place by contacting with bisulfite according to the kit protocol. The converted genomic DNA was finally eluted in 60 µl. These 60 µl with converted genomic DNA were used in six aliquots of 10 µl each in a quantitative real-time PCR, which was carried out in analogy to example 2.

By correlating the quantitative methylation analysis of the SHOX2 gene locus and the quantitative determination of the circulating cell-free DNA using the BRAF gene locus, the proportion of DNA of the malignant disease in the circulating DNA was determined.

Figure 2:
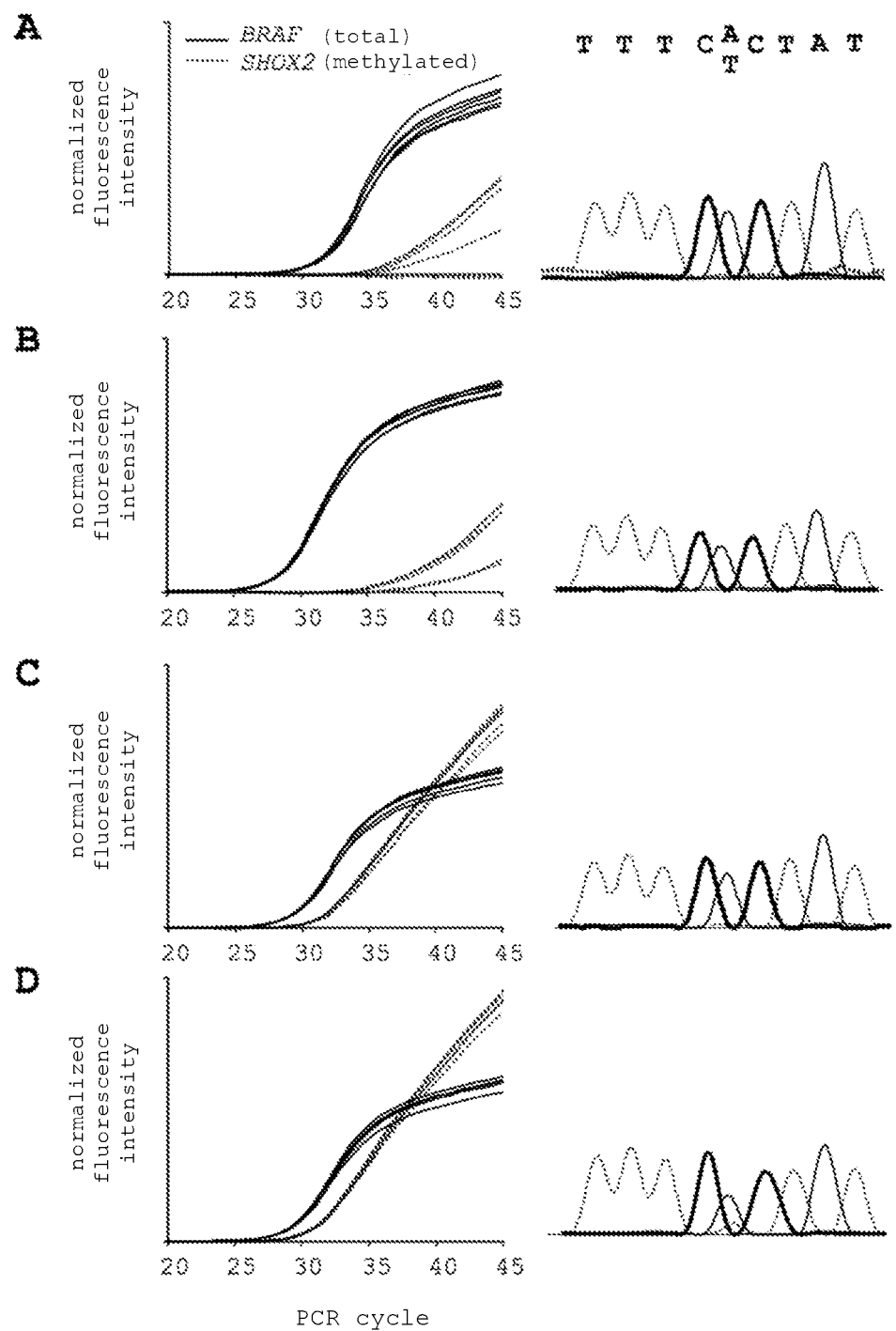
FIG. 2 shows the results of a combination of methylation analysis of SHOX2 and mutation analysis of BRAF in the plasma of melanoma patients. Left: Real-time PCR results for the total number of copies of BRAF DNA sequences (solid lines) and the number of copies of methylated SHOX2 DNA sequences (dashed lines). Right: Sequencing of the BRAF PCR amplicon generated by real-time PCR quantification. A: Patient with low tumor load and BRAF wild-type in the primary tumor. B: Patient with low tumor load and BRAF V600E mutation in the primary tumor. C: Patient with high tumor load and BRAF wild-type in the primary tumor. D: Patient with high tumor load and BRAF V600E mutation in the primary tumor.

FIG. 2 shows the results of the combined methylation analysis of SHOX2 and mutation analysis of BRAF in the plasma of the melanoma patients. The diagrams in the left column show the results of quantitative real-time PCR for the proportion of BRAF DNA copies independent of methylation and mutation state as a measure of the total amount of genomic DNA, and for the number of methylated SHOX2 DNA copies as a measure of the proportion of DNA of the malignant disease in the genomic DNA. The right column shows the results of the sequencing of the BRAF amplicon generated by real-time PCR (A: Patient with low tumor burden and with BRAF wild type in primary tumor according to the reference analysis; B: Patient with low tumor burden and BRAF V600E mutation in primary tumor; C: Patient with high tumor burden and BRAF wild type in primary tumor; D: Patient with high tumor burden and BRAF V600E mutation primary tumor).

Based on the inventive correlation of the methylation analysis of the SHOX2 gene locus with the total amount of circulating cell-free genomic DNA measured by the BRAF gene locus, it was found that in case of patient A 1.7% DNA of the malignant disease and in case of patient B 0.26% DNA of the malignant disease was present in the plasma. This corresponds to a relatively early stage of tumor development, where there is generally only a small amount of tumor DNA in the blood plasma.

In the subsequent Sanger sequencing of the generated BRAF amplicons, only wild DNA could be detected with patients A and B, although patient B carried the mutation (FIG. 2, right column). If considered separately, the mutation analysis of the circulating cell-free genomic DNA would thus lead to a false-negative result for patient B. By means of the combined mutation analysis and methylation analysis of the present invention, however, this result could be attributed to the insufficient amount of DNA of the malignant disease in the plasma and could therefore be reliably identified as false-negative. By contrast, a conventional mutation analysis would have led to a false-negative diagnosis.

The situation is different with patients C and D. In both cases, the methylation analysis showed that a high amount of circulating cell-free DNA of the malignant disease was present in the blood (FIG. 2, left column: patient C: 26%; patient D: 41%). Although the mutation analysis of patient C only indicated the wild typical sequence, the combination of methylation analysis and mutation analysis of the present invention ruled out the possibility of a false-negative results. The malignant disease of patient C therefore does not carry the BRAF V600E mutation. This correctly negative diagnosis could not have been differentiated from a false-negative result with a conventional method using mutation analysis alone.

In this way, the method of the present invention increases the sensitivity of molecular diagnostic mutation analyses, in particular such based of circulating cell-free genomic DNA, exosomal DNA or circulating cells, by reducing the number of false-negative results.

Example 4: Determination of a Mutation that Leads to the Formation of a CpG the Epidermal Growth Factor Receptor (EGFR) is a Tyrosine Kinase that is normally activated by the binding of a ligand. Mutations lead to constitutive activation and thus to increased cell proliferation. EGFR tyrosine kinase inhibitors (TKI) compete with ATP for binding to the ligand binding pocket of the receptor, thereby inhibiting both tyrosine kinase activity and the EGFR signaling pathway. In patients with activating mutations in EGFR, these TKI are considered frontline therapy and can improve progression-free survival of patients and their response rates to therapy. EGFR mutations are therefore strong predictive markers for the response to EGFR tyrosine kinase inhibitors (TKI), such as the first-generation TKIs Erlotinib (Tarceva) and Gefitinib (Iressa) and second-generation TKIs such as Afatinib (Gilotrif), Dacomitinib and Neratinib. Third-generation TKIs such as CO-1686 (Rociletinib), AZD9291 and HM61713 are additionally designed to inhibit the mutated EGFR protein more effectively than the EGFR wild type. For these reasons, determining the mutation status of EGFR is particularly important for a personalized, targeted therapy.

In lung tumors, EGFR mutations are particularly common in adenocarcinomas, women and non-smokers. They are found in 9% in exon 18, in 51% in exon 19, in 18% in exon 20 and in 22% in exon 21 of the EGFR gene. Approximately 5% of EGFR mutations lead to secondary therapy resistance to EGFR-TKI. The Mutation c.2369C>T (T790M) is the most common mechanism for a EGFR-TKI therapy resistance.

In this example, the c.2573T>G (L858R) mutation of EGFR was investigated. It is located in exon 21 within the kinase domain of the EGFR gene and occurs in about 43% of lung tumors in which EGFR is mutated.

Three thin sections of 10 μm each of a formalin-fixed and paraffin-embedded lung tumor and a piece of normal lung tissue adjacent to the tumor were each transferred into a 2 ml reaction tube. Genomic DNA was extracted from the tissue sections using the QIAamp DNA FFPE Tissue Kit (Qiagen, Hilden) according to the kit instructions. Of each extracted DNA, 2 μg were converted per sample using the innuCONVERT bisulfite all-in-one kit (Analytik Jena, Jena, Germany).

The unconverted part of the extracted DNA was used for reference analysis. To this end, the genomic unconverted DNA was amplified using two primers (primer sequences SEQ ID NO:13 and SEQ ID NO:14), which amplify the genomic locus in exon 21 of the EGFR gene in which the mutation was suspected. The resulting amplicon was then sequenced by Sanger sequencing and compared with the unconverted wild typical sequence SEQ ID NO:15, using the forward primer SEQ ID NO:13 as the sequencing primer. PCR amplification and Sanger sequencing was performed as described in example 1.

Figure 3:
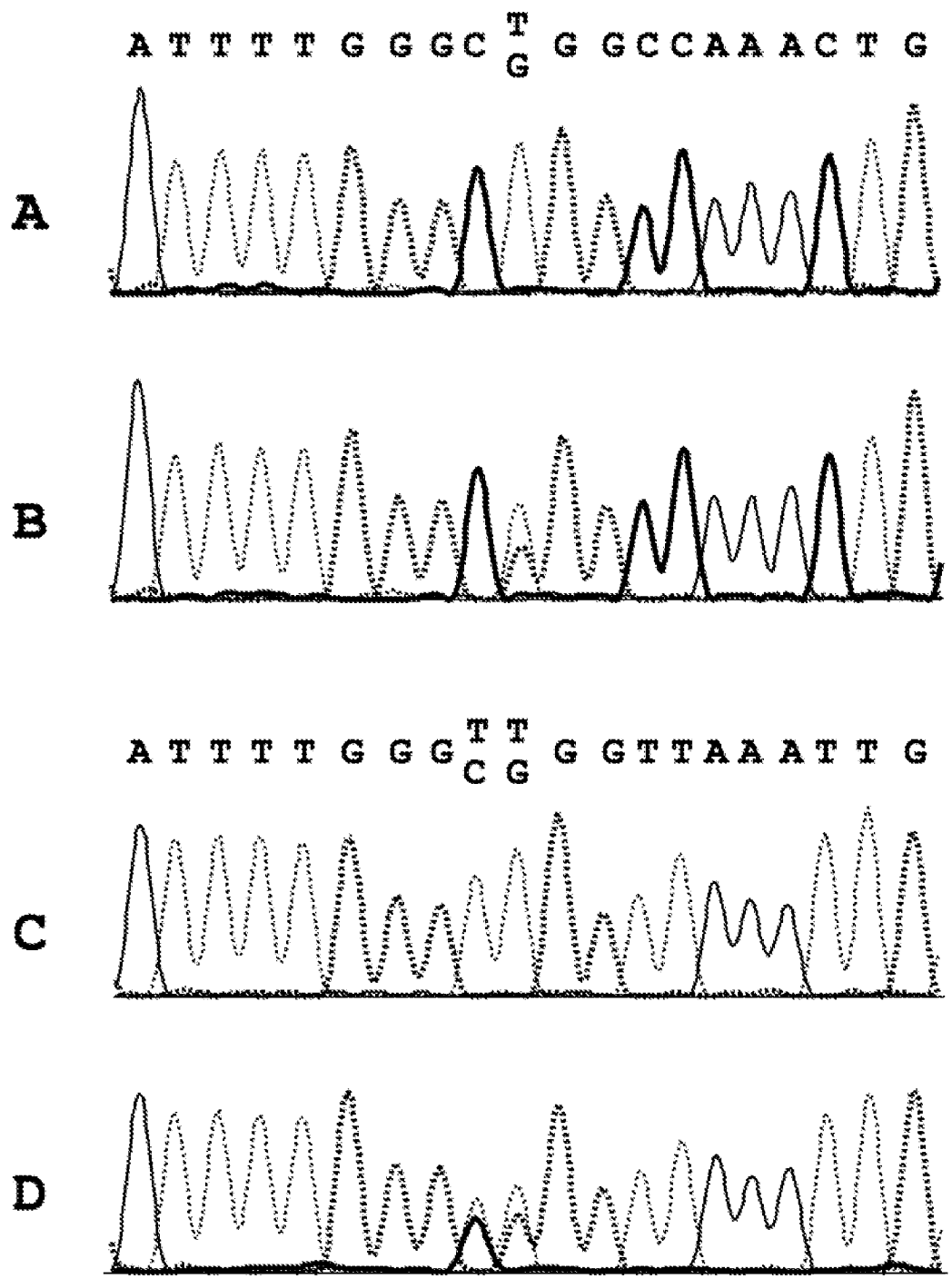
FIG. 3 shows the results of the sequencing of the EGFR locus (exon 21) with L858R mutation. A: Reference analysis of unconverted genomic DNA from healthy tissue adjacent to the tumor. B: Reference analysis of unconverted genomic DNA of tumor tissue. C: Analysis of converted genomic DNA of healthy tissue according to the present invention. D: Analysis of converted genomic DNA of tumor tissue according to the present invention.

The result of the reference analysis of the EGFR locus in exon 21 is summarized in FIGS. 3A and 3B. FIG. 3A shows the recorded sequence of the healthy tissue adjacent to the tumor. FIG. 3B shows the recorded sequence of the tumor tissue. It has been found that there is no mutation in the genomic DNA of the adjacent normal tissue. In the sequence of the genomic DNA from the tumor, on the other hand, the L858R mutation (CGG) can be found in addition to the wild typical sequence (CTG).

For the mutation analysis according to the present invention, the converted genomic DNA was amplified with primers of the sequences SEQ ID NO:16 and SEQ ID NO:17 to determine a deviation of the bisulfite-I strand with sequence SEQ ID NO:18 from the wild typical sequence. The bisulfite-I strand with sequence SEQ ID NO:18 corresponds to the sequence resulting from conversion of the positive strand of the wild typical genomic sequence SEQ ID NO:15. The resulting PCR products were then sequenced using the forward primer SEQ ID NO:16 as sequencing primer. PCR amplification and Sanger sequencing were performed as described in example 1.

The result of the method of the invention is shown in FIGS. 3C and 3D. FIG. 3C shows the determined sequence of the healthy tissue, FIG. 3D shows the determined sequence of the tumor tissue. It was found that the CpG dinucleotide resulting from the point mutation is methylated in the tumor tissue. Because of its methylation, the cytosine in this CpG dinucleotide is not converted by bisulfite treatment. In this way, the sequence of converted wild type DNA (FIG. 3C) differs advantageously in an additional base from the sequence of the converted tumor DNA (FIG. 3D). In contrast, since only one base is different in the genomic unconverted DNA of the tumor, this type of mutation can be detected much better with the invention-based method than with the conventional mutation analysis. This leads to a surprising improvement in the sensitivity and specificity of the mutation analysis according to the invention, even with a small proportion of DNA of the malignant disease in the sample.

Example 5: Determination of a Deletion in Genomic DNA

Deletions that lead to a loss of amino acids in the protein are other frequently found mutations in the EGFR gene. They often take place in exon 19, which encodes part of the kinase domain. These mutations are also predictive for the response to therapy with TKIs directed against EGFR. Approximately 48% of EGFR-mutated lung tumors have a deletion in exon 19.

The aim of this study was to show that deletions in converted genomic DNA can be reliably detected. For this purpose, three thin sections of 10 μm each of a formalin-fixed and paraffin-embedded lung tumor and a piece of normal lung tissue adjacent to the tumor were each transferred into a 2 ml reaction vessel. Using the QIAamp DNA FFPE Tissue Kit (Qiagen, Hilden), genomic DNA was extracted from the tissue sections according to the kit instructions. Of the extracted DNA, 2 μg DNA of each sample was converted using the innuCONVERT bisulfite all-in-one kit (Analytik Jena, Jena, Germany).

Part of the extracted DNA was not converted and used for reference analysis. For this purpose, the primers SEQ ID NO:19 and SEQ ID NO:20 were used, which are designed to amplify the mutation-bearing genomic locus in exon 21 of the EGFR gene, for comparing the resulting sequence with the unconverted wild typical sequence SEQ ID NO:21. The resulting amplicon was sequenced in a Sanger sequencing using the reverse primer SEQ ID NO:20 as the sequencing primer. PCR amplification and Sanger sequencing were performed as described in example 1.

Figure 4:
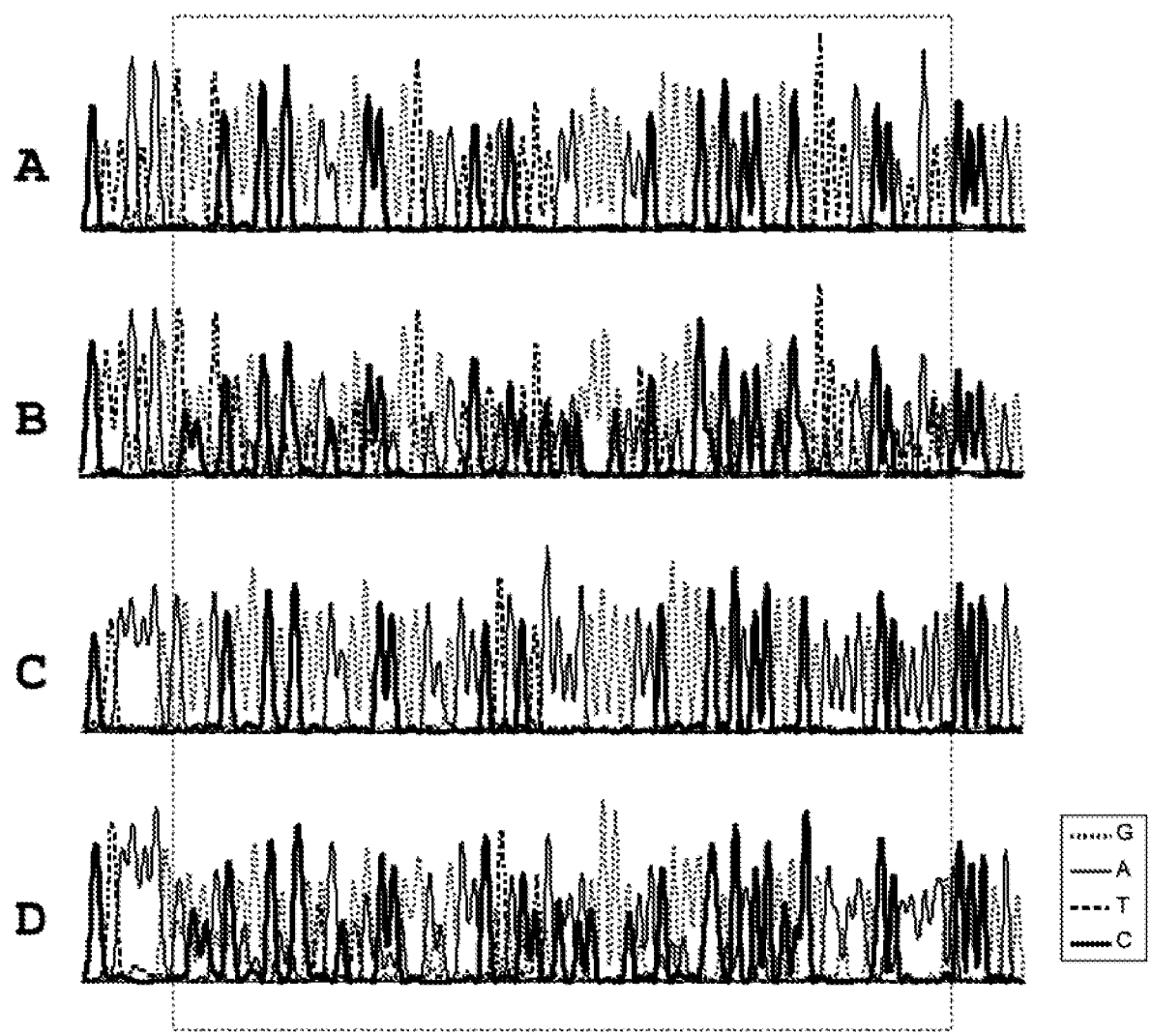
FIG. 4 shows the results of the sequencing of the EGFR gene locus (exon 19) with a deletion. A: Reference analysis of unconverted genomic DNA from healthy tissue adjacent to the tumor. B: Reference analysis of unconverted genomic DNA of tumor tissue. C: Analysis of converted genomic DNA of healthy tissue according to the present invention. D: Analysis of converted genomic DNA of tumor tissue according to the present invention.

The result of the reference analysis is shown in FIG. 4. FIG. 4A shows that there is no mutation in the unconverted genomic DNA of the adjacent normal tissue. In the sequence of unconverted DNA from the tumor, on the other hand, there is an overlap between the wild typical sequence and a mutated sequence in which 15 bases are deleted (FIG. 4B). This deletion leads to an overlapping of the bases, which follow the deletion, with the wild typical sequence.

For the method according to the invention, the converted genomic DNA was amplified with the primers SEQ ID NO:22 and SEQ ID NO:23 to determine a deviation of the bisulfite-I strand from the wild typical sequence with the sequence SEQ ID NO:24. The SEQ ID NO:24 corresponds to the sequence resulting from a conversion of the positive strand of the wild typical genomic sequence SEQ ID NO:21. The resulting amplicons were then sequenced using the reverse primer SEQ ID NO:23. PCR amplification and Sanger sequencing was performed as described in example 1.

The results of the sequencing are shown in FIG. 4C for the converted genomic DNA of the normal tissue and in FIG. 4D for the converted genomic DNA of the tumor. It can be seen that the deletion in one allele of exon 19 leads to a similar overlay pattern as in the sequencing of the unconverted genomic DNA of the tumor. Consequently, deletions can also be reliably determined by means of the method according to the invention.

In order to further confirm determination of the deletion in converted genomic DNA, the PCR product of the mutation-containing converted DNA was ligated into a plasmid. The plasmids were transformed into *E. coli* and isolated on an agar plate. Individual cells were grown overnight at 37° C. to form clonal colonies. Cells of individual *E. coli* clones were transferred into PCR reactions and then sequenced. The cloning of the PCR product was carried out using the TOPO-TA cloning kit (Life Technologies, Carlsbad, CA, USA) according to the manufacturer's instructions. PCR amplification was performed as described in example 1. The primers SEQ ID NO:22 and SEQ ID NO:23 were used for this purpose. Sequencing was performed as described in example 1. SEQ ID NO:23 was used as sequencing primer.

Figure 5:
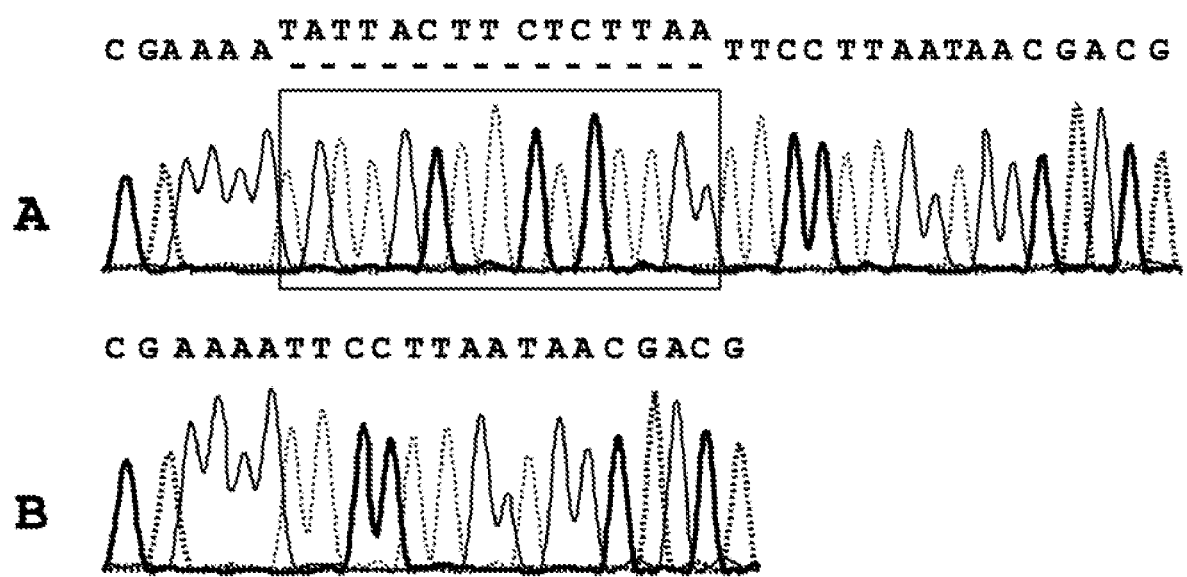
FIG. 5 shows the result of clone sequencing of both alleles of PCR products from FIG. 4D. A: Wild type allele of the converted genomic DNA of the mutation-carrying tumor. B: Mutated allele of the converted genomic DNA of the mutation-carrying tumor with a deletion of 15 bases.

FIG. 5A shows that part of the converted genomic DNA in the sample containing the tumor DNA is wild typical, whereas the allele shown in FIG. 5B clearly has a deletion of 15 bases.

Example 6: Determination of a Mutation with Cytosine-Thymine Transition

In the prevailing teaching, it has been assumed so far that mutations in converted genomic DNA are very difficult or even impossible to detect. This widespread opinion was also based on the fact that unmethylated cytosine is converted for example to uracil and that uracil does not differ from thymine in its base pairing properties. In the scientific community, it was therefore considered an unsolvable problem to differentiate between a thymine introduced by C to T mutation on the one hand and a thymine introduced by the conversion of cytosine on the other hand.

This false idea was overcome in the course of the present invention. By innovative understanding, it has been realized for the first time that this problem can be solved if, instead of or in addition to the converted positive strand of the genomic sample, the converted negative strand of the genomic DNA is also included in the mutation analysis according to the invention. A transition from C to T in the positive strand corresponds to a G to A transition in the negative strand. The aim of the present example was therefore to show by using the mutation c.437C>T (A146V, COSM1360827) in exon 4 of the KRAS locus that the G to A transition is well detectable in the negative strand after a conversion of the genomic DNA and that reliable determination of a point mutation, which is solely based on a C to T transition, is thus possible.

For this purpose, three thin sections of 10 μm each of a formalin-fixed and paraffin-embedded adenocarcinoma of the colon and a piece of normal intestinal tissue adjacent to the tumor were each transferred into a 2 ml reaction tube. Using the QIAamp DNA FFPE Tissue Kit (Qiagen, Hilden, Germany), genomic DNA was extracted from the tissue sections according to the kit instructions. Of the extracted DNA, 2 μg DNA per sample was converted using the innuCONVERT bisulfite all-in-one kit (Analytik Jena, Jena, Germany).

Another part of each extracted DNA was not converted and used for the reference analysis. To this end, the potentially mutation-carrying genomic locus in exon 4 of the KRAS gene was amplified in a PCR using the primers SEQ ID NO:25 and SEQ ID NO:26 in order to determine deviations from the unconverted wild typical DNA sequence SEQ ID NO:27. The resulting PCR product was then sequenced in a Sanger sequencing using the forward primer SEQ ID NO:25 as the sequencing primer. PCR amplification and Sanger sequencing was performed as described in example 1.

Figure 6:
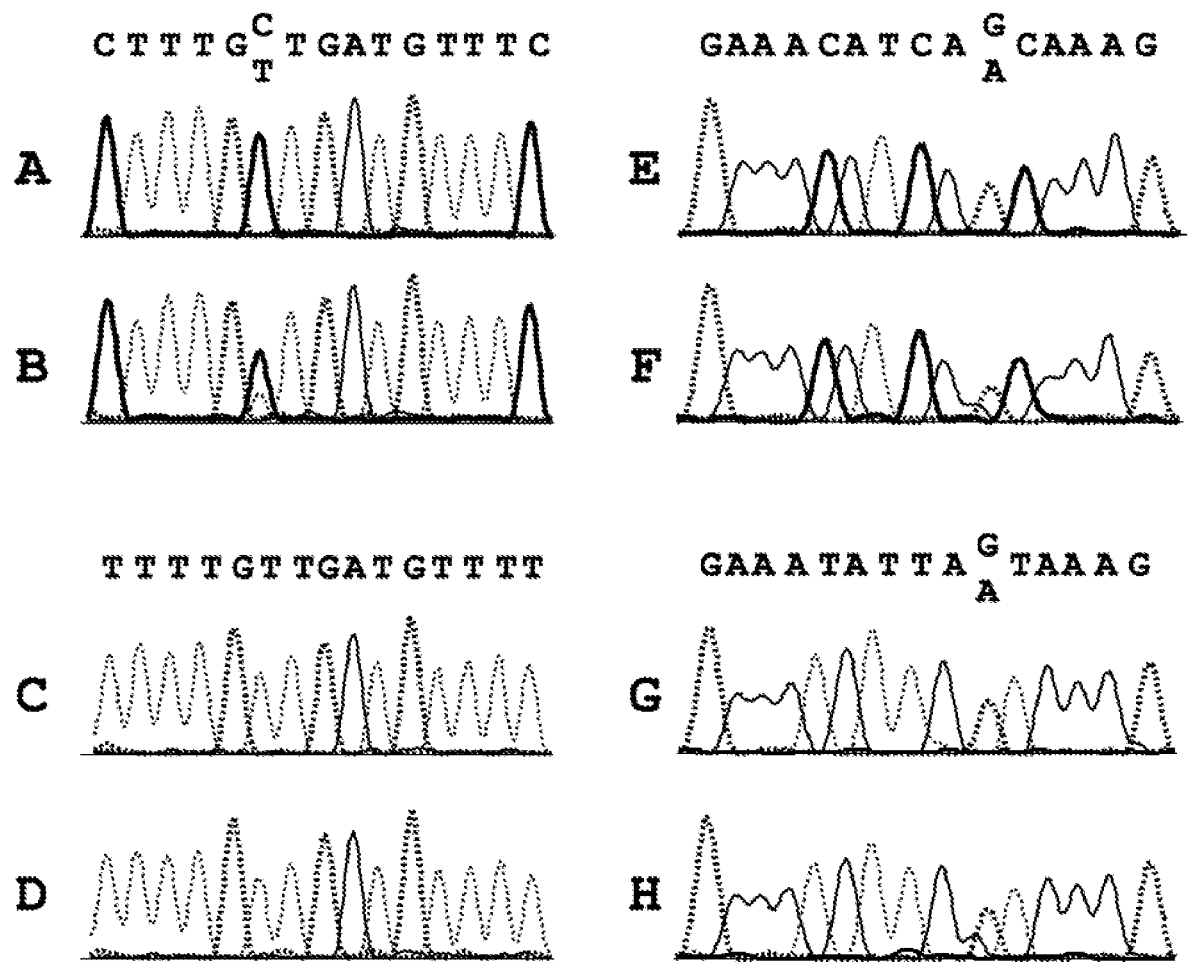
FIG. 6 shows the results of the KRAS gene locus sequencing (exon 4). A: Reference analysis of unconverted genomic DNA from healthy tissue adjacent to the tumor. Sequencing of the forward strand. B: Reference analysis of unconverted genomic DNA of tumor tissue. Sequencing of the forward strand. C: Analysis of converted genomic DNA of healthy tissue according to the present invention. Forward sequencing of the bisulfite-I strand. D: Analysis of converted genomic DNA of tumor tissue according to the present invention. Forward sequencing of the bisulfite-I strand. E: Same as A, but reverse strand sequencing. F: Same as B, but reverse strand sequencing. G: Analysis of converted genomic DNA from healthy tissue according to the present invention. Reverse sequencing of the bisulfite-II strand. H: Analysis of converted genomic DNA of tumor tissue according to the present invention. Reverse sequencing of the bisulfite-II strand.

FIGS. 6A and 6B show the result of the reference analysis. FIG. 6A shows the sequence of the unconverted genomic DNA from the healthy tissue adjacent to the tumor after sequencing the forward strand. FIG. 6B shows the sequence of the unconverted genomic DNA of the tumor tissue after sequencing the forward strand. Accordingly, there is no mutation in the unconverted genomic DNA of the adjacent normal tissue (6A). In the sequence of the genomic DNA from the tumor, on the contrary, a mutant sequence with a C to T transition occurs in addition to the wild typical sequence (6B).

For performing the method of the present invention, a PCR amplification of the corresponding gene locus in exon 4 of the KRAS gene was carried out using the primers with the sequences SEQ ID NO:29 and SEQ ID NO:30 in order to determine a deviation of the amplicon from the sequence SEQ ID NO:28. The sequence SEQ ID NO:28 corresponds to the converted wild typical sequence of the positive strand with the sequence SEQ ID NO:27. The PCR amplification was carried out as described in example 1. The result of the subsequent Sanger sequencing, which was performed according to example 1 using the forward primer SEQ ID NO:29, is shown in FIGS. 6C and 6D. FIG. 6C shows the sequence of the converted genomic DNA of the healthy tissue after forward sequencing of the bisulfite-I strand, FIG. 6D shows the sequence of the converted genomic DNA of the tumor tissue after forward sequencing of the bisulfite-I strand. The result shows that the C to T transition is no longer detectable due to the chemical conversion of C to U in the bisulfite-I strand. This is due to the fact that a U in the converted genomic DNA is replaced by a T during PCR amplification, so that the originally mutated sequence is no more distinguishable from the wild typical sequence.

Next, the mutation analysis of the corresponding gene locus in exon 4 of the KRAS gene was performed using the bisulfite-II strand to determine a deviation from the converted wild typical sequence SEQ ID NO:31. The primers SEQ ID NO:32 and SEQ ID NO:33 were used for PCR amplification of the bisulfite-II strand. The sequencing of the PCR product was performed using the reverse primer SEQ ID NO:32. The results are shown in FIG. 6E-H.

FIGS. 6E and 6F show as a reference the wild type variant and the mutation as obtained by sequencing of the unconverted genomic DNA using the reverse primer SEQ ID NO:26. FIGS. 6G and 6H show the sequences determined from the converted genomic DNA of the healthy tissue (6G) and the tumor tissue (6H) as obtained by reverse sequencing of the bisulfite-II strand described above. Unlike the healthy tissue, it can be clearly seen that in the tumor tissue the mutant sequence with the G to A transition occurs in addition to the wild typical sequence. This G to A transition corresponds to the C to T transition on the forward strand.

Accordingly, the method of the present invention generally allows a reliable determination of mutations which comprise or consist of a C to T transition, contrary to erroneous belief in the scientific community.

In certain variants of the method of the present invention, the mutation analysis therefore involves determining the mutation using the converted negative strand of the genomic DNA.

Example 7: Multiplexed Determination of Mutations in Genomic DNA from Body Fluids and Tissues In a preferred embodiment of the invention, a combined mutation and methylation analysis is performed comprising several genes from different areas of the genome, hereinafter also referred to as genome-wide mutation and methylation analysis.

Preferably, the genome-wide mutation and methylation analysis is performed using circulating cell-free genomic DNA from body fluids. Blood plasma, blood serum, urine, ascites and pleural effusions are particularly suitable. The conversion of genomic DNA from body fluids can for instance be accomplished using the innuCONVERT bisulfite body fluids kit (Analytik Jena, Jena, Germany) according to the kit instructions.

Subsequently, a combined mutation analysis and methylation analysis using an appropriate genome-wide sequencing method is to be carried out. In preferred variants, a high-throughput sequencing method such as Next Generation Sequencing is used. More preferably, the Whole Genome Shotgun Bisulfite Sequencing (WGSBS) method is used. In this way, a large number of mutations and CpG methylation states, respectively, can be determined in parallel. If the determination is performed on a quantitative basis, the determined quantities can further be correlated to the corresponding wild typical sequences or methylation states within the, if required converted, genomic DNA. In this way, for example, the relative proportion of mutation-bearing DNA and/or DNA of a malignant disease (based on the methylation state) within the genomic DNA can be determined. In this way, it is also possible to determine the proportion of DNA of a malignant disease that carries a mutation. This can be particularly advantageous given the fact that malignant diseases such as tumors often have a heterogeneous genetic composition or, for example, the relative proportion of mutation-bearing DNA in the genomic DNA of a malignant disease can change e. g. through therapy so that conclusions can be drawn about the therapy and/or disease progression.

A further embodiment provides that the mutation analysis and/or methylation analysis of the converted genomic DNA from body fluids is not carried out directly using a genome-wide sequencing method as described above. In this case, the parts of the converted genomic DNA which are to be investigated are amplified first. In a preferred application, these parts are amplified using PCR. The primer pairs are designed for generating amplicons from the converted genomic DNA each comprising one or more mutation sites or CpG dinucleotides to be analyzed. Preferably, the primer pairs are also designed to be compatible with multiplexed PCR using a variety of primer pairs for simultaneous amplification of a variety of parts of converted genomic DNA to be investigated. Afterwards, the large number of PCR amplicons is analyzed, for example by means of Next Generation Sequencing.

In a further preferred embodiment, the analysis is carried out by multiplexed, ligation-dependent probe amplification (MLPA). For this purpose, the probes used for MLPA are designed in such a way that they bind to the mutation sites or methylation sites which are to be analyzed and, for example, are ligated if a mutation or methylation of a CpG dinucleotide is present. Subsequently, the ligated probes can be amplified by PCR and optionally sequenced.

In another preferred embodiment, DNA from fresh or fixed tissues or circulating tumor cells is analyzed instead of circulating cell-free DNA.

Example 8: Prediction Using Combined Mutation and Methylation Analysis within a Gene In the course of the present invention, it was discovered that a response of a patient with a malignant disease to therapy such as chemotherapy may depend on whether, for example, certain DNA repair enzymes in the tissue of the malignant disease are active or inactive. Inactivation can for instance be due to the methylation state or an inactivating mutation of the corresponding gene encoding the repair enzyme in the genomic DNA of the malignant disease. With a view to more targeted therapy, it can therefore be advantageous to examine the same gene both in terms of its methylation state as well as the presence of a mutation.

The invention provides for such a procedure, for example, in relation to the treatment with PARP inhibitors. PARP inhibitors are a group of pharmacological substances that inhibit the enzyme poly-ADP-ribose polymerase (PARP). This enzyme is important for the repair of single-strand breaks in DNA. If these single-strand breaks are not repaired efficiently, they can lead to double-strand breaks, which in turn can lead to cell death if they are not repaired. This is desirable for example in chemotherapy and/or radiation therapy of tumors. The prediction is preferably made for PARP inhibitors Talazoparib (BMN-673), Olaparib (AZD-2281), Rucaparib (AG014699, PF-01367338), Veliparib (ABT-888), CEP 9722, MK 4827 and/or BGB-290.

BRCA1, BRCA2 and PALB2 encode repair enzymes that repair such double-strand breaks by homologous recombination. If these genes are active and functional, the single and double strand breaks resulting from PARP inhibition can be efficiently repaired. The tumor cell can survive. The therapy with PARP inhibitors works poorly in this case.

In some tumors, however, the function of BRCA1, BRCA2 and/or PALB2 is impaired, since the corresponding genes carry, for example, a germ line mutation or a somatic mutation and/or the genes are inactivated by methylation. In these cases, the DNA damage resulting from PARP inhibition cannot be repaired and the tumor cell dies. Tumor cells in which BRCA1, BRCA2 or PALB2 are inactivated by mutation and/or methylation therefore respond well to treatment with PARP inhibitors.

The method of the present invention can be used for testing tumors whether they are likely to respond to a monotherapy or combination therapy with PARP inhibitors due to the inactivation of DNA repair enzymes by methylation and/or mutation of the corresponding gene. Without limitation, a combination therapy can for example include a chemotherapy with cisplatin, a radiation therapy or other therapies.

For example, a hematoxyline-eosine stained section (H&E section) of the formalin-fixed and paraffin-embedded tumor is used to carry out the method of the present invention. Additionally, unstained blank sections of about 10 μm are cut and mounted on glass slides. The tumor-carrying area of the tissue is marked on the H&E sections by a pathologist. The corresponding area of the blank sections is then transferred into a 2 ml reaction tube using a scalpel. Ideally, an area measuring approximately 1 to 3 cm$^2$ is used. This area can also be obtained from several blank sections.

The tissue can then be deparaffinized and lysed using proteinase K, for example. The lysed tissue can be directly transferred into a bisulfite conversion reaction for the converting the genomic DNA without prior extraction. Alternatively, the genomic DNA can also be extracted from the lysed tissue prior to conversion. After conversion, the converted genomic DNA is purified. Silica membrane columns are suitable for this purpose, for example. The lysis of the tissue, the bisulfite conversion of the DNA and the subsequent purification can be carried out, for example, with the innuConvert All-In-One Kit (Analytik Jena, Jena, Germany) in accordance with the protocols contained in the kit.

The determination of the mutation and methylation state can then be carried out using different variants of the method of the present invention.

For example, it is possible to use a multiplex PCR amplification of the converted genomic DNA with primer pairs designed for amplifying at least a first part of the converted genomic DNA suspected of containing a mutation and a second part containing a CpG dinucleotide whose methylation state is to be analyzed.

For BRCA1 methylation analysis, primers are used which are preferably, but not exclusively, designed to hybridize at least partially to the genomic sequence SEQ ID NO:61 after this sequence has been converted. For example, the primer pair with SEQ ID NO:86 and SEQ ID NO:87 or the primer pair with SEQ ID NO:88 and SEQ ID NO:89 can be suitable. For BRCA2 methylation analysis, primers are used which are preferably, but not exclusively, designed to hybridize at least partially to the genomic sequence SEQ ID NO:39 after this sequence has been converted.

For the mutation analysis of BRCA1, preferably one or more primer pairs are used whose target sequences are located at least partially in sections of the converted genomic DNA, which in the untreated wild typical state had at least 95% sequence identity with one of the sequences selected from SEQ ID NO:46 to SEQ ID NO:63, or combinations thereof, in particular comprising SEQ ID NO:56.

For the BRCA2 mutation analysis, one or more primer pairs are preferably used whose target sequences are located at least partially in sections of the converted genomic DNA, which in the unconverted wild typical state had at least 95% sequence identity with one of the sequences selected from SEQ ID NO:34 to SEQ ID NO:45, or combinations thereof. In addition, one or more primer pairs whose target sequences are located in sections of the converted genomic DNA of the PALB2 gene locus are particularly preferred.

It is possible to subsequently sequence the products of the PCR amplification using NGS, for example, wherein the determination of the methylation state or the presence or absence of the mutation is preferably performed on a quantitative basis. In this way, for example, the percentage of methylated and mutated alleles can be determined on the basis of the quantified methylation state and/or the ratio of converted genomic DNA with mutation to converted genomic DNA without mutation.

The mutation and methylation analysis can also be carried out using MLPA or WGSBS as described in example 7 or suitable variations of these methods.

In another embodiment, the formalin-fixed tumor is not macrodissected. For example, sections of 10 μm each of a tumor-bearing tissue block can be transferred directly into a 2 ml reaction tube. The subsequent lysis, conversion and purification can be performed as described above.

The application of this method is particularly suitable for diseases in which the presence of BRCA1 and BRCA2 mutations is of great importance, such as breast and ovarian cancer, melanoma and prostate cancer.

Example 9: Prediction by Combined Mutation and Methylation Analysis of Different Genes While in the previous example a combined mutation and methylation analysis within the same gene allows a prediction with regard to the response to therapy, it was also recognized in the course of the present invention that a combined determination of a mutation or methylation state of different genes can provide a particularly advantageous prediction in connection with certain malignant diseases.

One example concerns the treatment with temozolomide. Temozolomide is an alkylating cytostatic agent used for the simultaneous, adjuvant and palliative therapy of glioblastomas in combination with radiotherapy. Temozolomide leads to DNA damage by alkylating the DNA. These DNA damages can trigger apoptosis of the tumor cells and thus kill them.

The enzyme 06-methylguanine DNA methyl transferase (MGMT) is involved in the repair of alkylated DNA. This enzyme can therefore reduce the effect of temozolomide. In some glioblastomas, MGMT is repressed by the methylation of the gene. Patients whose tumors exhibit a reduced expression of MGMT therefore respond well to treatment with temozolomide. The methylation state of MGMT is therefore a predictive biomarker for the response to temozolomide treatment.

It is meanwhile known that in addition to the methylation of MGTM, some mutations, such as mutations of the genes IDH1 and IDH2 as well as amplifications of EGFR, can also predict response to treatment with temozolomide. The use of drugs that specifically inhibit the mutant variant of IDH1 and IDH2 is a promising therapeutic approach. Tumors with amplification of EGFR can respond to treatment with therapeutic monoclonal antibodies directed against EGFR. Tumors that have mutations in IDH1 or IDH2 respond well to therapy with drugs that inhibit the mutant variants. The combined methylation analysis of MGMT and mutation analysis of IDH1, IDH2 and/or EGFR in converted genomic DNA from glioblastomas or other tumors with IDH1, IDH2 and/or EGFR mutations is therefore a clinically relevant application of the present invention. In particular, the method according to the invention comprises a methylation analysis of the MGMT gene, preferably comprising at least part of a sequence which has at least 95% sequence identity with SEQ ID NO:92 in the unconverted wild typical state and/or a mutation analysis of IDH1 and/or IDH2. In particular, the mutation analysis can be designed to determine a mutation in at least part of a sequence which has at least 95% sequence identity with SEQ ID NO:84 and/or SEQ ID NO:85 in the unconverted wild typical state.

Example 10: Use of the Method for Prognosis and/or Prediction

The analysis of prognostic biomarkers allows determination of the aggressiveness of a malignant disease, such as a tumor.

One of the unique features of the present invention is that the simultaneous mutation and methylation analysis can be used to obtain a comprehensive molecular diagnostic profile in which prognostic biomarkers such as the methylation state of a gene and predictive biomarkers such as a mutation in a therapeutically relevant gene are equally incorporated. In this way, it is possible for the first time to establish a functional relationship between such prognostic and predictive genetic dispositions in a single analysis in order to provide patients with more targeted and, if necessary, more dynamic therapy.

In a further application of this invention, the methylation analysis of a gene as a prognostic biomarker and the mutation analysis of a therapeutically relevant gene as a predictive biomarker of a malignant disease are combined in one analysis.

For this type of analysis, it is provided in particular that the methylation analysis includes at least part or more parts of the prognostic DNA methylation biomarkers PITX2, preferably at least part of a sequence which, in the unconverted wild typical state, has at least 95% sequence identity with SEQ ID NO:90 and/or SEQ ID NO:91, CDO1, PLAU, POU4F3, TFF1, CXCL12, or combinations thereof.

Example 11: Determination of the Proportion of DNA of a Malignant Disease in Genomic DNA by Combined Mutation Analysis and Methylation Analysis The present invention also identified the problem that some malignant diseases have a low overall methylation of many genes, which are otherwise usually aberrant hypermethylated in malignant diseases. In such cases, it can be problematic to determine the proportion of DNA from the malignant disease in a sample of genomic DNA using methylation analysis alone, as DNA from the malignant disease may be present, although little or no DNA methylation is detected. This can result in false-negative diagnoses.

This problem is solved in a further embodiment of the invention, wherein the mutation analysis comprises the determination of at least one recurrent mutation or at least one mutation of a recurrently mutated gene. In particular, the proportion of DNA of the malignant disease in the genomic DNA can be determined on the basis of at least one recurrent mutation or at least one mutation of a recurrently mutated gene. Preferably, the mutation analysis in step B) is carried out under conditions that allow a quantitative determination of the at least one recurrent mutation or the at least one mutation of the recurrently mutated gene in order to quantify the proportion of DNA of the malignant disease in the genomic DNA.

If, for example, a mutation analysis of EGFR or KRAS according to the present invention is to be carried out in the plasma of a patient with colorectal cancer, then it is also advisable to determine further mutations that are very common in colorectal cancer, in order to use these mutations alone or together with the methylation analysis for determining the proportion of DNA from the malignant disease in the genomic DNA. In colorectal cancer, for example, the mutation analysis may include TP53 and/or APC for determining a mutation of a recurrently mutated gene. The proportion of DNA of the malignant disease in the genomic DNA can then be determined solely on the basis of the mutation of the recurrently mutated gene or in combination with the methylation analysis to obtain a particularly robust result.

The determination of the recurrent mutation or mutation in the recurrently mutated gene can in particular depend on which organ or tissue type is affected by the malignant disease. In the following, different organ and tissue types are listed together with the respective genes, which are preferably at least partially covered by the mutation analysis for the determination of a recurrent mutation or a mutation of a recurrently mutated gene. The mutation analysis may also include combinations of these genes to determine one or more recurrent mutations or one or more mutations of recurrently mutated genes.

Vulva: TP53, CDKN2A. Vagina: TP53. Urinary tract: TERT, FGFR3, TP53, STAG2, KDM6A, PIK3CA, CDKN2A, ARID1A, RB1. Upper aerodigestive tract: TP53, CDKN2A, NOTCH1. Thyroid gland: BRAF, RET, TSHR, TERT, NRAS. Thymus: ALK, TP53, KIT, MEN1, CDKN2A, RET. Testicles: CTNNB1, KIT, TP53, KRAS. Stomach: TP53, ARID1A, CDH1, APC, PIK3CA, KMT2C, TRRAP, CTNNB1. Soft tissues: KIT, CTNNB1, MED12, NF2, SMARCB1, NF1, PDGFRA, TP53, TERT, CDKN2A, VHL. Small intestine: PDGFRA, KRAS, TP53, CTNNB1, APC, MEN1, SMAD4, GNAS. Skin: BRAF, TP53, TERT, CDKN2A, GRIN2A, PTCH1, NRAS, ROS1, FGFR3, KMT2C, HRAS. Salivary gland: TP53, HRAS, PIK3CA, CDKN2A, CREBBP, KDM6A, CTNNB1. Prostate: TP53, PTEN, SPOP, KRAS. Pleura: DICER1, CDKN2A, BAP1, NF2, TERT, TP53. Peritoneum: GNAS, KRAS, TP53, EGFR, SMAD4. Pancreas: KRAS, TP53, GNAS, SMAD4, CDKN2A. Ovary: TP53, FOXL2, KRAS, PIK3CA, ARID1A, BRAF. Esophagus: TP53, CDKN2A, NOTCH1. Nervous system: BRAF, TERT, NRAS, CDKN2A. Lung: TP53, EGFR, KRAS. Liver: TP53, CTNNB1, TERT. Colon: APC, TP53, KRAS, ATM, PIK3CA, SMAD4, BRAF. Kidney: VHL, PBRM1, BAP1, SETD2, CTNNB1, AMER1, TP53, WT1. Leukaemia and lymphomas: JAK2, NPM1, FLT3, MYD88, KIT, CALR, ABL1, TET2, NOTCH1, DNMT3A, ASXL1. Endometrium: PTEN, PIK3CA, CTNNB1, TP53, PIK3R1, ARID1A, KRAS. Uterine cervix: PIK3CA, KMT2C, KMT2D, KRAS. Central nervous system: IDH1, TERT, TP53, CDKN2A, PTEN, H3F3A. Breast: PIK3CA, TP53, CDH1. Bone: IDH1, GNAS, TP53, H3F3B, COL2A1. Galle: TP53, KRAS, CDKN2A, KMT2C, IDH1, ARID1A. Adrenal gland: KCNJ5, TP53, CTNNB1, NF1.

Example 12: Detection of Circulating Tumor Cells (CTCs)

The analysis of circulating tumor cells (CTCs) has great potential for improving the treatment of patients with malignant diseases. For example, the presence of CTCs in the blood can make it possible to determine the tumor stage, as it indicates occult remote metastasis at an early time. Molecular analysis of CTCs can also provide information about the potential response of these cells to certain therapies. For example, if the BRAF mutation V600E is present in the CTCs of melanoma patients, these cells are likely to respond to treatment with Vemurafenib.

However, the specific detection of CTCs is problematic. Conventional methods are based, for example, on the enrichment of CTCs using epithelial surface markers. The epithelial cell adhesion molecule EpCAM, for example, indicates that the cell could be a tumor cell because this cell has epithelial characteristics that are not shown by other circulating cells, which are mostly of haematopoietic origin. With the help of antibodies against EpCAM, these cells can be specifically labelled and purified e. g. using magnetic particles or enriched in the body with a catheter that carries antibodies against EpCAM on the surface. This procedure has two major problems. Firstly, not all tumor cells carry the corresponding proteins such as EpCAM on their surface, which means that the method is often not sufficiently sensitive, especially in case of small amounts of CTCs. Secondly, there are sporadic circulating cells with characteristics of epithelial cells, but which are not of tumorous origin, so that the method also lacks specificity.

Other known methods for enriching CTCs are based on size selection. CTCs are larger than most other circulating cells and can be enriched using pores of a suitable size. Here, too, the problem of specificity exists, since other cells of non-tumorous origin can also be enriched.

If a mutation analysis is carried out in the supposedly enriched CTCs from conventional methods, it can lead to false-negative results because, instead of the CTCs, also unspecifically enriched benign cells are analysed.

The method of the present invention solves this problem, for example, by a combined mutation and methylation analysis using converted genomic DNA of circulating cells. It is then possible to confirm a malignant origin of the isolated cells using the methylation analysis. In this way, the specificity of the mutation analysis can be significantly improved.

Example 13: Normalized Methylation Analysis

It has already been shown in the preceding examples that a normalized determination of mutations by correlating the mutation analysis with the methylation analysis is possible with the method of the present invention. In this way, for example, the proportion of DNA from a malignant disease in a sample with genomic DNA can be determined by methylation analysis to avoid that absence of DNA from the malignant disease in the sample leads to a false-negative mutation analysis. Thus, for example, a substantial improvement of the sensitivity of the mutation analysis is achieved.

But also the reverse case, i. e. a normalization of the methylation analysis on the basis of the mutation analysis, is associated with special advantages according to the invention.

A malignant disease, for example a tumor, is usually heterogeneous, i. e. different subtypes of cells can be present, which sometimes have different characteristics. If, for example, the tumor is treated by therapy, e. g. chemotherapy, targeted therapy or immunotherapy, not all cells respond in the same way and a population of tumor cells can often survive. This can be a certain subtype, for example.

The methylation analysis of the present invention is particularly suitable for identifying such subtypes. Methylation biomarkers are often not methylated in all tumor cells. Therefore, the analysis of methylation biomarkers allows the identification of subtypes of cells that have a specific property. This can comprise, as already explained in the previous examples, a certain response to a certain therapy or a certain aggressiveness.

If the method of the present invention is used to examine converted genomic DNA with regard to such predictive and prognostic methylation biomarkers, it is of interest how much DNA of the malignant disease is present in the sample. For instance, if the methylation analysis includes MGMT in a sample with genomic DNA of a glioblastoma in order to predict e. g. a response to Temozolomide, it can be relevant to determine in how many percent of the tumor cells MGMT is methylated.

For example, if a tumor carries a mutation that contributed to the development of the tumor, then this mutation is cloned in all tumor cells and the method of the invention enables the proportion of tumor cells to be determined on the basis of the mutation analysis. For example, a mutation of IDH1 or IDH2 can be determined in case of the glioblastoma. Subsequently, a ratio can be formed from the proportion of genomic DNA in which methylation was detected and the proportion of genomic DNA in which the mutation was detected. This ratio can be used as a measure of the proportion of the sought subtype of cells in the malignant disease. For example, the proportion of MGMT-methylated cells of the glioblastoma that are likely to respond to the therapy can be determined.

PITX2 is for instance a very powerful prognostic methylation marker for breast, prostate, lung, head and neck tumors. In this context, the relative amount of PITX2 methylation in the tissue is prognostic. In certain embodiments, the methylation analysis of the method of the present invention therefore comprises the methylation state of one or more CpG dinucleotides of PITX2. Preferably, the mutation analysis includes in this embodiment the determination of at least one recurrent mutation or a mutation of a recurrently mutated gene as described in Example 11. In particular, the mutation analysis preferably comprises at least part of TP53.

A normalization of PITX2 methylation by means of recurrent mutations such as mutations of TP53 enables, according to the invention, a more precise determination of, for example, the proportion of methylated tumor DNA in the total tumor DNA and thus also, for example, a more differentiated diagnosis, prognosis and prediction of malignant diseases.

The invention claimed is:

1. A method for determining at least one mutation in genomic DNA, comprising
  A) converting at least a part of the cytosines contained in said genomic DNA to uracil or another base with a base-pairing behavior and/or molecular weight distinguishable from that of cytosine, and
  B) in a single reaction mixture, (i) performing a mutation analysis with said genomic DNA obtained from step A) to determine said at least one mutation, and (ii) performing a methylation analysis with said genomic DNA obtained from step A) to determine a methylation state of at least one CpG dinucleotide contained in said genomic DNA, and determining whether DNA of a malignant disease is contained in said genomic DNA based on said methylation state of the CpG dinucleotide, wherein step (i) and step (ii) comprise adding, to the single reaction mixture, at least a first pair of oligonucleotides for amplifying at least a first part of the genomic DNA which is suspected of containing said at least one mutation, and at least a second pair of oligonucleotides for amplifying at least a second part of the genomic DNA which contains at least one CpG dinucleotide whose methylation state is analyzed, and wherein the mutation analysis of step (B)(i) is performed on the negative strand and the methylation analysis of step (B)(ii) is performed on the positive strand.

* * * * *